United States Patent
Shirude et al.

(10) Patent No.: US 11,008,301 B2
(45) Date of Patent: May 18, 2021

(54) PIPERIDINONE FORMYL PEPTIDE 2 RECEPTOR AGONISTS

(71) Applicant: BRISTOL-MYERS SQUIBB COMPANY, Princeton, NJ (US)

(72) Inventors: Pravin Sudhakar Shirude, Bangalore (IN); Amit Kumar Chattopadhyay, Bangalore (IN); Chandrasekhar Rachamreddy, Kadapa District (IN); Nicholas R. Wurtz, Pennington, NJ (US); Ellen K. Kick, Pennington, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 16/619,960

(22) PCT Filed: Jun. 8, 2018

(86) PCT No.: PCT/US2018/036624
§ 371 (c)(1),
(2) Date: Dec. 6, 2019

(87) PCT Pub. No.: WO2018/227058
PCT Pub. Date: Dec. 13, 2018

(65) Prior Publication Data
US 2020/0207735 A1   Jul. 2, 2020

Related U.S. Application Data

(60) Provisional application No. 62/517,203, filed on Jun. 9, 2017.

(51) Int. Cl.
| | |
|---|---|
| *C07D 401/10* | (2006.01) |
| *A61P 9/00* | (2006.01) |
| *C07D 401/14* | (2006.01) |
| *C07D 413/14* | (2006.01) |
| *C07D 491/107* | (2006.01) |
| *C07D 498/08* | (2006.01) |

(52) U.S. Cl.
CPC ............ *C07D 401/10* (2013.01); *A61P 9/00* (2018.01); *C07D 401/14* (2013.01); *C07D 413/14* (2013.01); *C07D 491/107* (2013.01); *C07D 498/08* (2013.01)

(58) Field of Classification Search
CPC .. C07D 401/10; C07D 401/14; C07D 413/14; C07D 491/107; C07D 498/08; A61P 9/00
See application file for complete search history.

(56) References Cited

U.S. PATENT DOCUMENTS

| | | | |
|---|---|---|---|
| 9,822,069 B2 | 11/2017 | Takahashi et al. | |
| 10,029,983 B2 | 7/2018 | Takahashi et al. | |
| 10,252,992 B2 | 4/2019 | Takahashi et al. | |
| 10,464,891 B2 | 11/2019 | Takahashi et al. | |
| 10,676,431 B2 * | 6/2020 | Shirude | A61P 9/00 |
| 10,717,708 B2 * | 7/2020 | Wurtz | A61P 9/10 |
| 2018/0325869 A1 * | 11/2018 | Ostrowski | A61K 31/00 |
| 2019/0270704 A1 * | 9/2019 | Shirude | C07D 403/12 |
| 2020/0069644 A1 * | 3/2020 | Ostrowski | A61P 9/04 |
| 2020/0123108 A1 * | 4/2020 | Wurtz | C07D 401/04 |
| 2020/0199113 A1 * | 6/2020 | Smallheer | A61P 9/00 |
| 2020/0255375 A1 * | 8/2020 | Shirude | A61P 9/04 |
| 2020/0299237 A1 * | 9/2020 | Wurtz | C07D 401/10 |

FOREIGN PATENT DOCUMENTS

| | | | |
|---|---|---|---|
| WO | WO2006063113 A2 | 6/2006 | |
| WO | WO-2015079692 A1 * | 6/2015 | ............. A61P 25/04 |
| WO | WO2016189876 A1 | 12/2016 | |
| WO | WO2016189877 A1 | 12/2016 | |
| WO | WO2017091496 A1 | 6/2017 | |
| WO | WO2017100390 A1 | 6/2017 | |
| WO | WO2018227061 A1 | 12/2018 | |
| WO | WO2018227065 A1 | 12/2018 | |
| WO | WO2018227067 A1 | 12/2018 | |
| WO | WO2019173182 A1 | 9/2019 | |

OTHER PUBLICATIONS

Qin; Nat. Commun. 2017, 8, 14232. (Year: 2017).*
Sigma-Aldrich Online Catalog; Entries for Hexamethyleneimine (Homopiperidine), Homopiperazine and Homomorpholine. Downloaded on Oct. 15, 2020 at https://www.sigmaaldrich.com/catalog/product/aldrich/h10401 (Year: 2020).*
Klapars et al., "A General and Efficient Copper Catalyst for the Amidation of Aryl Halides", J. Am. Chem. Soc. 2002, 124, 7421-7428.
Yin et al., "Palladium-Catalyzed Intermolecular Coupling of Aryl Halides and Amides" Organic Letters vol. 2(8) 1101-1104 (2000).
Yin, et al., "Pd-Catalyzed Intermolecular Amidation of Aryl Halides: The Discovery that Xantphos Can Be Trans-Chelating in a Palladium Complex", J. Am. Chem. Soc. 2002, 124, 6043-6048.

(Continued)

*Primary Examiner* — Daniel R Carcanague
(74) *Attorney, Agent, or Firm* — Hong Liu

(57) ABSTRACT

The disclosure relates to compounds of formula (I), which are formyl peptide 2 (FPR2) receptor agonists and/or formyl peptide 1 (FPR1) receptor agonists. The disclosure also provides compositions and methods of using the compounds, for example, for the treatment of atherosclerosis, heart failure, and related diseases.

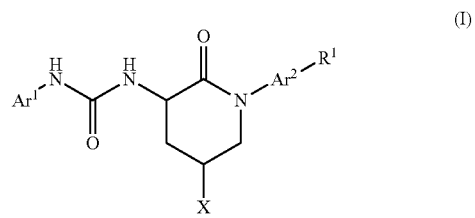

9 Claims, No Drawings

(56) References Cited

OTHER PUBLICATIONS

Allen, Jr., Loyd V., "Remington: The Science and Practice of Pharmacy, vol. I and vol. II. Twenty-second edition", Pharmaceutical Press, 2012, p. 2724.
Chandrasekharan et al., "Lipoxins: nature's way to resolve inflammation", Journal of Inflammation Research, 2015:8 181-192.
Fredman et al., "Targeted nanoparticles containing the proresolvingpeptide Ac2-26 protect against advancedatherosclerosis in hypercholesterolemic mice", Sci. Trans. Med., 2015, 7(275); pp. 275ra20).
Gavins, Felicity N.E., "Are formyl peptide receptors novel targets for therapeutic intervention ischaemia-reperfusion injury?" Trends in Pharmacological Sciences, vol. 31(6), pp. 266-276 (2010).
Greene, T.W. et al., Protecting Groups in Organic Synthesis, 4th Edition, Wiley (2007)).
Kain et al., "Resolvin D1 activates the inflammation resolving response at splenic and ventricular site following myocardial infarction leading to improved ventricular function", Journal of Molecular and Cellular Cardiology, vol. 84, pp. 24-35 (2015).
Kiyomor, et al., "An Efficient Copper-Catalyzed Coupling of Aryl Halides with Imidazoles", Tetrahedron Letters 40 (1999) 2657-2660.
Klapars, et al., "A General and Efficient Copper Catalyst for the Amidation of Aryl Halides and the N-Arylation of Nitrogen Heterocycles", J. Am. Chem. Soc. 2001, 123, 7727-7729.

Liu et al., "Lipoxin A4 ameliorates ischemia/reperfusion induced spinal cord injury in rabbit model", Int. J. Clin.Exp. Medicine, Vo. 8(8), pp. 12826-12833 (2015.
Perretti, et al., "Resolution Pharmacology:Opportunities for Therapeutic Innovationin Inflammation", Trends in Pharmacological Sciences,vol. 36(11) 2015.
Petri et al., "The role of the FPR2/ALX receptor in atherosclerosis development and plaque stability", Cardiovascular Research, vol. 105, pp. 65-74 (2015).
Romano et al., "Lipoxins and aspirin-triggered lipoxinsin resolution of inflammation", European Journal of Pharmacology vol. 760 pp. 49-63 (2015).
Shaughnessy, et al., "Copper-Catalyzed Amination of Aryl and Alkenylelectrophiles", Organic Reactions, vol. 85(1), pp. 1-668 (2014).
Surry, et al. "Biaryl Phosphane Ligands in Palladium-CatalyzedAmination", Angew.Chem.Int.Ed. vol. 47,6338-6361 (2008).
Surry, et al., "Dialkylbiaryl Phosphines in Pd-Catalyzed Amination: A User's Guide", Chem Sci. vol. 2(1): 27-50 (2011).
Vantourout, et al., "Chan-Evans-Lam Amination of Boronic Acid Pinacol (BPin) Esters:Overcoming the Aryl Amine Problem", J. Org. Chem. 2016, 81, 3942-3950.
Ye et al., "International Union of Basic and Clinical Pharmacology. LXXIII. Nomenclature for the Formyl Peptide Receptor (FPR) Family", Pharmacological Reviews, vol. 61(2), 2009.

* cited by examiner

PIPERIDINONE FORMYL PEPTIDE 2 RECEPTOR AGONISTS

CROSS-REFERENCE TO RELATED APPLICATION

This application claims the benefit of U.S. Provisional Application Ser. No. 62/517,203 filed on Jun. 9, 2017, which is hereby incorporated by reference in its entirety.

BACKGROUND OF THE INVENTION

The present invention relates to novel piperidinone compounds, which are formyl peptide 2 (FPR2) receptor agonists and/or formyl peptide 1 (FPR1) receptor agonists, compositions containing them, and methods of using them, for example, for the treatment of atherosclerosis, heart failure, chronic obstructive pulmonary disease (COPD), and related diseases.

Formyl peptide receptor 2 (FPR2) belongs to small group of seven-transmembrane domain, G protein-coupled receptors that are expressed mainly by mammalian phagocytic leukocytes and are known to be important in host defense and inflammation. FPR2 shares significant sequence homology with FPR1 and FPR3. Collectively, these receptors bind large number of structurally diverse group of agonists, including N-formyl and nonformyl peptides which act as chemo attractants and activate phagocytes. The endogenous anti-inflammatory peptide Annexin A1 and its N-terminal fragments also bind human FPR1 and FPR2. Importantly, anti-inflammatory eicosanoid lipoxin A4, which belongs to newly discovered class of small pro-resolution mediators (SPMs), has been identified as an agonist for FPR2 (Ye R D., et al., Pharmacol. Rev., 2009, 61, 119-61).

Endogenous FPR2 pro-resolution ligands, such as lipoxin $A_4$ and Annexin A1 trigger a wide array of cytoplasmatic cascades such as Gi coupling, $Ca^{2+}$ mobilization and □-arrestin recruitment via FPR2. Activation of FPR2 by lipoxin $A_4$ modifies the effects of peptidic agonists, such as serum amyloid A (SAA), and has alternative effects on phosphorylation pathways depending on the cell type. Lipoxins regulate components of both innate and adaptive immune systems including neutrophils, macrophages, T-, and B-cells. In neutrophils, lipoxins modulate their movement, cytotoxicity and life span. In macrophages, lipoxins prevent their apoptosis and enhance efferocytosis. In most inflammatory cells, lipoxins also down-regulate expression of several pro-inflammatory cytokines, such as IL-6, IL-1□ and IL-8 as well as up-regulate expression of anti-inflammatory cytokine IL-10 (Chandrasekharan J A, Sharma-Walia N., J. Inflamm. Res., 2015, 8, 181-92). The primary effects of lipoxin on neutrophils and macrophages are termination of inflammation and initiation of resolution of inflammation. The latter is primarily responsible for enhancing anti-fibrotic wound healing and returning of the injured tissue to homeostasis (Romano M., et al., Eur. J. Pharmacol., 2015, 5, 49-63).

Chronic inflammation is part of the pathway of pathogenesis of many human diseases and stimulation of resolution pathways with FPR2 agonists may have both protective and reparative effects. Ischaemia-reperfusion (I/R) injury is a common feature of several diseases associated with high morbidity and mortality, such as myocardial infarction and stroke. Non-productive wound healing associated with cardiomyocyte death and pathological remodeling resulting from ischemia-reperfusion injury leads to scar formation, fibrosis, and progressive lost of heart function. FPR2 modulation is proposed to enhance myocardial wound healing post injury and diminish adverse myocardial remodeling (Kain V., et al., J. Mol. Cell. Cardiol., 2015, 84, 24-35). In addition, FPR2 pro-resolution agonists, in the central nervous system, may be useful therapeutics for the treatment of a variety of clinical I/R conditions, including stroke in brain (Gavins F N., Trends Pharmacol. Sci., 2010, 31, 266-76) and I/R induced spinal cord injury (Liu Z Q., et al., Int. J. Clin. Exp. Med., 2015, 8, 12826-33).

In addition to beneficial effects of targeting the FPR2 with novel pro-resolution agonists for treatment of I/R induced injury therapeutic, utility of these ligands can also be applied to other diseases. In the cardiovascular system both the FPR2 receptor and its pro-resolution agonists were found to be responsible for atherogenic-plaque stabilization and healing (Petri M H., et al., Cardiovasc. Res., 2015, 105, 65-74; and Fredman G., et al., Sci. Trans. Med., 2015, 7(275); 275ra20). FPR2 agonists also have been shown to be beneficial in preclinical models of chronic inflammatory human diseases, including: infectious diseases, psoriasis, dermatitis, occular inflammation, sepsis, pain, metabolic/diabetes diseases, cancer, COPD, asthma and allergic diseases, cystic fibrosis, acute lung injury and fibrosis, rheumatoid arthritis and other joint diseases, Alzheimer's disease, kidney fibrosis, and organ transplantation (Romano M., et al., Eur. J. Pharmacol., 2015, 5, 49-63, Perrett, M., et al., Trends in Pharm. Sci., 2015, 36, 737-755).

DESCRIPTION OF THE INVENTION

The invention encompasses compounds of formula I, which are formyl peptide 2 (FPR2) receptor agonists and/or formyl peptide 1 (FPR1) receptor agonists, compositions containing them, and methods of using them, for example, in the treatment of atherosclerosis, heart failure, chronic obstructive pulmonary disease (COPD), and related diseases.

One aspect of the invention is a compound of formula I

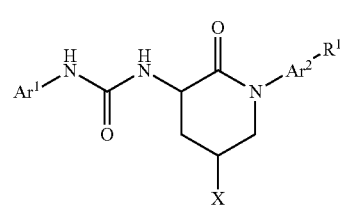

I where:
$Ar^1$ is phenyl, pyridinyl, pyridazinyl, pyrimidinyl, pyrazinyl, or benzodioxyl, and is substituted with 1-3 substituents selected from cyano, halo, alkyl, fluoroalkyl, alkoxy, fluoroalkoxy, and alkylthio;
$Ar^2$ is phenyl, pyridinyl, pyridazinyl, pyrimidinyl, or pyrazinyl, and is substituted with 0-3 substituents selected from cyano, halo, alkyl, fluoroalkyl, cycloalkyl, alkoxy, and fluoroalkoxy;
$R^1$ is azetidinyl, pyrrolidinyl, piperidinyl, piperazinyl, morpholinyl, homopiperidinyl, homompiperazinyl, or homomorpholinyl, and is substituted with 0-3 substituents selected from cyano, fluoro, alkyl, fluoroalkyl, hydroxyalkyl, alkoxyalkyl, cycloalkyl, hydroxy, alkoxy, fluoroalkoxy, $(R^2)(R^3)N$, alkylcarbonyl, $((R^2)(R^3)N)$carbonyl, alkylsufonyl, and oxo;

or R¹ is 4-(5-azaspiro[2.4]heptan-5-yl, 1-oxa-8-azaspiro[4.5]decan-8-yl, 2-oxa-6-azaspiro[3.3]heptanyl, 2-oxa-8-azaspiro[4.5]decan-8-yl, or 8-oxa-3-azabicyclo[3.2.1]octanyl, or tetrahydro-1H-furo[3,4-c]pyrrol-5(3H)-yl; and
R² is hydrogen, alkyl, haloalkyl, alkylcarbonyl, or alkylsulfonyl;
R³ is hydrogen or alkyl;
or NR²R³ taken together is selected from azetidinyl, pyrrolidinyl, piperidinyl, piperazinyl, and morpholinyl, and is substituted with 0-3 substituents selected from fluoro, alkyl, fluoroalkyl, alkoxy, and haloalkoxy; and
X is hydrogen, fluoro, hydroxy, or alkoxy;
or a pharmaceutically acceptable salt thereof.

Another aspect of the invention is a compound of formula I where:
Ar¹ is phenyl, pyridinyl, pyridazinyl, pyrimidinyl, pyrazinyl, or benzodioxyl, and is substituted with 1-3 substituents selected from cyano, halo, alkyl, fluoroalkyl, alkoxy, fluoroalkoxy, and alkylthio;
Ar² is phenyl, pyridinyl, pyridazinyl, pyrimidinyl, or pyrazinyl, and is substituted with 0-3 substituents selected from cyano, halo, alkyl, fluoroalkyl, alkoxy, and fluoroalkoxy;
R¹ is azetidinyl, pyrrolidinyl, piperidinyl, piperazinyl, morpholinyl, homopiperidinyl, homopiperazinyl, or homomorpholinyl, and is substituted with 0-3 substituents selected from cyano, fluoro, alkyl, fluoroalkyl, hydroxyalkyl, alkoxyalkyl, hydroxy, alkoxy, haloalkoxy, alkylcarbonyl, alkylsufonyl, and oxo;
or R¹ is 2-oxa-6-azaspiro[3.3]heptanyl or 8-oxa-3-azabicyclo[3.2.1]octanyl; and
X is hydrogen, fluoro, hydroxy, or alkoxy;
or a pharmaceutically acceptable salt thereof.

Another aspect of the invention is a compound of formula I where Ar¹ is phenyl or pyridinyl and is substituted with 1-3 substituents selected from cyano, halo, alkyl, fluoroalkyl, alkoxy, fluoroalkoxy, alkylthio, and alkylsulfonyl.

Another aspect of the invention is a compound of formula I where Ar² is phenyl or pyridinyl and is substituted with 0-3 substituents selected from cyano, halo, alkyl, fluoroalkyl, alkoxy, and fluoroalkoxy.

Another aspect of the invention is a compound of formula I where R¹ is azetidinyl, pyrrolidinyl, piperidinyl, piperazinyl, morpholinyl, homopiperidinyl, homopiperazinyl, or homomorpholinyl, and is substituted with 0-3 substituents selected from cyano, fluoro, alkyl, fluoroalkyl, hydroxyalkyl, alkoxyalkyl, hydroxy, alkoxy, fluoroalkoxy, alkylcarbonyl, alkylsufonyl, and oxo.

For a compound of Formula I, the scope of any instance of a variable substituent, including Ar¹, Ar², R¹, R², R³, and X can be used independently with the scope of any other instance of a variable substituent. As such, the invention includes combinations of the different aspects.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. Terms with a hydrocarbon moiety (e.g. alkoxy) include straight and branched isomers for the hydrocarbon portion. "Halo" includes fluoro, chloro, bromo, and iodo. "Haloalkyl" and "haloalkoxy" include all halogenated isomers from monohalo to perhalo. "Aryl" means a monocyclic or bicyclic aromatic hydrocarbon group having 6 to 12 carbon atoms. Bicyclic ring systems can consist of a phenyl group fused to a aromatic or non-aromatic carbocyclic ring. Representative examples of aryl groups include but are not limited to phenyl, indanyl, indenyl, naphthyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

Heteroaryl includes N-substituted pyridinonyl:

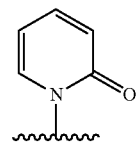 [SMILES: *n1ccccc1=O]

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the compounds. Isotopes include those atoms having the same atomic number but different mass numbers. By way of general example and without limitation, isotopes of hydrogen include deuterium and tritium. Isotopes of carbon include ¹³C and ¹⁴C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

N-formyl peptide receptors (FPRs) are a family of chemo attractant receptors that facilitate leukocyte response during inflammation. FPRs belong to the seven-transmembrane G protein-coupled receptor superfamily and are linked to inhibitory G-proteins (Gi). Three family members (FPR1, FPR2 and FPR3) have been identified in humans and are predominantly found in myeloid cells with varied distribution and have also been reported in multiple organs and tissues. After agonist binding, the FPRs activate a multitude of physiological pathways, such as intra cellular signaling transduction, Ca2+ mobilization and transcription. The family interacts with a diverse set of ligands that includes proteins, polypeptides and fatty acid metabolites which activate both pro-inflammatory and pro-resolution downstream responses.

The FPR2 receptor binds multiple ligands to invoke both inflammatory and anti-inflammatory responses. Inflammation mediator release by FPR2 is promoted by endogenous protein ligands such as Serum amyloid A (SAA) and Amyloid □ (1-42), whereas resolution of inflammation is induced by ligands that include arachidonic acid metabolites, lipoxin A4 (LXA4) and Epi-lipoxin (ATL), and a docosahexenoic acid metabolite, resolvin D1 (RvD1). The pro-resolving fatty acid metabolites mediate inhibition and resolution of inflammation through the FPR2 receptor by stimulating phagocytosis of apotoptic neutrophils by macrophages. Removal of the apototic neutrophils induces the release of cytokines that activate pro-resolution pathways.

The FPR1 receptor was originally isolated as a high affinity receptor for N-Formylmethionine containing peptides, such as N-Formylmethionine-leucyl-phenylalanine (FMLP). The protein directs mammalian phagocytic and blood leukocyte cells to sites of invading pathogens or inflamed tissues and activates these cells to kill pathogens or to remove cellular debris.

FPR2 and FPR1 Cyclic Adenosine Monophosphate (cAMP) Assays. A mixture of forskolin (5 μM final for FPR2 or 10 μM final for FPR1) and IBMX (200 μM final) were added to 384-well Proxiplates (Perkin-Elmer) pre-dotted with test compounds in DMSO (1% final) at final concentrations in the range of 1.7 nM to 100 μM. Chinese Hamster Ovary cells (CHO) overexpressing human FPR1 or human FPR2 receptors were cultured in F-12 (Ham's) medium supplemented with 10% qualified FBS, 250 μg/ml zeocin and 300 μg/ml hygromycin (Life Technologies). Reactions were initiated by adding 2,000 human FPR2 cells per well or 4,000 human FPR1 cells per well in Dulbecco's PBS (with calcium and magnesium) (Life Technologies) supplemented with 0.1% BSA (Perkin-Elmer). The reaction mixtures were incubated for 30 min at room temperature. The level of intracellular cAMP was determined using the HTRF HiRange cAMP assay reagent kit (Cisbio) according to manufacturer's instruction. Solutions of cryptate conjugated anti-cAMP and d2 flurorophore-labelled cAMP were made in a supplied lysis buffer separately. Upon completion of the reaction, the cells were lysed with equal volume of the d2-cAMP solution and anti-cAMP solution. After a 1-h room temperature incubation, time-resolved fluorescence intensity was measured using the Envision (Perkin-Elmer) at 400 nm excitation and dual emission at 590 nm and 665 nm. A calibration curve was constructed with an external cAMP standard at concentrations ranging from 1 μM to 0.1 pM by plotting the fluorescent intensity ratio from 665 nm emission to the intensity from the 590 nm emission against cAMP concentrations. The potency and activity of a compound to inhibit cAMP production was then determined by fitting to a 4-parametric logistic equation from a plot of cAMP level versus compound concentrations.

The exemplified Examples disclosed below were tested in the FPR2 and FPR1 cAMP assay described above and found having FPR2 and/or FPR1 agonist activity. A range of $IC_{50}$ values of ≤1 μM (1000 nM) in one of the assays was observed. Table 1 below lists $EC_{50}$ values in the FPR2 and FPR1 cAMP assays measured for the following examples.

TABLE 1

| Example | hFPR2 cAMP2 $EC_{50}$ (uM) | hFPR1 cAMP $EC_{50}$ (uM) |
|---|---|---|
| 4 | 0.028 | 0.41 |
| 9 | 0.54 | 1.5 |
| 12 | 0.38 | 5.0 |
| 14 | 0.0021 | 0.036 |
| 15 | 0.032 | 0.66 |
| 17 | 0.032 | 0.034 |
| 26 | 0.0037 | 0.012 |
| 34 | 0.40 | 2.2 |
| 45 | 0.0030 | 0.011 |
| 50 | 0.33 | >10 |
| 54 | 0.031 | 0.92 |
| 56 | 0.0018 | 0.045 |
| 69 | 0.014 | 0.19 |
| 70 | 0.0024 | 0.067 |
| 77 | 0.00018 | 1.1 |
| 81 | 0.00031 | 1.7 |
| 83 | 0.00039 | 1.1 |
| 95 | 0.0025 | 0.076 |
| 102 | 0.015 | 0.061 |
| 104 | 0.018 | 0.63 |
| 107 | 0.0026 | 0.33 |

The following Examples were tested in the hFPR2 Assay described above and found having hFPR2 agonist activity with $EC_{50}$ values of ≤0.010 μM (10 nM): 1, 5, 13, 18, 21, 26, 30, 35, 38, 39, 46, 66, 67, 68, 71, 72, 73, 74, 75, 76, 78, 79, 80, 82, 84, 85, 86, 87, 88, 89, 90, 91, 93, 94, 96, 97, 98, 99, 100, 101, 103, 105, 106, 108

The following Examples were tested in the hFPR2 Assay described above and found having hFPR2 agonist activity with $EC_{50}$ values between 0.010 μM and 0.100 μM: 2, 3, 4, 6, 7, 10, 16, 25, 27, 31, 33, 36, 37, 40, 41, 42, 43, 44, 52, 53, 55, 57, 58, 59, 60, 61 and 67.

The following Examples were tested in the hFPR2 Assay described above and found having hFPR2 agonist activity with $EC_{50}$ values between 0.10 μM and 1 μM: 8, 9, 11, 12, 19, 20, 22, 23, 24, 28, 29, 32, 47, 48, 49, 51, 62, 63, and 64.

Pharmaceutical Compositions and Methods of Use

The compounds of the present invention may be administered to patients for the treatment of a variety of conditions and disorders, including atherosclerosis, heart failure, lung diseases including asthma, COPD, cystic fibrosis, neuroinflammatory diseases including multiple sclerosis, Alzheimer's disease, stroke, and chronic inflammatory diseases such as inflammatory bowel disease, rheumatoid arthritis, psoriasis, sepsis, lupus and kidney fibrosis.

Another aspect of the invention is a pharmaceutical composition comprising a therapeutically effective amount of a compound of formula I in combination with a pharmaceutical carrier.

Another aspect of the invention is a pharmaceutical composition comprising a therapeutically effective amount of a compound of formula I in combination with at least one other therapeutic agent and a pharmaceutical carrier.

Unless otherwise specified, the following terms have the stated meanings. The term "patient" means a subject suitable for therapy as determined by practitioners in the field and encompasses all suitable mammalian species including humans that could potentially benefit from treatment with a FPR2 and/or FPR1 agonist as understood by practioners in this field. Common risk factors include, but are not limited to, age, sex, weight, family history, sleep apnea, alcohol or tobacco use, physical inactivity arrthymia or signs of insulin resistance such as acanthosis nigricans, hypertension, dyslipidemia, or polycystic ovary syndrome (PCOS). "Treating" or "treatment" encompass the treatment of a patient as understood by practitioners in the art and include inhibiting the disease-state, i.e., arresting it development; relieving the disease-state, i.e., causing regression of the disease state; and/or preventing the disease-state from occurring in a patient. "Therapeutically effective amount" is intended to include an amount of a compound that is effective or beneficial as understood by practitioners in this field.

"Pharmaceutical composition" means a composition comprising a compound of the invention in combination with at least one additional pharmaceutically acceptable carrier. A "pharmaceutically acceptable carrier" refers to media for the delivery of biologically active agents as understood by practitioners in the art, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents, and dispensing agents. Pharmaceutically acceptable carriers are formulated according to a number of factors known to those of ordinary skill in the art. These include, without limitation, the type and nature of the active agent being formulated; the subject to which the agent-containing composition is to be administered; the intended route of administration of the composition; and the therapeutic indication being targeted. Descriptions of suitable pharmaceutically acceptable carriers and factors involved in their selection are known in the art in such references as Allen, L. V., Jr. et al., *Remington: The Science and Practice of Pharmacy* (2 Volumes), 22nd Edition, Pharmaceutical Press (2012).

Solid compositions are normally formulated in dosage units and compositions providing form about 1 to 1000 mg of the active ingredient per dose are preferred. Some examples of dosages are 1 mg, 10 mg, 100 mg, 250 mg, 500 mg, and 1000 mg.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL.

Another aspect of the invention is a method for treating heart disease comprising administering a therapeutically effective amount of a compound of formula I to a patient.

Another aspect of the invention is a method for treating heart disease wherein the heart disease is selected from the group consisting of angina pectoris, unstable angina, myocardial infarction, heart failure, acute coronary disease, acute heart failure, chronic heart failure, and cardiac iatrogenic damage.

Another aspect of the invention is a method for treating heart disease wherein the treatment is post myocardial infarction.

Another aspect of the invention is the method wherein the heart disease is associated with chronic heart failure.

Another aspect of the invention is the method wherein the treatment is to improve myocardial wound healing.

Another aspect of the invention is the method wherein the treatment is to diminish myocardial fibrosis.

The invention encompasses all conventional modes of administration; oral and parenteral methods are preferred.

Generally, the dosing regimen will be similar to other cardiovascular agents used clinically. The dosage regimen and mode for administration for the compounds of the present invention will depend on known factors known by practitioners in the art and include age, sex, health, medical condition, and weight of the recipient; the nature and extent of the symptoms; the kind of concurrent treatment; the frequency of treatment; the route of administration, and the effect desired. Typically, the daily dose will be 0.1-100 mg/kg body weight daily. Generally, more compound is required orally and less parenterally. The specific dosing regimen, however, will be determined by a physician using sound medical judgment.

Another aspect of the invention is a method for treating heart disease comprising administering a therapeutically effective amount of a compound of formula I to a patient in conjunction with at least one other therapeutic agent.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the invention may be used with one or more, preferable one to three, of the following heart failure agents selected from loop diuretics, Angiotensin converting enzyme (ACE) inhibitors, Angiotensin II receptor blockers (ARBs), angiotensin receptor-neprilysin inhibitors (ARNI), beta blockers, mineralocorticoid receptor antagonists, nitroxyl donors, RXFP1 agonists, APJ agonists and cardiotonic agents. These agents include, but are not limited to furosemide, bumetanide, torsemide, sacubitrial-valsartan, thiazide diruetics, captopril, enalapril, lisinopril, carvedilol, metopolol, bisoprolol, serelaxin, spironolactone, eplerenone, ivabradine, candesartan, eprosartan, irbestarain, losartan, olmesartan, telmisartan, and valsartan.

The compounds of the present invention are also useful as standard or reference compounds, for example as a quality standard or control, in tests or assays involving the FPR2. Such compounds may be provided in a commercial kit, for example, for use in pharmaceutical research involving FPR2 activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving FPR2.

Chemical Methods

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for "aqueous", "sat" or "sat'd" for saturated, "MW" for molecular weight, "mw" or "μwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

| | |
|---|---|
| Ac | Acetic |
| AcOH | acetic acid |
| ACN (or MeCN) | acetonitrile |
| Bn | benzyl |
| Boc | tert-butyl carbonyl |
| Boc$_2$O | Di-tert-butyl dicarbonate |
| Bu | butyl |
| dba (Pd$_2$(dba)$_3$) | dibenzylideneacetone |
| DCM | dichloromethane |
| DIEA or DIPEA | diisopropylethylamine |
| DME | Dimethoxyethane |
| DMF | dimethylformamide |
| DMEDA | N,N'-dimethylethylenediamine |
| DMSO | dimethyl sulfoxide |
| dppf | 1,1'-bis(diphenylphosphino)ferrocene |
| Et | ethyl |
| EtOH | ethanol |
| EtOAc | ethyl acetate |
| i-Bu | isobutyl |
| i-Pr | isopropyl |
| Me | methyl |
| MeOH | methanol |
| NMP | N-Methylpyrrolidone |
| OAc | Acetate |
| Ph | phenyl |
| Pr | propyl |
| RuPhos | 2-dicyclohexylphosphino-2',6'-diipropoxy-1,1'-biphenyl |
| t-Bu | tert-butyl |
| TEA | Triethylamine |
| TFA | Trifluoroacetic acid |
| THF | tetrahydrofuran |

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, and all changes which come within the meaning and range of equivalency of the claims are therefore intended to be embraced.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene, T. W. et al., *Protecting Groups in Organic Synthesis*, 4th Edition, *Wiley* (2007)).

Compounds having the general Formula (IA): wherein rings A, B and C are defined above as Ar$^1$, Ar$^2$ and R$^1$, respectively, and can be prepared by the following one or more of the synthetic Schemes.

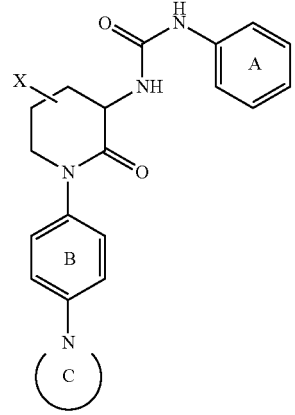

(IA)

1-Arylpiperidinone compounds of this invention wherein rings A and B are substituted phenyl or heteroaryl rings and ring C is a substituted saturated heterocycle can be prepared by the general route shown in Scheme 1, starting from a suitably protected 3-aminopiperidin-2-one 1a, where PG is a protecting group such as Boc or Cbz. Copper-catalyzed coupling of 1a to a substituted iodobenzene 1b or other suitable halo aryl or heteroaryl compound in a suitable solvent such as butanol or dioxane, in the presence of a base such as potassium carbonate and a suitable ligand such as N,N'-dimethylethylenediamine, can afford 1-arylpiperidinones 1c. Additional methods for this transformation include other variations of Ullmann, Goldberg, and Buchwald copper-catalyzed amidation or Buchwald Pd-catalyzed amidation depending on the nature of ring B, using methods known to one skilled in the art for these types of couplings (see for example Yin & Buchwald *Organic Lett.* 2000, 2, 1101; Klapers et al. *JACS*, 2001, 123, 7727; Klapars et al. *JACS*, 2002, 124, 7421; Yin & Buchwald *JACS*. 2002, 124, 6043; Kiyomor, Madoux & Buchwald, *Tet. Lett.*, 1999, 40, 2657, Surry and Buchwald *Angew. Chem. Int. Ed.*, 2008, 47, 6338). Subsequent palladium-catalyzed amination of 1c to a suitably substituted amine 1d can provide compound 1e. Other methods for forming this bond can be found in the literature and can used by those skilled in the art. (Surry & Buchwald Chem Sci. 2011; 2(1): 27-50; Shaughnessy, Ciganek & DeVasher, *Organic Reactions*. 2014, 85:1:1-668). Removal of the protecting group from 1e, followed by condensation of the resulting free amine with a suitably substituted phenyl isocyanate, 1g or phenylcarbamate 1h can provide ureas 1f. Suitable isocyanates or 4-nitrophenylcarbamates are either commercially available or can be readily obtained from the corresponding aniline by methods known to one skilled in the art. Alternately, the ureas 1f can be obtained by treatment of the deprotected 3-aminopiperidinone intermediate with 4-nitrophenylchloroformate to form the carbamate, followed by condensation with an appropriately substituted aniline 1j. It will also be recognized by one skilled in the art that additional compounds of this invention wherein rings A and B are heteroaryl rings, such as pyridine, pyrimidine, thiazole, etc., can also be prepared using the methods outlined in Scheme 1 by substituting the appropriate heteroaryl iodide or bromine for 1b and heteroaryl amine, isocyanate or p-nitrophenylcarbamate for 1e.

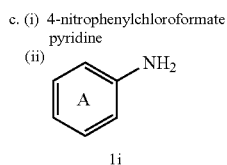

Alternatively as described in Scheme 2, compounds of this invention can be prepared from intermediate 1c by first deprotecting the amine and forming the urea linkage to ring A using the conditions described above for the conversion of 1e to 1f to provide compounds 2a. Compound 2a can then be coupled with amine under Pd-catalysis or Cu-catalysis conditions as shown in Scheme 1 for the transformation of 1c to 1e.

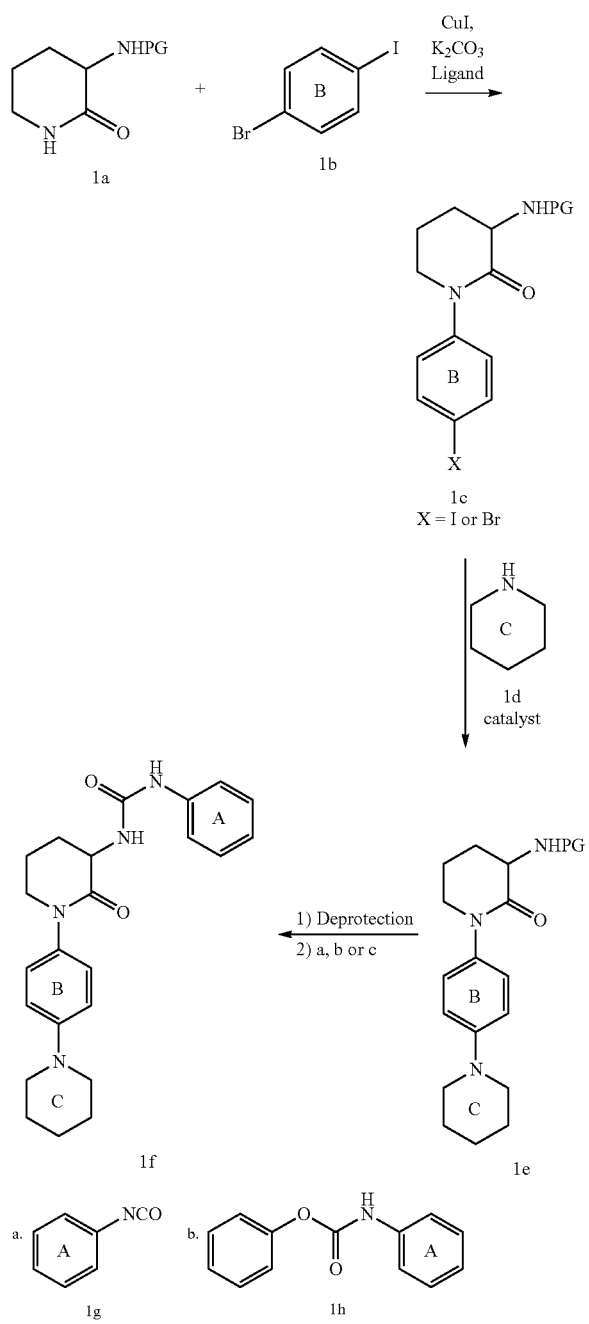

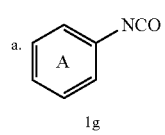

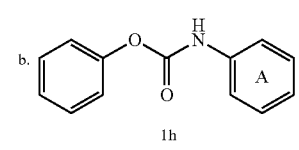

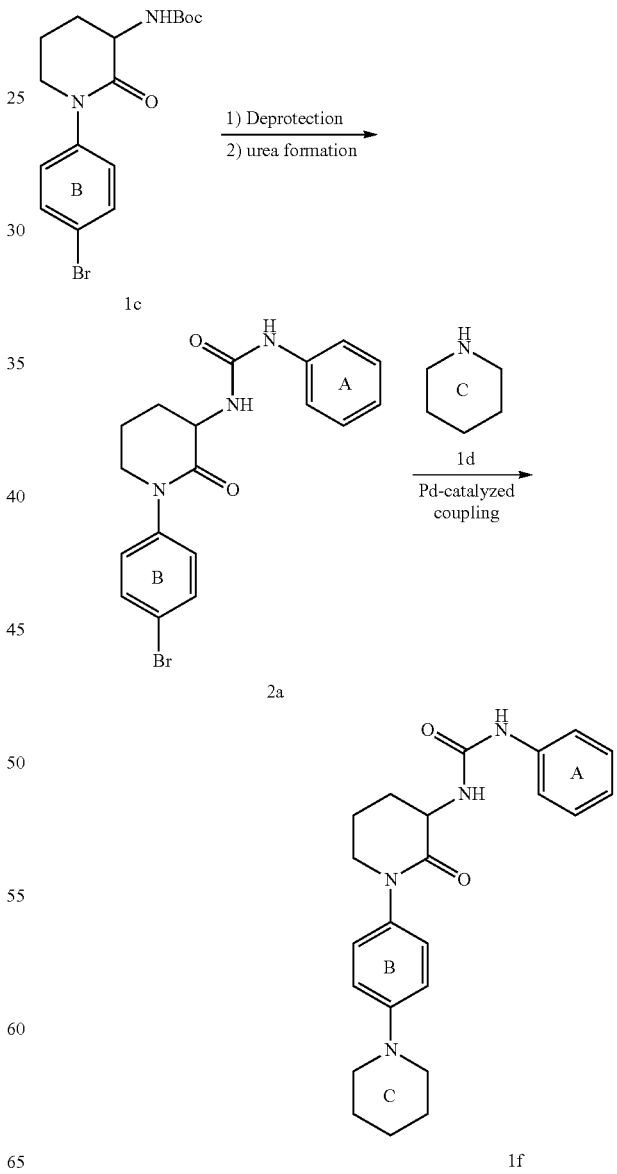

Additionally, compounds of this invention can be prepared from intermediate 2a by conversion to boronate 3b using palladium-catalyzed borylation according to the method of Suzuki and Miyaura followed by coupling of the resulting pinacolatoboron species with an amine copper catalyzed Chan-Lam coupling to provide compounds 1f (*J. Org. Chem.*, 2016, 81 (9), pp 3942-3950).

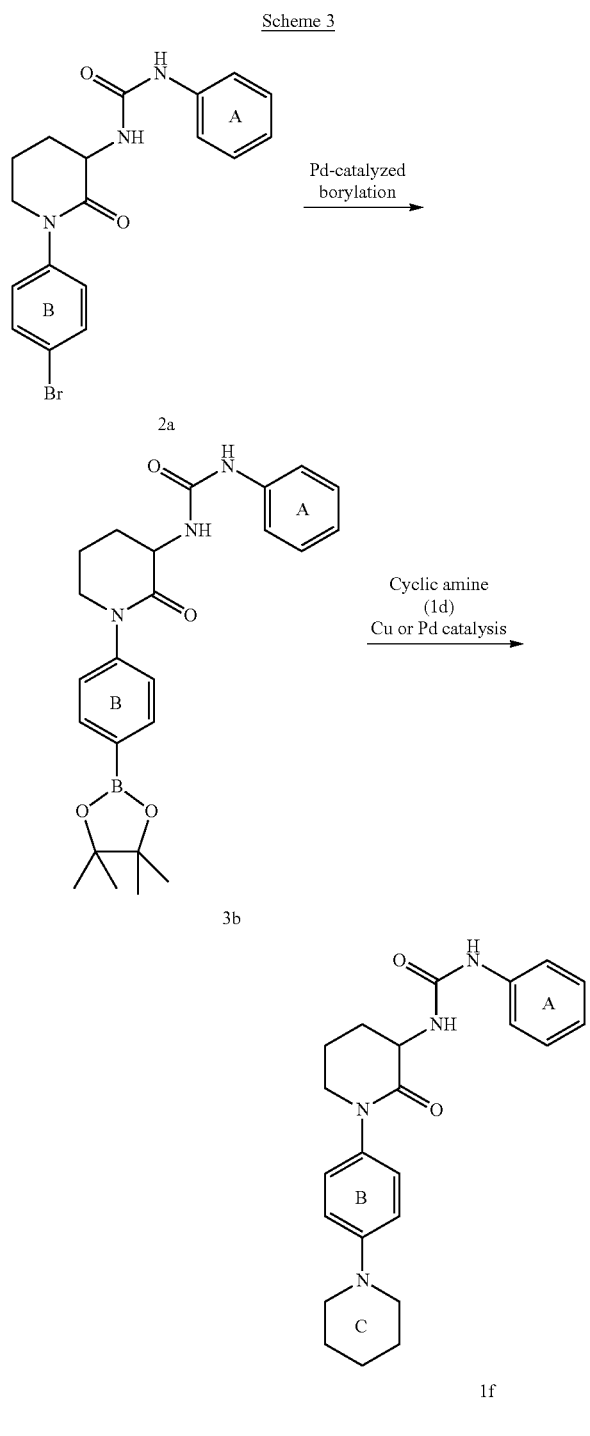

Alternatively, compounds of this invention can be prepared from intermediate 4b by nucleophilic displacement of the arylfluoride with cyclic amines (1d) to form intermediate 4c. Deprotection and installation of the urea, as shown in the above Schemes, results in the synthesis of some compounds described by this invention.

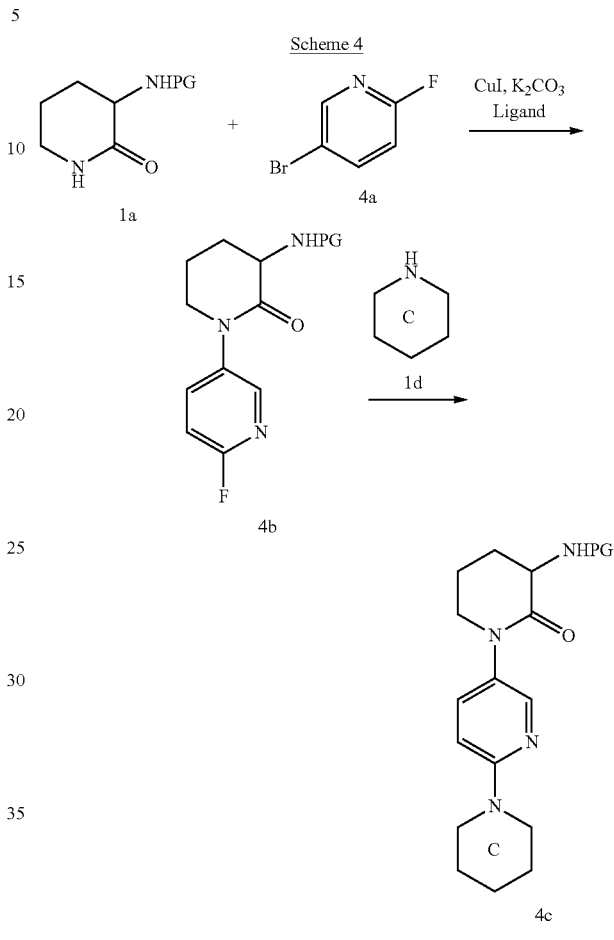

Even though rings A and B are shown as phenyl and C is shown as piperidine in Schemes 1-4, those skilled in the art can use analogous chemistry to make other compounds claimed in this patent. For example, the chemistry for introducing Ring C can also used with other cyclic amines.

Other features of the invention will become apparent in the course of the following descriptions of exemplary embodiments that are given for illustration of the invention and are not intended to be limiting thereof.

The following methods were used in the exemplified Examples, except where noted otherwise. Purification of intermediates and final products was carried out via either normal or reverse phase chromatography. Normal phase chromatography was carried out using pre-packed $SiO_2$ cartridges eluting with either gradients of hexanes and EtOAc or DCM and MeOH unless otherwise indicated. Reverse phase preparative HPLC was carried out using C18 columns eluting with gradients of Solvent A (10 mM ammonium acetate in water) and Solvent B (ACN, UV 220 nm) or with gradients of Solvent A (10 mM ammonium acetate in water) and Solvent B (MeOH, UV 220 nm) or with gradients of Solvent A (0.1% TFA in water) and Solvent B (ACN, UV 220 nm) (or) SunFire Prep C18 OBD 5μ. 19×150 mm, 25 min gradient from 0-100% B. A=10 mM ammonium acetate in water. B=ACN/MeOH (or) Waters XBridge C18, 19×1500 mm, 5-μm particles; A=10 mM ammonium acetate in water. B=ACN/MeOH; Gradient: 0-100% B over 25 minutes, then a 5-minute hold at 100% B; Flow: 15 mL/min.

Unless otherwise stated, analysis of final products was carried out by reverse phase analytical HPLC.

Method A: SunFire C18 column (3.5 μm C18, 3.0×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method B: XBridge Phenyl column (3.5 μm C18, 3.0×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method C: Ascentis Express C18, 2.1×50 mm, 2.7-μm particles; Solvent A: 95% water, 5% acetonitrile, 0.05% TFA; Solvent B: 95% acetonitrile, 5% water, 0.1% TFA; Temperature: 50° C.; Gradient: 0-100% B over 4 minutes, then a 1-minute hold at 100% B; Flow: 1.1 mL/min.

Method D: Ascentis Express C18, 2.1×50 mm, 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 4 minutes, then a 1-minute hold at 100% B; Flow: 1.1 mL/min.

Method E: Ascentis Express C18, 2.1×50 mm, 2.7-μm particles; Solvent A: 95% water, 5% acetonitrile, 0.05% TFA; Solvent B: 95% acetonitrile, 5% water, 0.1% TFA; Temperature: 50° C.; Gradient: 0-100% B over 3 minutes, then a 1-minute hold at 100% B; Flow: 1.1 mL/min.

Method F: Ascentis Express C18, 2.1×50 mm, 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 3 minutes, then a 1-minute hold at 100% B; Flow: 1.1 mL/min.

Method G: SunFire C18 column (3.5 μm C18, 3.0×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method H: XBridge Phenyl column (3.5 μm C18, 3.0×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method I: SunFire C18 column (3.5 μm, 4.6×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method J: XBridge Phenyl column (3.5 μm, 4.6×150 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method K: SunFire C18 column (3.5 μm, 4.6×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method L: XBridge Phenyl column (3.5 μm, 4.6×150 mm). Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method M: SunFire C18 column (3.5 μm, 4.6×150 mm). Gradient elution (1.0 mL/min) from 10-100% Solvent B over 18 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method N: XBridge Phenyl column (3.5 μm, 4.6×150 mm). Gradient elution (1.0 mL/min) from 10-100% Solvent B over 18 min and then 100% Solvent B for 5 min was used. Solvent A is 95% water, 5% acetonitrile, 0.05% TFA and Solvent B is 5% water, 95% acetonitrile, 0.05% TFA, UV 220 nm.

SFC and Chiral Purity Methods

Method I: Chiralpak AD-H, 250×4.6 mm, 5.0-μm particles; % $CO_2$: 60%, % Co solvent: 40% {0.2% DEA IN IPA:ACN (1:1)}, Total Flow: 4.0 g/min, Back Pressure: 100 bars, Temperature: 25° C., UV: 218 nm.

Method II: Chiralpak OD-H, 250×4.6 mm, 5.0-μm particles; % $CO_2$: 60%, % Co solvent: 40% {0.2% DEA IN IPA:ACN (1:1)}, Total Flow: 4.0 g/min, Back Pressure: 104 bars, Temperature: 24.9° C., UV: 287 nm.

Method III: Chiralpak OJ-H, 250×4.6 mm, 5.0-μm particles; % $CO_2$: 60%, % Co-solvent: 30%(0.3% DEA in Methanol), Total Flow: 4.0 g/min, Back Pressure: 101 bars, Temperature: 23.6° C., UV: 272 nm.

Method IV: Chiralpak AS-H, 250×4.6 mm, 5.0-μm particles; % $CO_2$: 60%, % Co-solvent: 40%(0.3% DEA in Methanol), Total Flow: 4.0 g/min, Back Pressure: 102 bars, Temperature: 25.4° C., UV: 272 nm.

Method V: Chiralcel OJ-H, 250×4.6 mm, 5.0-μm particles; % $CO_2$: 60%, % Co-solvent: 40%(0.2% DEA in Methanol), Total Flow: 4.0 g/min, Back Pressure: 102 bars, Temperature: 24.6° C., UV: 272 nm.

Method VI: Luxcellulose-2, 250×4.6 mm, 5.0-μm particles; % $CO_2$: 60%, % Co-solvent: 35%(0.2% DEA in Methanol), Total Flow: 3.0 g/min, Back Pressure: 101 bars, Temperature: 23.6° C., UV: 260 nm.

Method VII: Chiralcel AS-H, 250×4.6 mm, 5.0-μm particles; % $CO_2$: 60%, % Co-solvent: 40%(0.2% DEA in Methanol), Total Flow: 4.0 g/min, Back Pressure: 101 bars, Temperature: 24.4° C., UV: 270 nm.

Method VIII: Chiralpak IC, 250×4.6 mm, 5.0-μm particles; % $CO_2$: 60%, % Co-solvent: 40%(0.2% DEA in Methanol), Total Flow: 4.0 g/min, Back Pressure: 101 bars, Temperature: 24.4° C., UV: 270 nm.

Method IX: COLUMN: chiralpak IF (250×4.6 mm), 5 micron, MOBILE PHASE: −0.2% DEA in ETHANOL, FLOW: 1.0 ml/min.

Method X: COLUMN: LUX AMYLOSE 2 (250×4.6 mm), 5 micron, MOBILE PHASE: 0.2% DEA in n-HEXANE:ETHANOL:5:95, FLOW: 1.0 ml/min.

Method XI: COLUMN: CHIRALCEL OD-H (250×4.6 mm), 5 micron, MOBILE PHASE: −0.2% DEA in n-HEXANE:ETHANOL:70:30, FLOW: 1.0 ml/min.

Method XII: COLUMN: CHIRAL PAK ID 250×4.6 mm), 5 micron, MOBILE PHASE: −0.1% DEA in METHANOL, FLOW: 1.0 ml/min.

NMR Employed in Characterization of Examples. 1H NMR spectra were obtained with Bruker or JEOL® Fourier transform spectrometers operating at frequencies as follows: 1H NMR: 400 MHz (Bruker or JEOL®) or 500 MHz (Bruker or JEOL®). $^{13}$C NMR: 100 MHz (Bruker or JEOL®). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in 1H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Intermediate 1: tert-butyl (R)-(1-(4-bromophenyl)-2-oxopiperidin-3-yl)carbamate

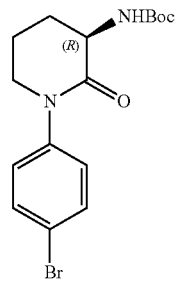

In a 1 L sealed tube, to a solution of (R)-tert-butyl (2-oxopiperidin-3-yl)carbamate (23 g, 110 mmol) in 1,4-dioxane (300 mL) was added 1,4-dibromobenzene (28 g, 120 mmol), potassium phosphate tribasic (34 g, 160 mmol), cuprous iodide (8.2 g, 43 mmol), N,N'-dimethylethylenediamine (4.7 ml, 43 mmol). The reaction mixture was purged with Argon for 10-15 minutes and then heated to 60° C. for overnight. The reaction mixture was diluted with ethyl acetate (250 mL) and washed with brine solution (200 mL). The organic layer was dried over $Na_2SO_4$ and concentrated to produce the crude product. The crude compound was purified through 330 g Silica column and was eluted with ethylacetate:pet-ether (40:60) to achieve off white solids of tert-butyl (1-(4-bromophenyl)-2-oxopiperidin-3-yl)carbamate (20 g). Chiral SFC analysis of the purified product showed ~10% epimerization. The compound was then purified via SFC to afford Intermediate 1 (15 g, 40 mmol, 38% yield) as a white solid. MS(ESI) m/z: 369.0/371.0 (M+H). $^1$H NMR (400 MHz, $CDCl_3$): □ ppm 7.48 (d, J=4.8 Hz, 2H), 7.11 (d, J=4.8 Hz, 2H), 5.48 (br-s, 1H), 4.25-4.18 (m, 1H), 3.70-3.62 (m, 2H), 2.60-2.52 (m, 1H), 2.08-1.95 (m, 2H), 1.74-1.64 (m, 1H), 1.43 (s, 9H). $[\alpha]_D^{25}$ (c=0.1, MeOH): +30.0. Chiral Purity (SFC): 99.9%, retention time=4.15 min (time of Peak-01 (0.105%)=3.03 min & Retention time of Peak-02 (99.9%)=4.15 min; Co-Solvent: 0.2% DEA in Methanol; Column: Whelk-01 (R,R)(250×4.6) mm 5u; Column Temperature: 24.5; Total Flow: 3; CO2 Flow Rate: 1.8; Co-Solvent Flow Rate: 1.2; Co-Solvent % 40; Back Pressure 100.)

Preparative SFC Conditions: Column/dimensions: Whelk (R,R) (250×30) mm, 5u; $CO_2$%: 70%; Co-solvent %: 30% of (0.2% DEA in methanol); Total Flow: 120 g/min; Back Pressure: 100 bar; Temperature: 30° C.; UV: 240 nm. Retention time of Peak-01=3.20 min & Retention time of Peak-02=4.60 min.

Intermediate 2: tert-butyl (R)-(1-(4-bromo-2-fluorophenyl)-2-oxopiperidin-3-yl)carbamate

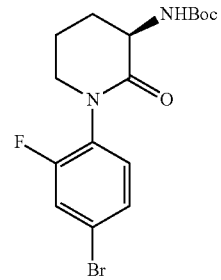

Intermediate 3: tert-butyl (R)-(1-(3-fluoro-4-iodophenyl)-2-oxopiperidin-3-yl)carbamate

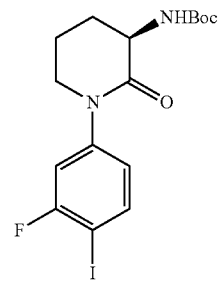

Cuprous iodide (3.6 g, 18 mmol) was added to a mixture of tert-butyl (R)-(2-oxopiperidin-3-yl)carbamate (10 g, 47 mmol), 4-bromo-2-fluoro-1-iodobenzene (14 g, 47 mmol), and potassium phosphate tribasic (15 g, 70 mmol) in dioxane (100 mL), and the mixture was purged with nitrogen for 20 minutes. N,N'-dimethylethylenediamine (2.0 mL, 18.7 mmol) was added, and the reaction mixture was stirred at 90° C. overnight. The reaction mixture was filtered through celite, washed with ethyl acetate and concentrated in vacuo. The crude product was purified by column chromatography (30% ethyl acetate in pet ether). The mixture was further purified by SFC to give tert-butyl (R)-(1-(4-bromo-2-fluorophenyl)-2-oxopiperidin-3-yl)carbamate (3.0 g, 7.8 mmol, 17% yield) and tert-butyl (R)-(1-(3-fluoro-4-iodophenyl)-2-oxopiperidin-3-yl)carbamate (1.8 g, 4.1 mmol, 8.8% yield). Analytical data for Intermediate 2: $^1$H NMR (300 MHz, $CDCl_3$): □ ppm 7.30-7.37 (m, 2H), 7.10-7.18 (m, 1H), 5.46 (s, 1H), 4.27 (m, 1H), 3.53-3.68 (m, 2H), 2.54-2.66 (m, 1H), 2.01-2.12 (m, 2H), 1.46 (s, 9H); $^{19}$FNMR: −117, MS(ESI) m/z: 387.2/389.2 (M+H)$^+$. Analytical data for Intermediate 3: $^1$H NMR (300 MHz, $CDCl_3$-d) □ ppm 7.49-7.00 (m, 2H), 6.92-7.00 (m, 1H), 5.46 (s, 1H), 4.27 (dt, J=11.71, 6.00 Hz, 1H), 3.54-3.68 (m, 2H), 2.54-2.66 (m, 1H), 2.01-2.12 (m, 2H), 1.74 (m, 1H), 1.46 (s, 9H); $^{19}$F NMR: −117, MS(ESI) m/z: 435.0 (M+H)$^+$.

Example 1: 1-(1-(4-((R)-3-Hydroxypyrrolidin-1-yl)phenyl)-2-oxopiperidin-3-yl)-3-(4-(trifluoromethyl)phenyl)urea

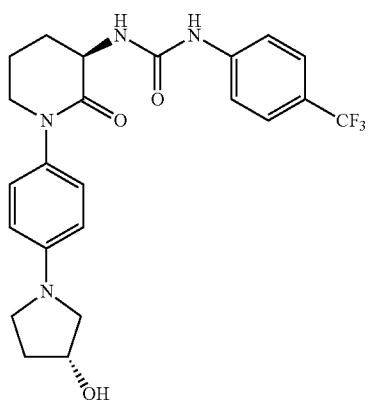 [SMILES: O=C(Nc1ccc(C(F)(F)F)cc1)N[C@@H]1CCCN(c2ccc(N3CC[C@@H](O)C3)cc2)C1=O]

Example 1A: tert-Butyl (1-(4-((R)-3-hydroxypyrrolidin-1-yl)phenyl)-2-oxopiperidin-3-yl)carbamate

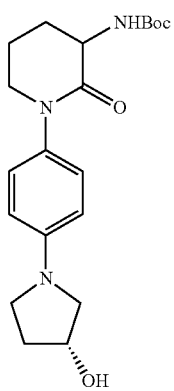 [SMILES: CC(C)(C)OC(=O)NC1CCCN(c2ccc(N3CC[C@@H](O)C3)cc2)C1=O]

(R)-pyrrolidin-3-ol (0.24 g, 2.7 mmol), and $Cs_2CO_3$ (1.8 g, 5.4 mmol) were added to a stirred solution of tert-butyl (R)-(1-(4-bromophenyl)-2-oxopiperidin-3-yl)carbamate (1.0 g, 2.7 mmol)) in toluene (10 mL). The reaction mixture was purged with nitrogen for 5 min and charged with $Pd(OAc)_2$ (0.061 g, 0.27 mmol) and 2-dicyclohexylphosphino-2′,6′-dipropoxy-1,1′-biphenyl (0.25 g, 0.54 mmol). The reaction mixture was again purged with nitrogen for 3 min and heated to 100° C. for 16 h. The reaction mixture was cooled, filtered through celite, and the filtrate was concentrated under reduced pressure. The crude mixture was purified using column chromatography to afford tert-butyl (1-(4-((R)-3-hydroxypyrrolidin-1-yl)phenyl)-2-oxopiperidin-3-yl)carbamate (250 mg, 0.66 mmol, 25% yield) as a pale yellow solid. MS(ESI) m/z: 376.2 $(M+H)^+$.

Example 1B: 3-Amino-1-(4-((R)-3-hydroxypyrrolidin-1-yl)phenyl)piperidin-2-one hydrochloride

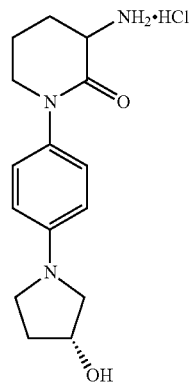

4N HCl in 1,4-dioxane (1.7 mL, 6.7 mmol) was added to an ice cooled solution of tert-butyl (1-(4-((R)-3-hydroxypyrrolidin-1-yl)phenyl)-2-oxopiperidin-3-yl)carbamate (0.25 g, 0.67 mmol) in 1,4-dioxane (1 mL), and the mixture was stirred at rt for two hours. The solvent was evaporated under reduced pressure to obtain a gummy solid. The solid was triturated with diethyl ether (2×20 mL) and dried to afford 3-amino-1-(4-((R)-3-hydroxypyrrolidin-1-yl)phenyl)piperidin-2-one hydrochloride (0.20 g, 0.64 mmol, 96% yield) as a off white solid. MS(ESI) m/z: 275.9 $(M+H)^+$.

Example 1: To an ice cooled solution of 3-amino-1-(4-((R)-3-hydroxypyrrolidin-1-yl)phenyl)piperidin-2-one hydrochloride (0.20 g, 0.64 mmol) in DMSO (1 mL) under nitrogen, were added $K_2CO_3$ (0.052 mL, 0.37 mmol) and phenyl (4-(trifluoromethyl)phenyl)carbamate (0.20 g, 0.71 mmol). The reaction mixture was gradually warmed to rt and stirred for 15 hours. The reaction mixture was filtered through syringe filter, and concentrated under reduced pressure. The crude mixture was purified by reverse phase chromatography followed by chiral HPLC to afford Example 1 (6 mg, 0.013 mmol, 2.71%). MS(ESI) m/z: 463.2 $(M+H)^+$; $^1H$ NMR (400 MHz, DMSO-d6): δ 9.19 (s, 1H), 7.70-7.47 (m, 4H), 7.13-6.98 (m, J=9.0 Hz, 2H), 6.66 (d, J=6.4 Hz, 1H), 6.56-6.41 (m, J=9.0 Hz, 2H), 4.94 (d, J=3.4 Hz, 1H), 4.39 (br. s., 1H), 4.30-4.21 (m, 1H), 3.58 (t, J=6.1 Hz, 2H), 3.42-3.38 (m, 2H), 3.26 (dd, J=8.3, 3.4 Hz, 1H), 3.05 (d, J=10.5 Hz, 1H), 2.30 (d, J=5.9 Hz, 1H), 2.09-1.83 (m, 4H), 1.79-1.68 (m, 1H). RT=1.56 min, 98.7% (Method F); chiral purity determined by chiral SFC analysis (method IV).

Additional examples of compounds of this invention shown in Table 1 were prepared using combinations of the procedures described in Example 1 or modifications thereof known to one skilled in the art of organic synthesis.

| Ex | Structure and Name | LCMS (M + H)+ | HPLC Method, RT (min) & Purity | ¹H NMR |
|---|---|---|---|---|
| 2 | 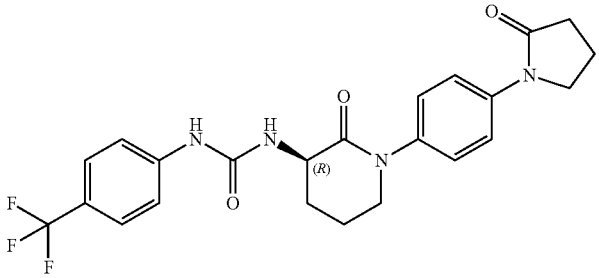<br>(R)-1-(2-oxo-1-(4-(2-oxopyrrolidin-1-yl)phenyl)piperidin-3-yl)-3-(4-(trifluoromethyl)phenyl)urea | 461.2 | Method F, RT = 1.53 min, 99.8% | ¹H NMR (400 MHz, DMSO-d₆): δ 9.19 (s, 1H), 7.71-7.62 (m, J = 9.0 Hz, 2H), 7.61-7.51 (m, 4H), 7.36-7.20 (m, J = 8.8 Hz, 2H), 6.66 (d, J = 6.8 Hz, 1H), 4.36-4.27 (m, 1H), 3.83 (t, J = 7.0 Hz, 2H), 3.71-3.60 (m, 2H), 2.55-2.46 (m, 1H), 2.29 (dd, J = 12.7, 5.9 Hz, 1H), 2.10-2.02 (m, 3H), 2.01-1.93 (m, 2H), 1.81-1.65 (m, 1H). |
| 3 | 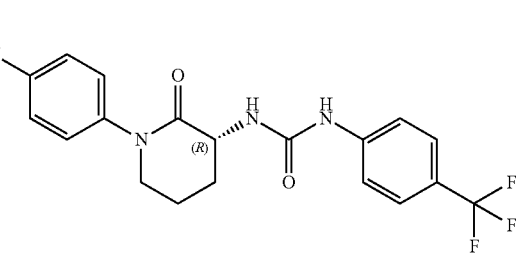<br>1-((R)-1-(4-((S)-3-hydroxypyrrolidin-1-yl)phenyl)-2-oxopiperidin-3-yl)-3-(4-(trifluoromethyl)phenyl)urea | 463.2 | Method F, RT = 1.56 min, 96.2% | ¹H NMR (400 MHz, DMSO-d₆): δ 9.19 (s, 1H), 7.68-7.49 (m, 4H), 7.14-6.96 (m, J = 8.8 Hz, 2H), 6.66 (d, J = 6.1 Hz, 1H), 6.56-6.39 (m, J = 8.8 Hz, 2H), 4.93 (br. s., 1H), 4.39 (br. s., 1H), 4.32-4.18 (m, 1H), 3.58 (t, J = 6.2 Hz, 2H), 3.45-3.38 (m, 2H), 3.28-3.22 (m, 1H), 3.06 (d, J = 9.0 Hz, 1H), 2.33-2.22 (m, 1H), 2.10-1.82 (m, 4H), 1.81-1.65 (m, 1H). |
| 4 | 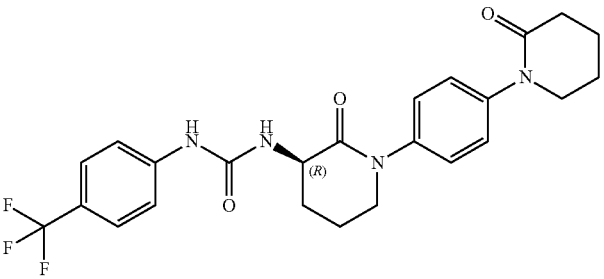<br>(R)-1-(2-oxo-1-(4-(2-oxopiperidin-1-yl)phenyl)piperidin-3-yl)-3-(4-(trifluoromethyl)phenyl)urea | 475.2 | Method F, RT = 1.52 min, 95.7% | ¹H NMR (400 MHz, DMSO-d₆): δ 9.21 (s, 1H), 7.67-7.49 (m, 4H), 7.36-7.19 (m, 4H), 6.67 (d, J = 6.4 Hz, 1H), 4.39-4.28 (m, 1H), 3.68 (dq, J = 12.0, 5.9 Hz, 2H), 3.60 (t, J = 5.6 Hz, 2H), 2.39 (t, J = 6.1 Hz, 2H), 2.33-2.25 (m, 1H), 2.06-1.94 (m, 2H), 1.91-1.75 (m, 5H) |
| 5 | 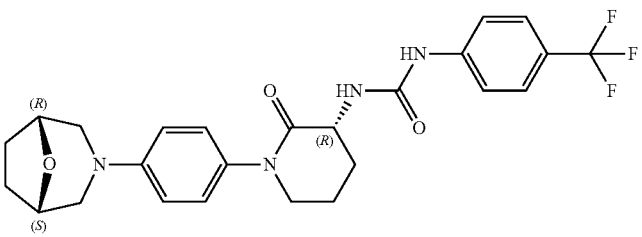<br>1-((R)-1-(4-((1R,5S)-8-oxa-3-azabicyclo[3.2.1]octan-3-yl)phenyl)-2-oxopiperidin-3-yl)-3-(4-(trifluoromethyl)phenyl)urea | 489.2 | Method F, RT = 1.71 min, 100.0% | ¹H NMR (400 MHz, DMSO-d₆): δ 9.18 (s, 1H), 7.67 - 7.48 (m, 4H), 7.08 (d, J = 8.6 Hz, 2H), 6.85 (d, J = 8.8 Hz, 2H), 6.64 (d, J = 6.6 Hz, 1H), 4.30-4.22 (m, 1H), 4.12 (br. s., 2H), 3.69 (d, J = 10.8 Hz, 2H), 3.58 (d, J = 6.8 Hz, 2H), 3.49-3.42 (m, 2H), 2.31-2.20 (m, 1H), 2.00-1.82 (m, 6H), 1.80-1.69 (m, 1H). |

| Ex | Structure and Name | LCMS (M + H)+ | HPLC Method, RT (min) & Purity | ¹H NMR |
|---|---|---|---|---|
| 6 | 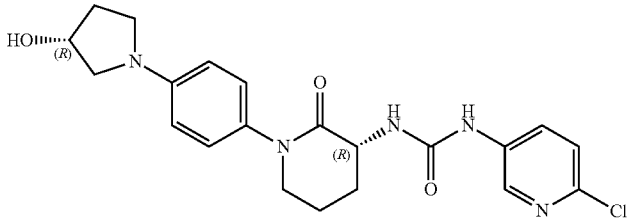<br>1-(6-chloropyridin-3-yl)-3-((R)-1-(4-((R)-3-hydroxypyrrolidin-1-yl)phenyl)-2-oxopiperidin-3-yl)urea | 430.2 | Method F, RT = 1.16 min, 100.0% | ¹H NMR (400 MHz, DMSO-$d_6$): δ 9.11 (s, 1H), 8.39 (d, J = 2.7 Hz, 1H), 7.92 (dd, J = 8.7, 2.8 Hz, 1H), 7.37 (d, J = 8.8 Hz, 1H), 7.04 (d, J = 8.8 Hz, 2H), 6.69 (d, J = 6.6 Hz, 1H), 6.42 (d, J = 8.8 Hz, 2H), 4.97 (d, J = 3.7 Hz, 1H), 4.39 (br. s., 1H), 4.29-4.22 (m, 1H), 3.58-3.56 (m, 2H), 3.31-3.27 (m, 2H), 3.05 (d, J = 9.5 Hz, 1H), 2.86-2.79 (m, 1H), 2.28 (dd, J = 11.9, 5.7 Hz, 1H), 2.08-1.83 (m, 4H), 1.79-1.66 (m, 1H) |
| 7 | 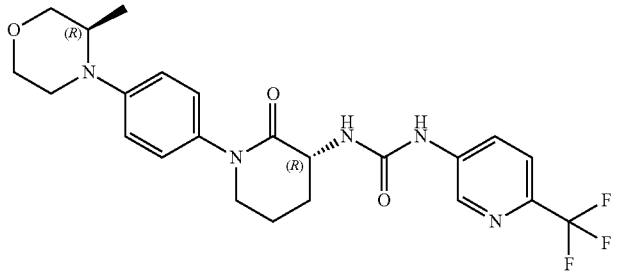<br>1-((R)-1-(4-((R)-3-methylmorpholino)phenyl)-2-oxopiperidin-3-yl)-3-(6-(trifluoromethyl)pyridin-3-yl)urea | 478.2 | Method F, RT = 1.49 min, 100.0% | ¹H NMR (400 MHz, DMSO-$d_6$): δ 9.44 (s, 1H), 8.68 (s, 1H), 8.15 (d, J = 6.8 Hz, 1H), 7.76 (d, J = 8.8 Hz, 1H), 7.13 (d, J = 8.3 Hz, 2H), 6.90 (d, J = 8.3 Hz, 2H), 6.82 (d, J = 6.8 Hz, 1H), 4.34-4.23 (m, 1H), 3.94-3.86 (m, 1H), 3.82 (br. s., 1H), 3.73-3.52 (m, 5H), 3.21-3.12 (m, 1H), 3.04-2.94 (m, 1H), 2.35-2.25 (m, 1H), 2.05-1.87 (m, 2H), 1.85-1.63 (m, 1H), 0.99 (d, J = 6.6 Hz, 3H). |
| 8 | 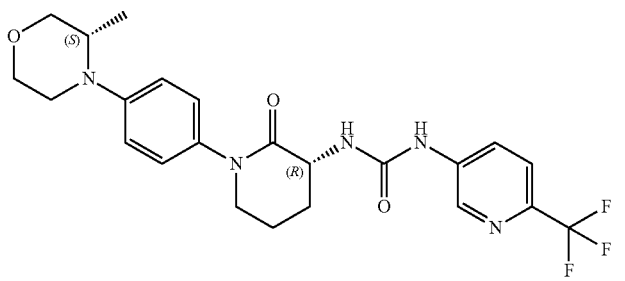<br>1-((R)-1-(4-((S)-3-methylmorpholino)phenyl)-2-oxopiperidin-3-yl)-3-(6-(trifluoromethyl)pyridin-3-yl)urea | 478.2 | Method F, RT = 1.49 min, 100.0% | ¹H NMR (400 MHz, DMSO-$d_6$) δ 9.44 (s, 1H), 8.67 (s, 1H), 8.14 (d, J = 8.3 Hz, 1H), 7.76 (d, J = 8.6 Hz, 1H), 7.10 (d, J = 8.8 Hz, 2H), 6.90 (d, J = 8.8 Hz, 2H), 6.82 (d, J = 6.6 Hz, 1H), 4.34-4.22 (m, 1H), 3.90 (d, J = 12.0 Hz, 1H), 3.83 (d, J = 6.4 Hz, 1H), 3.72-3.51 (m, 5H), 3.16 (d, J = 12.0 Hz, 1H), 3.02-2.94 (m, 1H), 2.31-2.22 (m, 1H), 2.03-1.89 (m, 2H), 1.84-1.71 (m, 1H), 0.99 (d, J = 6.4 Hz, 3H) |

| Ex | Structure and Name | LCMS (M + H)+ | HPLC Method, RT (min) & Purity | ¹H NMR |
|----|-------------------|---------------|-------------------------------|--------|
| 9 | (S)-1-(1-(4-(2-oxa-6-azaspiro[3.3]heptan-6-yl)phenyl)-2-oxopiperidin-3-yl)-3-(4-(trifluoromethyl)phenyl)urea | 475.2 | Method F, RT = 1.61 min, 100.0% | ¹H NMR (400 MHz, DMSO-d₆): δ 9.18 (s, 1H), 7.58 (s, 4H), 7.10 (d, J = 8.8 Hz, 2H), 6.64 (d, J = 6.8 Hz, 1H), 6.40 (d, J = 8.8 Hz, 2H), 4.71 (s, 4H), 4.26 (dd, J = 12.1, 6.0 Hz, 1H), 3.96 (s, 4H), 3.57-3.50 (m, 2H), 2.31-2.23 (m, 1H), 2.02-1.87 (m, 2H), 1.80-1.68 (m, 1H). |
| 10 | (R)-1-(1-(4-(2-oxa-6-azaspiro[3.3]heptan-6-yl)phenyl)-2-oxopiperidin-3-yl)-3-(4-(trifluoromethyl)phenyl)urea | 475.2 | Method F, RT = 1.61 min, 100.0% | ¹H NMR (400 MHz, DMSO-d₆): δ 9.18 (s, 1H), 7.68-7.48 (m, 4H), 7.07 (d, J = 8.3 Hz, 2H), 6.64 (d, J = 6.6 Hz, 1H), 6.42 (d, J = 8.3 Hz, 2H), 4.71 (s, 4H), 4.32-4.20 (m, 1H), 3.96 (s, 4H), 3.57 (t, J = 6.4 Hz, 2H), 2.29 (dd, J = 12.1, 5.7 Hz, 1H), 2.02-1.87 (m, 2H), 1.80-1.68 (m, 1H) |
| 11 | 1-((3R)-1-(4-(3-oxa-8-azabicyclo[3.2.1]octan-8-yl)phenyl)-2-oxopiperidin-3-yl)-3-(5-(trifluoromethyl)pyridin-2-yl)urea | 490.2 | Method F, RT = 1.62 min, 100.0% | ¹H NMR (400 MHz, DMSO-d₆): δ 9.79 (s, 1H), 8.55 (s, 1H), 8.09 (d, J = 6.6 Hz, 1H), 8.05 (dd, J = 8.9, 2.6 Hz, 1H), 7.72 (d, J = 9.0 Hz, 1H), 7.10 (d, J = 8.8 Hz, 2H), 6.83 (d, J = 9.0 Hz, 2H), 4.43-4.26 (m, 1H), 4.13 (br. s., 2H), 3.70 (d, J = 10.5 Hz, 2H), 3.66-3.56 (m, 2H), 3.44 (d, J = 10.5 Hz, 2H), 2.36-2.28 (m, 1H), 2.02-1.83 (m, 6H), 1.82-1.72 (m, 1H). |

-continued

| Ex | Structure and Name | LCMS (M + H)+ | HPLC Method, RT (min) & Purity | ¹H NMR |
|---|---|---|---|---|
| 12 | 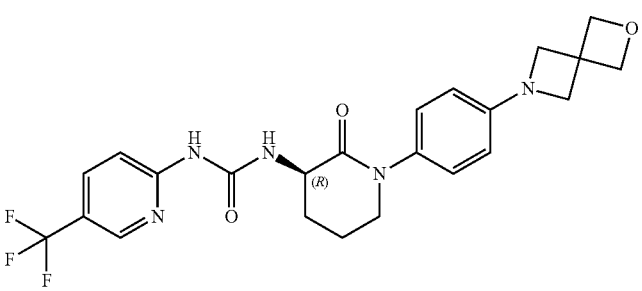<br>(R)-1-(1-(4-(2-oxa-6-azaspiro[3.3]heptan-6-yl)phenyl)-2-oxopiperidin-3-yl)-3-(5-(trifluoromethyl)pyridin-2-yl)urea | 476.2 | Method F, RT = 1.51 min, 100.0% | ¹H NMR (400 MHz, METHANOL-d₄): δ 9.77 (s, 1H), 8.62-8.44 (m, 1H), 8.10-8.02 (m, 2H), 7.73 (d, J = 9.0 Hz, 1H), 7.15-6.96 (m, 2H), 6.51-6.35 (m, 2H), 4.71 (s, 4H), 4.45-4.23 (m, 1H), 3.96 (s, 4H), 3.65-3.49 (m, 2H), 2.36-2.26 (m, 1H), 2.02-1.88 (m, 2H), 1.85-1.69 (m, 1H). |
| 13 | 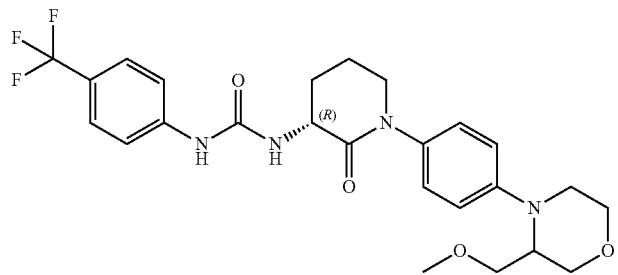<br>1-((3R)-1-(4-(3-(methoxymethyl)morpholino)phenyl)-2-oxopiperidin-3-yl)-3-(4-(trifluoromethyl)phenyl)urea | 507.2 | Method F, RT = 1.69 min, 100.0% | ¹H NMR (400 MHz, DMSO-d₆): δ 9.34 (s, 1H), 7.70-7.45 (m, 4H), 7.20-7.05 (m, J = 8.8 Hz, 2H), 6.96-6.83 (m, J = 9.0 Hz, 2H), 6.80 (d, J = 6.6 Hz, 1H), 4.36-4.18 (m, 1H), 4.00-3.85 (m, 2H), 3.81 (d, J = 8.6 Hz, 1H), 3.69-3.48 (m, 5H), 3.28-3.18 (m, 4H), 3.15 (dd, J = 8.9, 3.5 Hz, 1H), 2.99 (td, J = 11.9, 3.7 Hz, 1H), 2.32-2.20 (m, 1H), 2.04-1.86 (m, 2H), 1.84-1.72 (m, 1H). |
| 14 | 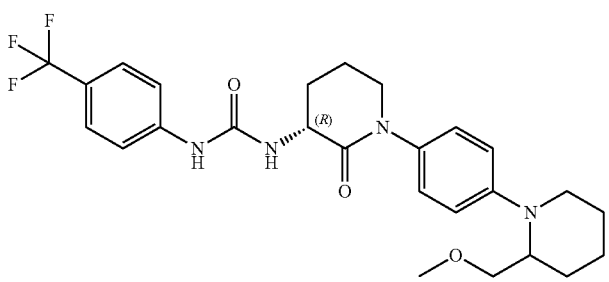<br>1-((3R)-1-(4-(2-(methoxymethyl)piperidin-1-yl)phenyl)-2-oxopiperidin-3-yl)-3-(4-(trifluoromethyl)phenyl)urea | 505.3 | Method F, RT = 1.99 min, 100.0% | ¹H NMR (400 MHz, DMSO-d₆): δ 9.20 (s, 1H), 7.66-7.51 (m, 4H), 7.08 (br. s., 2H), 6.89 (br. s., 2H), 6.65 (d, J = 6.4 Hz, 1H), 4.28 (dt, J = 11.5, 6.0 Hz, 1H), 3.96 (br. s., 1H), 3.61 (br. s., 2H), 3.50 (br. s., 1H), 3.29-3.24 (m, 2H), 3.22-3.16 (m, 3H), 2.97-2.85 (m, 1H), 2.32-2.23 (m, 1H), 2.04-1.89 (m, 2H), 1.86-1.50 (m, 7H). |

-continued

| Ex | Structure and Name | LCMS (M + H)+ | HPLC Method, RT (min) & Purity | ¹H NMR |
|---|---|---|---|---|
| 15 | 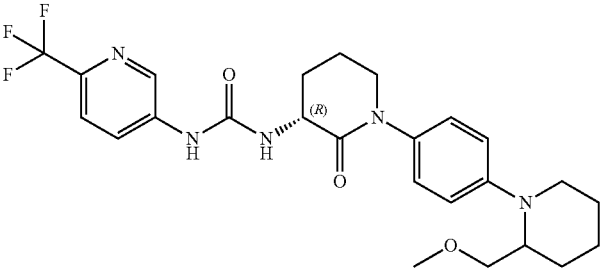<br>1-((3R)-1-(4-(2-(methoxymethyl)piperidin-1-yl)phenyl)-2-oxopiperidin-3-yl)-3-(6-(trifluoromethyl)pyridin-3-yl)urea | 506.3 | Method F, RT = 1.79 min, 100.0% | ¹H NMR (400 MHz, DMSO-$d_6$): δ 9.45 (s, 1H), 8.67 (d, J = 2.4 Hz, 1H), 8.15 (d, J = 8.3 Hz, 1H), 7.76 (d, J = 8.3 Hz, 1H), 7.10 (d, J = 8.8 Hz, 2H), 6.90 (d, J = 8.8 Hz, 2H), 6.82 (d, J = 6.8 Hz, 1H), 4.37-4.20 (m, 1H), 3.96 (br. s., 1H), 3.65-3.58 (m, 2H), 3.50 (s, 1H), 3.26 (d, J = 4.6 Hz, 1H), 3.20 (s, 3H), 2.95-2.86 (m, 1H), 2.83-2.74 (m, 1H), 2.32-2.23 (m, 1H), 2.00-1.91 (m, 2H), 1.85-1.73 (m, 2H), 1.79-1.45 (m, 5H). |
| 16 | 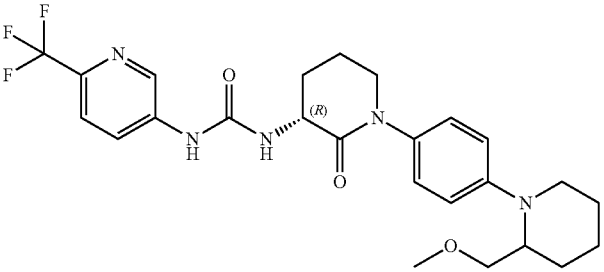<br>1-((3R)-1-(4-(2-(methoxymethyl)piperidin-1-yl)phenyl)-2-oxopiperidin-3-yl)-3-(6-(trifluoromethyl)pyridin-3-yl)urea | 506.2 | Method F, RT = 1.79 min, 100.0% | ¹H NMR (400 MHz, DMSO-$d_6$): δ 9.45 (s, 1H), 8.67 (d, J = 2.4 Hz, 1H), 8.23-8.04 (m, 1H), 7.76 (d, J = 8.8 Hz, 1H), 7.10 (d, J = 8.8 Hz, 2H), 6.90 (d, J = 8.8 Hz, 2H), 6.83 (d, J = 6.8 Hz, 1H), 4.34-4.24 (m, 1H), 3.96 (br. s., 1H), 3.60 (t, J = 6.2 Hz, 2H), 3.53-3.48 (m, 1H), 3.30-3.20 (m, 2H), 3.20 (s, 3H), 2.94-2.85 (m, 1H), 2.31-2.22 (m, 1H), 2.03-1.91 (m, 2H), 1.79 (br. s., 2H), 1.71-1.50 (m, 5H). |
| 17 | 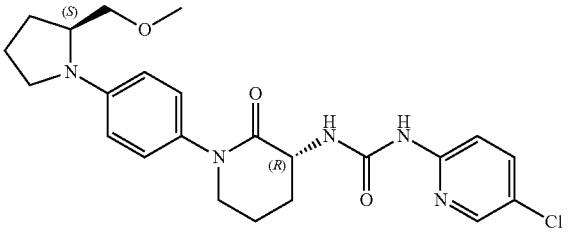<br>1-(5-chloropyridin-2-yl)-3-((R)-1-(4-((S)-2-(methoxymethyl)pyrrolidin-1-yl)phenyl)-2-oxopiperidin-3-yl)urea | 485.2 | Method F, RT = 1.61 min, 100.0% | ¹H NMR (400 MHz, DMSO-$d_6$): δ 9.12 (s, 1H), 8.40 (d, J = 2.8 Hz, 1H), 7.93 (dd, J = 8.8, 2.8 Hz, 1H), 7.37 (d, J = 8.8 Hz, 1H), 7.10 (d, J = 8.8 Hz, 2H), 6.69 (d, J = 6.6 Hz, 1H), 6.56 (d, J = 8.8 Hz, 2H), 4.34-4.17 (m, 1H), 3.81 (br. s., 1H), 3.57 (t, J = 6.2 Hz, 2H), 3.42-3.30 (m, 2H), 3.28 (s, 3H), 3.25-3.17 (m, 1H), 3.07-2.99 (m, 1H), 2.32-2.22 (m, 1H), 2.04-1.85 (m, 6H), 1.80-1.67 (m, 1H). |
| 18 | 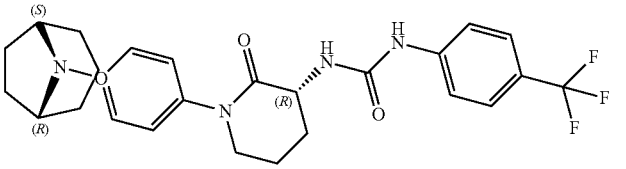<br>1-((R)-1-(4-((1R,5S)-3-oxa-8-azabicyclo[3.2.1]octan-8-yl)phenyl)-2-oxopiperidin-3-yl)-3-(4-(trifluoromethyl)phenyl)urea | 489.2 | Method F, RT = 1.71 min, 100.0% | ¹H NMR (400 MHz, DMSO-$d_6$): δ 9.19 (s, 1H), 7.67-7.47 (m, 4H), 7.10 (d, J = 9.0 Hz, 2H), 6.82 (d, J = 9.0 Hz, 2H), 6.64 (d, J = 6.8 Hz, 1H), 4.33-4.21 (m, 1H), 4.12 (br. s., 2H), 3.69 (d, J = 10.5 Hz, 2H), 3.63-3.58 (m, 2H), 3.52-3.39 (m, 2H), 2.32-2.23 (m, 1H), 2.02-1.80 (m, 6H), 1.79-1.69 (m, 1H). |

-continued

| Ex | Structure and Name | LCMS (M + H)+ | HPLC Method, RT (min) & Purity | ¹H NMR |
|---|---|---|---|---|
| 19 | 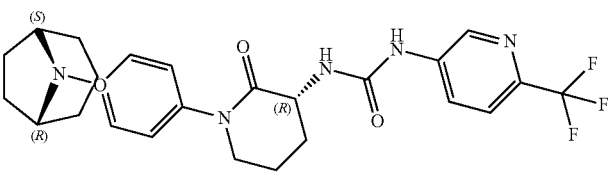<br>1-((R)-1-(4-((1R,5S)-3-oxa-8-azabicyclo[3.2.1]octan-8-yl)phenyl)-2-oxopiperidin-3-yl)-3-(6-(trifluoromethyl)pyridin-3-yl)urea | 490.2 | Method F, RT = 1.49 min, 100.0% | ¹H NMR (400 MHz, DMSO-d₆): δ 9.42 (s, 1H), 8.67 (d, J = 2.4 Hz, 1H), 8.19-8.07 (m, 1H), 7.76 (d, J = 8.8 Hz, 1H), 7.09 (d, J = 9.0 Hz, 2H), 6.89-6.74 (m, 3H), 4.32-4.25 (m, 1H), 4.12 (br. s., 2H), 3.73-3.66 (m, 2H), 3.62-3.59 (m, 4H), 2.31-2.23 (m, 1H), 2.00-1.77 (m, 7H). |
| 20 | 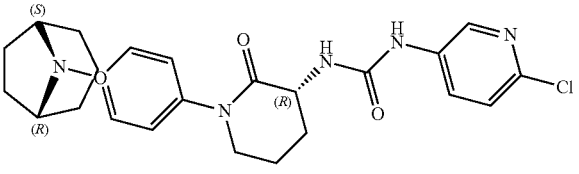<br>1-((R)-1-(4-((1R,5S)-3-oxa-8-azabicyclo[3.2.1]octan-8-yl)phenyl)-2-oxopiperidin-3-yl)-3-(6-chloropyridin-3-yl)urea | 456.2 | Method F, RT = 1.29 min, 100.0% | ¹H NMR (400 MHz, DMSO-d₆): δ 9.11 (s, 1H), 8.39 (d, J = 2.7 Hz, 1H), 7.91 (dd, J = 8.7, 2.8 Hz, 1H), 7.37 (d, J = 8.8 Hz, 1H), 7.10 (d, J = 9.0 Hz, 2H), 6.85 (d, J = 9.0 Hz, 2H), 6.68 (d, J = 6.8 Hz, 1H), 4.30-4.20 (m, 1H), 4.12 (br. s., 2H), 3.71-3.67 (m, 2H), 3.59-3.40 (m, 4H), 2.32-2.21 (m, 1H), 2.00-1.81 (m, 6H), 1.80-1.69 (m, 1H). |
| 21 | 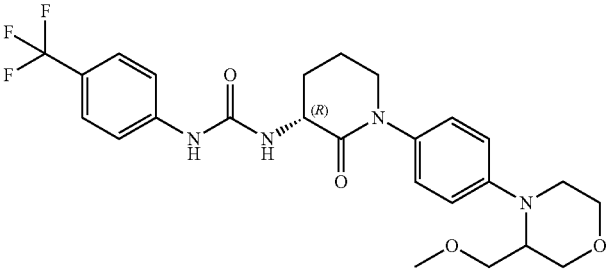<br>1-((3R)-1-(4-(3-(methoxymethyl)morpholino)phenyl)-2-oxopiperidin-3-yl)-3-(4-(trifluoromethyl)phenyl)urea | 507.2 | Method F, RT = 1.69 min, 100.0% | ¹H NMR (400 MHz, DMSO-d₆): δ 9.20 (s, 1H), 7.71-7.49 (m, 4H), 7.12 (d, J = 9.0 Hz, 2H), 6.86 (d, J = 9.0 Hz, 2H), 6.66 (d, J = 6.6 Hz, 1H), 4.38-4.18 (m, 1H), 4.00-3.86 (m, 2H), 3.80 (d, J = 8.6 Hz, 1H), 3.67-3.58 (m, 5H), 3.57-3.49 (m, 1H), 3.25 (s, 3H), 3.20-3.11 (m, 1H), 3.00 (td, J = 12.0, 3.5 Hz, 1H), 2.33-2.23 (m, 1H), 2.04-1.87 (m, 2H), 1.83-1.66 (m, 1H). |
| 22 | 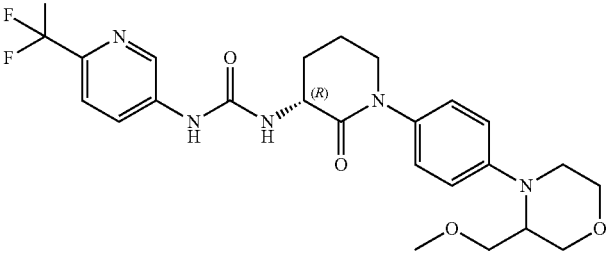<br>1-((3R)-1-(4-(3-(methoxymethyl)morpholino)phenyl)-2-oxopiperidin-3-yl)-3-(6-(trifluoromethyl)pyridin-3-yl)urea | 508.2 | Method F, RT = 1.49 min, 100.0% | ¹H NMR (400 MHz, DMSO-d₆): δ 9.65 (s, 1H), 8.69 (d, J = 2.2 Hz, 1H), 8.15 (d, J = 8.1 Hz, 1H), 7.76 (d, J = 8.8 Hz, 1H), 7.41-7.29 (m, 1H), 7.13 (d, J = 9.0 Hz, 2H), 7.02 (d, J = 6.4 Hz, 1H), 6.89 (d, J = 9.0 Hz, 2H), 4.39-4.21 (m, 1H), 3.98-3.85 (m, 2H), 3.79 (br. s., 1H), 3.69-3.50 (m, 5H), 3.27-3.17 (m, 1H), 3.18 (s, 3H), 3.19-3.12 (m, 1H), 3.06-2.94 (m, 1H), 2.31-2.25 (m, 1H), 1.99-1.93 (m, 2H), 1.86-1.68 (m, 1H). |

-continued

| Ex | Structure and Name | LCMS (M + H)+ | HPLC Method, RT (min) & Purity | ¹H NMR |
|---|---|---|---|---|
| 23 | 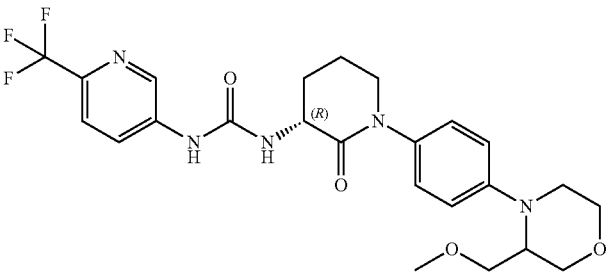<br>1-((3R)-1-(4-(3-(methoxymethyl)morpholino)phenyl)-2-oxopiperidin-3-yl)-3-(6-(trifluoromethyl)pyridin-3-yl)urea | 508.2 | Method F, RT = 1.50 min, 100.0% | ¹H NMR (400 MHz, DMSO-d₆): δ 9.45 (s, 1H), 8.67 (d, J = 2.1 Hz, 1H), 8.15 (dd, J = 8.7, 2.1 Hz, 1H), 7.76 (d, J = 8.8 Hz, 1H), 7.10 (d, J = 9.0 Hz, 2H), 6.89 (d, J = 9.0 Hz, 2H), 6.82 (d, J = 6.6 Hz, 1H), 4.38-4.20 (m, 1H), 4.01-3.86 (m, 2H), 3.81 (d, J = 8.6 Hz, 1H), 3.69-3.58 (m, 4H), 3.57-3.47 (m, 1H), 3.27-3.19 (m, 4H), 3.17 (dd, J = 9.0, 3.7 Hz, 1H), 3.00 (td, J = 11.9, 3.8 Hz, 1H), 2.32-2.21 (m, 1H), 2.05-1.88 (m, 2H), 1.86-1.69 (m, 1H). |
| 24 | 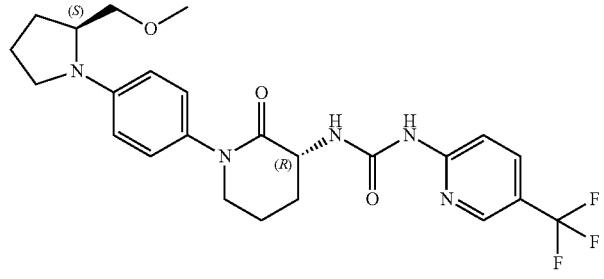<br>1-((R)-1-(4-((S)-2-(methoxymethyl)pyrrolidin-1-yl)phenyl)-2-oxopiperidin-3-yl)-3-(5-(trifluoromethyl)pyridin-2-yl)urea | 492.3 | Method F, RT = 1.89 min, 99.0% | ¹H NMR (400 MHz, DMSO-d₆): δ 9.78 (s, 1H), 8.55 (s, 1H), 8.05 (dd, J = 9.0, 2.4 Hz, 2H), 7.74 (d, J = 9.0 Hz, 1H), 7.10 (d, J = 8.8 Hz, 2H), 6.58-6.51 (d, J = 9.0 Hz, 2H), 4.40-4.27 (m, 1H), 3.81 (br. s., 1H), 3.65-3.54 (m, 2H), 3.41-3.32 (m, 1H), 3.30 (s, 3H), 3.30-3.25 (m, 1H), 3.23-3.15 (m, 1H), 3.07-2.98 (m, 1H), 2.37-2.30 (m, 1H), 2.06-1.85 (m, 6H), 1.83-1.70 (m, 1H). |
| 25 | 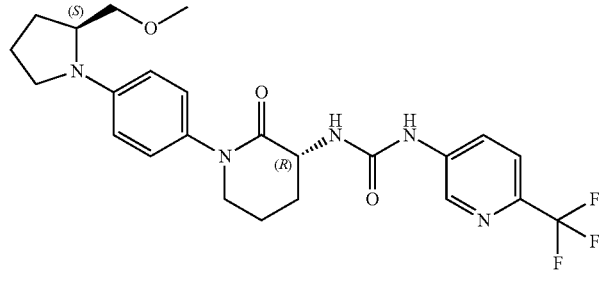<br>1-((R)-1-(4-((S)-2-(methoxymethyl)pyrrolidin-1-yl)phenyl)-2-oxopiperidin-3-yl)-3-(6-(trifluoromethyl)pyridin-3-yl)urea | 492.3 | Method F, RT = 1.78 min, 98.4% | ¹H NMR (400 MHz, DMSO-d₆): δ 9.44 (s, 1H), 8.67 (d, J = 2.2 Hz, 1H), 8.14 (dd, J = 8.4, 2.2 Hz, 1H), 7.76 (d, J = 8.8 Hz, 1H), 7.10 (d, J = 8.8 Hz, 2H), 6.81 (d, J = 6.6 Hz, 1H), 6.65 (m, J = 8.8 Hz, 2H), 4.36-4.20 (m, 1H), 3.81 (br. s., 1H), 3.58 (t, J = 6.1 Hz, 2H), 3.41-3.33 (m, 1H), 3.31-3.25 (m, 1H), 3.30 (s, 3H), 3.23-3.15 (m, 1H), 3.07-2.98 (m, 1H), 2.37-2.26 (m, 1H), 2.05-1.85 (m, 6H), 1.83-1.71 (m, 1H). |

| Ex | Structure and Name | LCMS (M + H)+ | HPLC Method, RT (min) & Purity | ¹H NMR |
|---|---|---|---|---|
| 26 | 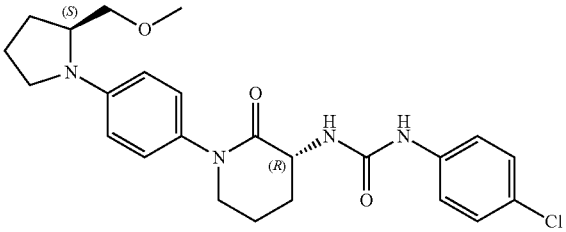<br>1-(4-chlorophenyl)-3-((R)-1-(4-((S)-2-(methoxymethyl)pyrrolidin-1-yl)phenyl)-2-oxopiperidin-3-yl)urea | 457.2 | Method F, RT = 1.85 min, 100.0% | ¹H NMR (400 MHz, DMSO-$d_6$): δ 8.91 (s, 1H), 7.54-7.35 (m, 2H), 7.34-7.18 (m, 2H), 7.10 (d, J = 8.8 Hz, 2H), 6.60 (d, J = 8.8 Hz, 2H), 6.53 (d, J = 6.4 Hz, 1H), 4.34-4.12 (m, 1H), 3.81 (br. s., 1H), 3.57 (t, J = 6.2 Hz, 2H), 3.41-3.30 (m, 2H), 3.28 (s, 3H), 3.24-3.16 (m, 1H), 3.09-2.96 (m, 1H), 2.29 (dd, J = 12.2, 5.6 Hz, 1H), 2.05-1.82 (m, 6H), 1.81-1.65 (m, 1H). |
| 27 | 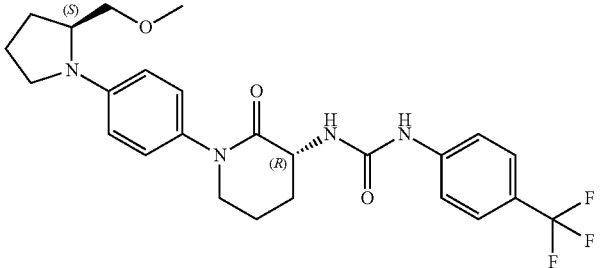<br>1-((R)-1-(4-((S)-2-(methoxymethyl)pyrrolidin-1-yl)phenyl)-2-oxopiperidin-3-yl)-3-(4-(trifluoromethyl)phenyl)urea | 491.3 | Method F, RT = 1.99 min, 98.7% | ¹H NMR (400 MHz, DMSO-$d_6$): δ 9.20 (s, 1H), 7.72-7.46 (m, 4H), 7.10 (d, J = 8.8 Hz, 2H), 6.65 (d, J = 6.4 Hz, 1H), 6.56 (d, J = 9.0 Hz, 2H), 4.34-4.19 (m, 1H), 3.81 (br. s., 1H), 3.58 (t, J = 6.2 Hz, 2H), 3.44-3.39 (m, 2H), 3.28 (s, 3H), 3.24-3.14 (m, 1H), 3.08-2.98 (m, 1H), 2.35-2.24 (m, 1H), 2.06-1.83 (m, 6H), 1.81-1.67 (m, 1H). |
| 28 | 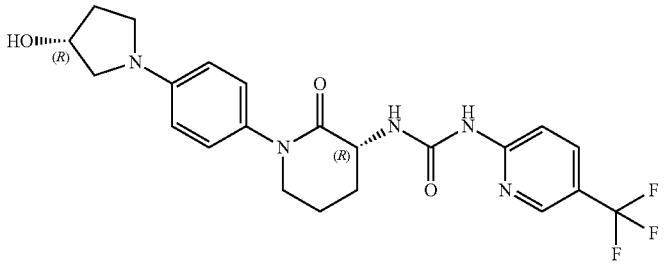<br>1-((R)-1-(4-((R)-3-hydroxypyrrolidin-1-yl)phenyl)-2-oxopiperidin-3-yl)-3-(5-(trifluoromethyl)pyridin-2-yl)urea | 464.2 | Method F, RT = 1.45 min, 100.0% | ¹H NMR (400 MHz, DMSO-$d_6$): δ 9.77 (s, 1H), 8.55 (s, 1H), 8.05 (d, J = 9.3 Hz, 2H), 7.75 (d, J = 8.6 Hz, 1H), 7.05 (d, J = 8.6 Hz, 2H), 6.49 (d, J = 8.8 Hz, 2H), 4.93 (d, J = 4.2 Hz, 1H), 4.44-4.28 (m, 2H), 4.07 (s, 1H), 3.60 (d, J = 9.3 Hz, 2H), 3.17 (d, J = 4.6 Hz, 2H), 3.06 (d, J = 11.0 Hz, 1H), 1.96-1.61 (m, 6H). |

| Ex | Structure and Name | LCMS (M + H)+ | HPLC Method, RT (min) & Purity | ¹H NMR |
|---|---|---|---|---|
| 29 | (R)-1-(1-(4-(4-acetylpiperazin-1-yl)phenyl)-2-oxopiperidin-3-yl)-3-(4-(trifluoromethyl)phenyl)urea | 504.1 | Method F, RT = 1.76 min, 94.8% | ¹H NMR (400 MHz, DMSO-$d_6$): δ 9.20 (s, 1H) 7.53-7.63 (m, 4H) 7.14 (d, J = 8.8 Hz, 2H) 6.96 (d, J = 8.8 Hz, 2H) 6.66 (d, J = 6.36 Hz, 1H) 4.23-4.33 (m, 1H) 3.53-3.65 (m, 6H) 3.05-3.19 (m, 4H) 2.30 (dd, J = 12.10, 5.99 Hz, 1H) 2.04 (s, 3H) 1.92-2.00 (m, 2H) 1.70-1.82 (m, 1H). |
| 30 | (R)-1-(1-(4-(4-methoxypiperidin-1-yl)phenyl)-2-oxopiperidin-3-yl)-3-(4-(trifluoromethyl)phenyl)urea | 491.1 | Method F, RT = 2.05 min, 100% | ¹H NMR (400 MHz, DMSO-$d_6$): δ 9.23-9.18 (m, 1H), 7.64-7.53 (m, 4H), 7.12-7.06 (m, 2H), 6.96-6.89 (m, 2H), 6.70-6.63 (m, 1H), 4.32-4.23 (m, 1H), 3.64-3.56 (m, 2H), 3.51-3.42 (m, 4H), 3.26 (s, 3H), 2.83-2.82 (m, 1H), 2.35-2.24 (m, 1H), 1.98-1.87 (m, 4H), 1.81-1.69 (m, 1H), 1.57-1.43 (m, 2H). |
| 31 | 1-((3R)-1-(4-(3-hydroxypiperidin-1-yl)phenyl)-2-oxopiperidin-3-yl)-3-(4-(trifluoromethyl)phenyl)urea | 477.1 | Method F, RT = 1.83 min, 100% | ¹H NMR (400 MHz, DMSO-$d_6$) δ ppm 9.20 (s, 1 H), 7.64-7.53 (m, 4 H), 7.09 (d, J = 8.80 Hz, 2 H), 6.89 (d, J = 8.80 Hz, 2 H), 6.66 (d, J = 6.36 Hz, 1 H) 4.81 (d, J = 4.65 Hz, 1 H), 4.31-4.23 (m, 1 H), 3.62-3.53 (m, 4H), 3.51-3.38 (m, 2 H), 2.71-2.61 (m, 1 H), 2.54 (s, 1 H), 2.38-2.27 (m, 1 H), 1.99-1.91 (m, 3 H), 1.81-1.67 (m, 2 H), 1.30-1.18 (m, 1H). |

-continued

| Ex | Structure and Name | LCMS (M + H)+ | HPLC Method, RT (min) & Purity | $^1$H NMR |
|---|---|---|---|---|
| 32 | 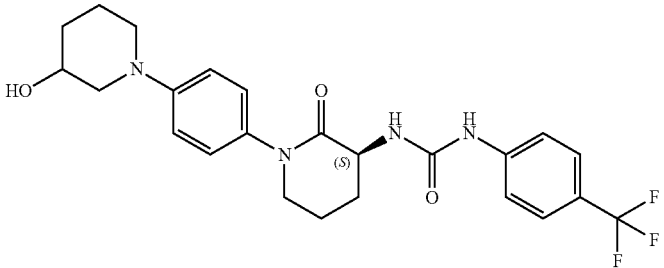<br>1-((3S)-1-(4-(3-hydroxypiperidin-1-yl)phenyl)-2-oxopiperidin-3-yl)-3-(4-(trifluoromethyl)phenyl)urea | 477.1 | Method F, RT = 1.83 min, 100% | $^1$H NMR (400 MHz, DMSO-d$_6$) δ ppm 9.21 (s, 1 H), 7.64-7.53 (m, 4 H), 7.09 (d, J = 9.05 Hz, 2 H), 6.89 (d, J = 9.05 Hz, 2 H) 6.66 (d, J = 6.60 Hz, 1 H), 4.81 (d, J = 4.89 Hz, 1 H), 4.33-4.19 (m, 1 H), 3.66-3.54 (m, 4H), 3.50-3.39 (m, 2 H), 2.71-2.59 (m, 1 H), 2.53 (s, 1 H), 2.37-2.26 (m, 1 H), 2.02-1.89 (m, 3 H), 1.80-1.70 (m, 2 H), 1.30-1.18 (m, 1H). |
| 33 | 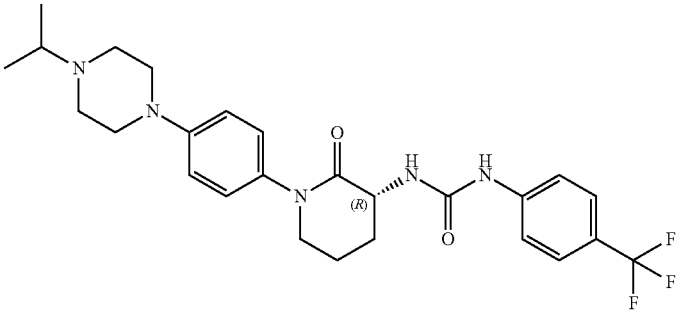<br>(R)-1-(1-(4-(4-isopropylpiperazin-1-yl)phenyl)-2-oxopiperidin-3-yl)-3-(4-(trifluoromethyl)phenyl)urea | 504.1 | Method F, RT = 1.76 min, 99% | $^1$H NMR (400 MHz, DMSO-d$_6$): δ 9.20 (s, 1H), 7.64-7.53 (m, 4H), 7.14 (d, J = 7.3 Hz, 2H), 6.97 (br. s., 2H), 6.66 (d, J = 6.8 Hz, 1H), 4.34-4.21 (m, 1H), 3.60 (m, 2H), 3.07 (m, 6H), 2.30 (m, 2H), 1.95 (m, 3H), 1.78 (m, 2H), 1.20-1.04 (m, 6H). |
| 34 | 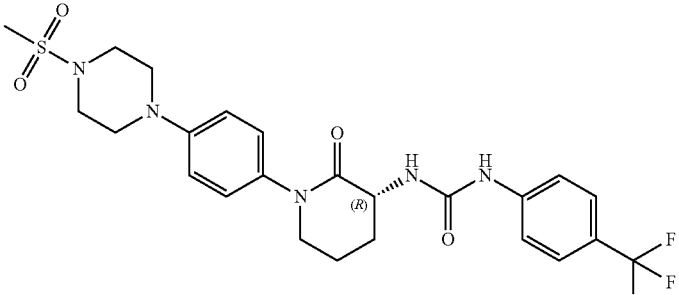<br>(R)-1-(1-(4-(4-(methylsulfonyl)piperazin-1-yl)phenyl)-2-oxopiperidin-3-yl)-3-(4-(trifluoromethyl)phenyl)urea | 540.1 | Method F, RT = 1.88 min, 100% | $^1$H NMR (400 MHz, DMSO-d$_6$): δ 9.20 (s, 1H), 7.62-7.54 (m, 4H), 7.15 (d, J = 9.0 Hz, 2H), 6.98 (d, J = 9.0 Hz, 2H), 6.65 (d, J = 6.4 Hz, 1H), 4.27 (s, 1H), 3.60 (d, J = 6.6 Hz, 2H), 3.16-3.09 (m, 6H), 2.92 (s, 3H), 2.31-2.24 (m, 1H), 2.11-2.03 (m, 1H), 1.96 (m, 3H), 1.77 (m, 1H). |

-continued

| Ex | Structure and Name | LCMS (M + H)+ | HPLC Method, RT (min) & Purity | ¹H NMR |
|----|---|---|---|---|
| 35 | 1-((R)-1-(4-((R)-3-methylmorpholino)phenyl)-2-oxopiperidin-3-yl)-3-(4-(trifluoromethyl)phenyl)urea | 477 | Method F, RT = 2.03 min, 99.21% | ¹H NMR (400 MHz, DMSO-d$_6$): δ 9.24-9.15 (m, 1H), 7.62-7.54 (m, 4H), 7.15-7.10 (m, 2H), 6.93-6.84 (m, 2H), 6.70-6.61 (m, 1H), 4.33-4.23 (m, 1H), 3.94-3.79 (m, 2H), 3.73-3.49 (m, 6H), 3.05-2.94 (m, 1H), 2.37-2.24 (m, 1H), 2.02-1.90 (m, 2H), 1.84-1.69 (m, 1H), 1.02-0.95 (m, 3H) |
| 36 | 1-(4-methoxyphenyl)-3-((R)-1-(4-((R)-3-methylmorpholino)phenyl)-2-oxopiperidin-3-yl)urea | 439.1 | Method F, RT = 1.57 min, 98.37% | ¹H NMR (400 MHz, DMSO-d$_6$): δ 8.57-8.52 (m, 1H), 7.32-7.25 (m, 2H), 7.16-7.09 (m, 2H), 6.92-6.85 (m, 2H), 6.84-6.78 (m, 2H), 6.40-6.32 (m, 1H), 4.30-4.20 (m, 1H), 3.93-3.86 (m, 1H), 3.85-3.80 (m, 1H), 3.69 (s, 5H), 3.64-3.54 (m, 3H), 3.20-3.13 (m, 1H), 3.03-2.95 (m, 1H), 2.34-2.23 (m, 1H), 1.98-1.90 (m, 2H), 1.79-1.66 (m, 1H), 1.02-0.96 (m, 3H) |
| 37 | 1-((R)-1-(4-((S)-3-methylmorpholino)phenyl)-2-oxopiperidin-3-yl)-3-(4-(trifluoromethyl)phenyl)urea | 477.1 | Method F, RT = 2.012 min, 99.29% | ¹H NMR (400 MHz, DMSO-d$_6$): δ 9.22-9.17 (m, 1H), 7.62-7.54 (m, 4H), 7.15-7.10 (m, 2H), 6.92-6.86 (m, 2H), 6.69-6.62 (m, 1H), 4.33-4.23 (m, 1H), 3.93-3.79 (m, 2H), 3.73-3.65 (m, 2H), 3.64-3.51 (m, 3H), 3.19-3.12 (m, 1H), 3.04-2.95 (m, 1H), 2.36-2.26 (m, 1H), 2.00-1.91 (m, 1H), 1.83-1.70 (m, 2H), 1.01-0.96 (m, 3H). |
| 38 | 1-((3R)-1-(4-(3-methylpiperidin-1-yl)phenyl)-2-oxopiperidin-3-yl)-3-(4-(trifluoromethyl)phenyl)urea | 475.1 | Method F, RT = 2.57 min, 100% | ¹H NMR (400 MHz, DMSO-d$_6$): δ 9.20 (s, 1H), 7.57-7.59 (m, 4H), 7.09 (d, J = 9.20 Hz, 2H), 6.91 (d, J = 8.80 Hz, 2H), 6.65 (d, J = 6.40 Hz, 1H), 4.25-4.33 (m, 1H), 3.58-3.62 (m, 4H), 2.51-2.52 (m, 1H), 2.30-2.33 (m, 2H), 1.94-1.96 (m, 2H), 1.68-1.78 (m, 4H), 1.54-1.57 (m, 1H), 1.01-1.04 (m, 1H), 0.91 (d, J = 6.40 Hz, 3H). |

| Ex | Structure and Name | LCMS (M + H)+ | HPLC Method, RT (min) & Purity | $^1$H NMR |
|---|---|---|---|---|
| 39 | 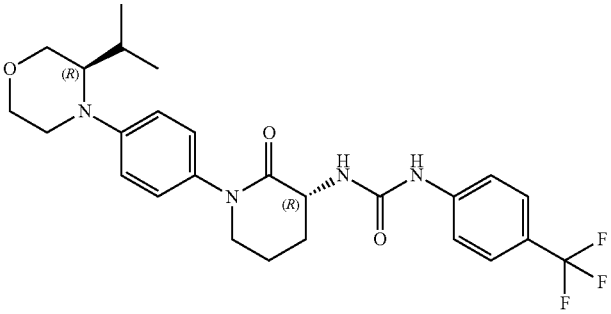<br>1-((R)-1-(4-((R)-3-isopropylmorpholino)phenyl)-2-oxopiperidin-3-yl)-3-(4-(trifluoromethyl)phenyl)urea | 505.2 | Method F, RT = 2.39 min, 100% | $^1$H NMR (400 MHz, DMSO-d$_6$): δ 9.20 (s, 1H) 7.54-7.62 (m, 4H) 7.07 (d, J = 9.00 Hz, 2H) 6.84 (d, J = 9.00 Hz, 2H) 6.65 (d, J = 6.11 Hz, 1H) 4.22-4.31 (m, 1H) 3.89 (d, J = 11.49 Hz, 1H) 3.79 (d, J = 9.05 Hz, 1H) 3.60 (t, J = 6.36 Hz, 2H) 3.45-3.54 (m, 3H) 3.39-3.25 (m, 2H), 2.25-2.35 (m, 2H) 1.90-2.00 (m, 2H) 1.80-1.66 (m, 1H) 0.95 (d, J = 7.09 Hz, 3H) 0.76 (d, J = 7.09 Hz, 3H). |
| 40 | 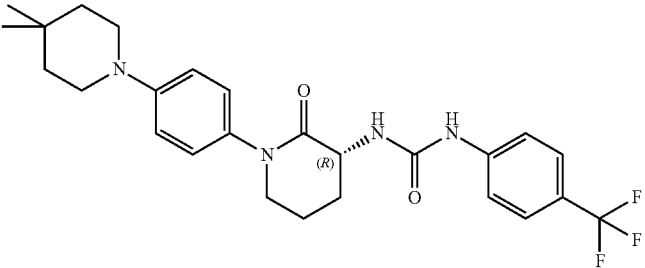<br>(R)-1-(1-(4-(4,4-dimethylpiperidin-1-yl)phenyl)-2-oxopiperidin-3-yl)-3-(4-(trifluoromethyl)phenyl)urea | 489.2 | Method F, RT = 2.67 min, 100% | $^1$H NMR (400 MHz, DMSO-d$_6$): δ 9.20 (s, 1H), 7.56-7.61 (m, 4H), 7.09 (d, J = 8.80 Hz, 2H), 6.92 (d, J = 9.20 Hz, 2H), 6.65 (d, J = 6.40 Hz, 1H), 4.26-4.29 (m, 1H), 3.59-3.62 (m, 2H), 3.13-3.18 (m, 4H), 2.29-2.33 (m, 1H), 1.94-1.97 (m, 2H), 1.70-1.81 (m, 1H), 1.42-1.45 (m, 4H), 0.95 (s, 6H). |
| 41 | 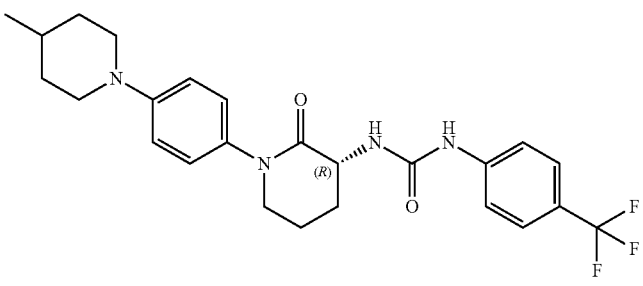<br>(R)-1-(1-(4-(4-methylpiperidin-1-yl)phenyl)-2-oxopiperidin-3-yl)-3-(4-(trifluoromethyl)phenyl)urea | 475.1 | Method F, RT = 2.56 min, 100% | $^1$H NMR (400 MHz, DMSO-d$_6$): δ 9.20 (s, 1H), 7.56-7.61 (m, 4H), 7.09 (d, J = 8.80 Hz, 2H), 6.91 (d, J = 8.80 Hz, 2H), 6.65 (d, J = 6.40 Hz, 1H), 4.23-4.31 (m, 1H), 3.58-3.63 (m, 4H), 2.62-2.68 (m, 2H), 2.33-2.33 (m, 1H), 1.94-1.97 (m, 2H), 1.67-1.73 (m, 3H), 1.49-1.54 (m, 1H), 1.21-1.24 (m, 2H), 0.93 (d, J = 6.40 Hz, 3H). |

-continued

| Ex | Structure and Name | LCMS (M + H)+ | HPLC Method, RT (min) & Purity | ¹H NMR |
|---|---|---|---|---|
| 42 | (R)-1-(1-(4-(4-ethylpiperazin-1-yl)phenyl)-2-oxopiperidin-3-yl)-3-(4-(trifluoromethyl)phenyl)urea | 490.1 | Method F, RT = 1.71 min, 100% | ¹H NMR (400 MHz, DMSO-$d_6$): δ 9.20 (s, 1H), 7.65-7.52 (m, 4H), 7.13 (d, J = 9.0 Hz, 2H), 6.94 (d, J = 8.8 Hz, 2H), 6.66 (d, J = 6.4 Hz, 1H), 4.33-4.23 (m, 1H), 3.65-3.56 (m, 2H), 3.17 (m, 6H), 2.67 (m, 3H), 2.36-2.23 (m, 2H), 2.02-1.90 (m, 2H), 1.83-1.68 (m, 1H), 1.08 (t, J = 7.1 Hz, 3H). |
| 43 | 1-((R)-1-(4-((2S,6R)-2,6-dimethylmorpholino)phenyl)-2-oxopiperidin-3-yl)-3-(4-(trifluoromethyl)phenyl)urea | 491.1 | Method F, RT = 2.15 min, 100% | ¹H NMR (400 MHz, DMSO-$d_6$): δ 9.20 (s, 1H), 7.58-7.59 (m, 4H), 7.12 (d, J = 8.80 Hz, 2H), 6.94 (d, J = 8.80 Hz, 2H), 6.66 (d, J = 6.40 Hz, 1H), 4.27-4.31 (m, 1H), 3.68-3.71 (m, 2H), 3.55-3.61 (m, 4H), 3.35-3.25 (m, 2H), 2.21-2.33 (m, 1H), 1.93-1.97 (m, 2H), 1.77-1.78 (m, 1H), 1.15 (d, J = 6.40 Hz, 6H). |
| 44 | (R)-1-(1-(4-(4-methylpiperazin-1-yl)phenyl)-2-oxopiperidin-3-yl)-3-(4-(trifluoromethyl)phenyl)urea | 476.1 | Method F, RT = 2.02 min, 98.9% | ¹H NMR (400 MHz, DMSO-$d_6$): δ 9.20 (s, 1H), 7.58-7.61 (m, 4H), 7.13 (d, J = 9.20 Hz, 2H), 6.95 (d, J = 9.20 Hz, 2H), 6.66 (d, J = 6.40 Hz, 1H), 4.25-4.31 (m, 1H), 3.59-3.62 (m, 2H), 3.16-3.21 (m, 4H), 2.67-2.71 (m, 4H), 2.41 (s, 3H), 2.26-2.33 (m, 1H), 1.93-1.97 (m, 2H), 1.74-1.80 (m, 1H). |

| Ex | Structure and Name | LCMS (M + H)+ | HPLC Method, RT (min) & Purity | ¹H NMR |
|---|---|---|---|---|
| 45 | (R)-1-(2-oxo-1-(4-(piperidin-1-yl)phenyl)piperidin-3-yl)-3-(4-(trifluoromethyl)phenyl)urea | 461.1 | Method F, RT = 2.66 min, 97% | ¹H NMR (400 MHz, DMSO-d₆): δ 9.19 (s, 1H), 7.58-7.59 (m, 4H), 7.12 (d, J = 8.80 Hz, 2H), 6.97 (d, J = 7.20 Hz, 2H), 6.65 (d, J = 6.80 Hz, 1H), 4.25-4.29 (m, 1H), 3.37-3.61 (m, 2H), 3.14-3.17 (m, 4H), 2.27-2.33 (m, 1H), 1.93-1.97 (m, 2H), 1.77-1.78 (m, 1H), 1.60-1.69 (m, 4H), 1.53-1.55 (m, 2H). |
| 46 | (R)-1-(1-(4-morpholinophenyl)-2-oxopiperidin-3-yl)-3-(4-(trifluoromethyl)phenyl)urea | 463.1 | Method F, RT = 2.22 min, 100% | ¹H NMR (400 MHz, DMSO-d₆): δ 9.20 (s, 1H), 7.58-7.61 (m, 4H), 7.14 (d, J = 8.80 Hz, 2H), 6.94 (d, J = 8.80 Hz, 2H), 6.66 (d, J = 6.40 Hz, 1H), 4.27-4.30 (m, 1H), 3.72-3.75 (m, 4H), 3.59-3.63 (m, 2H), 3.09-3.11 (m, 4H), 2.28-2.33 (m, 1H), 1.94-1.97 (m, 2H), 1.71-1.78 (m, 1H). |
| 47 | 1-((R)-1-(4-((1R,5S)-8-oxa-3-azabicyclo[3.2.1]octan-3-yl)phenyl)-2-oxopiperidin-3-yl)-3-(6-(trifluoromethyl)pyridin-3-yl)urea | 490.2 | Method F, RT = 1.48 min, 98.83% | ¹H NMR (400 MHz, DMSO-d₆): δ 9.44 (s, 1H), 8.67 (d, J = 2.4 Hz, 1H), 8.15 (dd, J = 8.6, 2.2 Hz, 1H), 7.76 (d, J = 8.8 Hz, 1H), 7.10 (d, J = 8.8 Hz, 2H), 6.97-6.71 (m, 3H), 4.30 (dt, J = 11.7, 6.1 Hz, 1H), 4.14 (br. s., 2H), 3.70 (d, J = 10.8 Hz, 2H), 3.61 (t, J = 6.2 Hz, 2H), 3.44 (d, J = 10.8 Hz, 2H), 2.35-2.22 (m, 1H), 2.02-1.72 (m, 7H). |
| 48 | 1-((R)-1-(4-((R)-3-methylmorpholino)phenyl)-2-oxopiperidin-3-yl)-3-(5-(trifluoromethyl)pyridin-2-yl)urea | 487.3 | Method F, RT = 1.64 min, 100% | ¹H NMR (400 MHz, DMSO-d₆): δ 9.79 (s, 1H), 8.55 (s, 1H), 8.20-7.94 (m, 2H), 7.72 (d, J = 9.3 Hz, 1H), 7.12 (d, J = 8.8 Hz, 2H), 6.90 (d, J = 8.8 Hz, 2H), 4.46-4.27 (m, 1H), 3.96-3.86 (m, 1H), 3.83 (d, J = 6.8 Hz, 1H), 3.73-3.53 (m, 5H), 3.16 (d, J = 13.0 Hz, 1H), 3.04-2.92 (m, 1H), 2.36-2.30 (m, 1H), 2.04-1.88 (m, 2H), 1.83-1.67 (m, 1H), 0.99 (d, J = 6.6 Hz, 3H). |

-continued

| Ex | Structure and Name | LCMS (M + H)+ | HPLC Method, RT (min) & Purity | ¹H NMR |
|---|---|---|---|---|
| 49 | 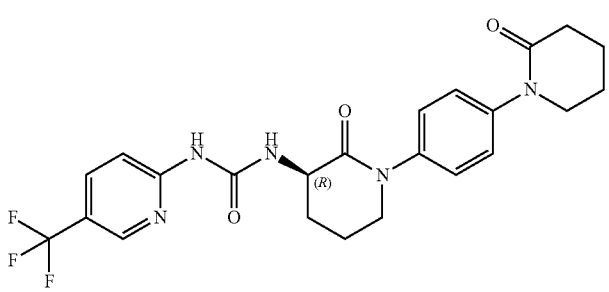<br>(R)-1-(2-oxo-1-(4-(2-oxopiperidin-1-yl)phenyl)piperidin-3-yl)-3-(5-(trifluoromethyl)pyridin-2-yl)urea | 476.2 | Method F, RT = 1.43 min, 97.8% | ¹H NMR (400 MHz, DMSO-$d_6$): δ 9.79 (s, 1H), 8.55 (s, 1H), 8.15 (br. s., 1H), 8.08-7.98 (m, 1H), 7.71 (d, J = 8.8 Hz, 1H), 7.35-7.22 (m, 4H), 4.44-4.35 (m, 1H), 3.76-3.62 (m, 2H), 3.61-3.57 (m, 2H), 2.38 (t, J = 6.4 Hz, 2H), 2.34-2.28 (m, 1H), 2.04-1.93 (m, 2H), 1.91-1.77 (m, 5H) |
| 50 | 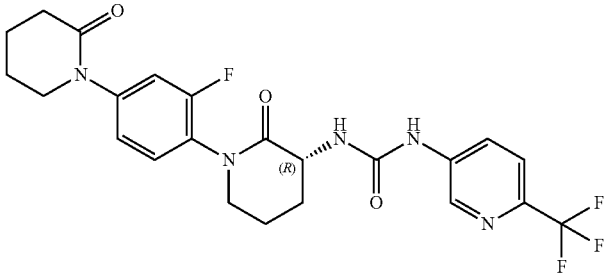<br>(R)-1-(1-(2-fluoro-4-(2-oxopiperidin-1-yl)phenyl)-2-oxopiperidin-3-yl)-3-(6-(trifluoromethyl)pyridin-3-yl)urea | 494.2 | Method F, RT = 1.36 min, 100.0% | ¹H NMR (400 MHz, DMSO-$d_6$): δ 9.40 (s, 1H), 8.67 (s, 1H), 8.15 (d, J = 8.8 Hz, 1H), 7.76 (d, J = 8.6 Hz, 1H), 7.38 (t, J = 8.6 Hz, 1H), 7.30 (d, J = 11.0 Hz, 1H), 7.18 (d, J = 9.0 Hz, 1H), 6.86 (d, J = 7.1 Hz, 1H), 4.37 (dt, J = 11.9, 6.1 Hz, 1H), 3.70-3.54 (m, 4H), 2.40 (t, J = 6.1 Hz, 2H), 2.31 (dd, J = 12.1, 5.5 Hz, 1H), 2.08-1.95 (m, 2H), 1.95-1.72 (m, 5H). |
| 51 | 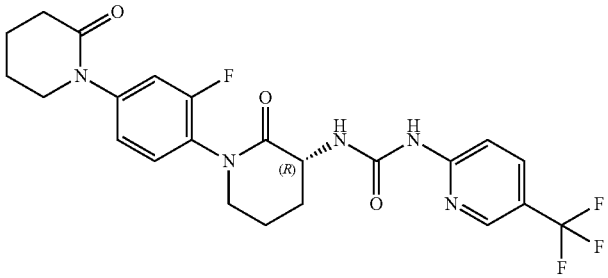<br>(R)-1-(1-(2-fluoro-4-(2-oxopiperidin-1-yl)phenyl)-2-oxopiperidin-3-yl)-3-(5-(trifluoromethyl)pyridin-2-yl)urea | 494.2 | Method F, RT = 1.49 min, 100.0% | ¹H NMR (400 MHz, DMSO-$d_6$): δ 9.77 (s, 1H), 8.55 (s, 1H), 8.15-8.00 (m, 2H), 7.74 (d, J = 9.0 Hz, 1H), 7.39 (t, J = 8.6 Hz, 1H), 7.31 (d, J = 2.0 Hz, 1H), 7.18 (d, J = 8.6 Hz, 1H), 4.48-4.36 (m, 1H), 3.70-3.57 (m, 4H), 2.40 (t, J = 6.4 Hz, 2H), 2.37-2.29 (m, 2H), 2.08-1.96 (m, 1H), 1.91-1.78 (m, 5H). |

-continued

| Ex | Structure and Name | LCMS (M + H)+ | HPLC Method, RT (min) & Purity | $^1$H NMR |
|---|---|---|---|---|
| 52 | (R)-1-(1-(2-fluoro-4-(2-oxopiperidin-1-yl)phenyl)-2-oxopiperidin-3-yl)-3-(4-(trifluoromethyl)phenyl)urea | 493.2 | Method F, RT = 1.58 min, 100.0% | $^1$H NMR (400 MHz, DMSO-d$_6$): δ 9.17 (s, 1H), 7.63-7.54 (m, 3H), 7.38 (t, J = 8.6 Hz, 1H), 7.28 (d, J = 2.0 Hz, 1H), 7.31 (d, J = 2.0 Hz, 1H), 7.18 (d, J = 8.3 Hz, 1H), 6.69 (d, J = 7.1 Hz, 1H), 4.40-4.29 (m, 1H), 3.67-3.58 (m, 4H), 2.40 (t, J = 6.2 Hz, 2H), 2.31 (dd, J = 12.3, 5.7 Hz, 1H), 2.05-1.96 (m, 2H), 1.84-1.75 (m, 5H). |
| 53 | (R)-1-(1-(2-fluoro-4-morpholinophenyl)-2-oxopiperidin-3-yl)-3-(4-(trifluoromethyl)phenyl)urea | 481.2 | Method F, RT = 1.72 min, 100.0% | $^1$H NMR (400 MHz, DMSO-d$_6$): δ 9.16 (s, 1H), 7.72-7.46 (m, 4H), 7.18 (t, J = 8.7 Hz, 1H), 6.90-6.73 (m, 2H), 6.67 (d, J = 6.6 Hz, 1H), 4.31 (dt, J = 11.7, 6.0 Hz, 1H), 3.78-3.65 (m, 4H), 3.55 (t, J = 6.4 Hz, 2H), 3.19-3.09 (m, 4H), 2.32-2.23 (m, 1H), 2.05-1.91 (m, 2H), 1.84-1.66 (m, 1H). |

Example 54: (R)-1-(1-(6-Morpholinopyridin-3-yl)-2-oxopiperidin-3-yl)-3-(4-(trifluoromethyl)phenyl)urea

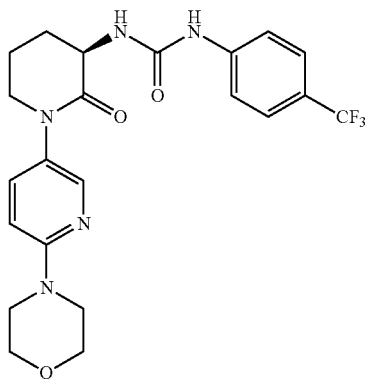 [SMILES: O=C(Nc1ccc(C(F)(F)F)cc1)N[C@@H]1CCCN(c2ccc(N3CCOCC3)nc2)C1=O]

Example 54A: tert-Butyl (1-(6-fluoropyridin-3-yl)-2-oxopiperidin-3-yl)carbamate

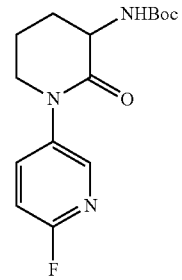 [SMILES: CC(C)(C)OC(=O)NC1CCCN(c2ccc(F)nc2)C1=O]

To a solution of tert-butyl (2-oxopiperidin-3-yl)carbamate (5.0 g, 23 mmol) in DMF (50 mL) at rt, were added 5-bromo-2-fluoropyridine (2.9 mL, 28 mmol), potassium phosphate tribasic (9.9 g, 47 mmol) and, N,N'-dimethylethylenediamine (0.41 g, 4.7 mmol). The reaction mixture was purged with nitrogen for 5 min and charged with copper(I) iodide (0.44 g, 2.3 mmol). The reaction mixture was again purged with nitrogen for 3 min and heated at 60° C. for 16 h. The reaction mixture was cooled, filtered through celite and the filtrate was concentrated under reduced pressure. The crude mixture was purified using column chromatography to afford Example 54A (3.5 g, 11 mmol, 49% yield) as a white solid. MS(ESI) m/z: 310.5 [M+H]+; $^1$H NMR (400 MHz, DMSO-d6): δ 8.79 (dd, J=2.50, 0.50 Hz, 1H), 7.95 (s, 1H), 7.93-7.90 (m, 1H), 7.25 (dd, 1H, J=8.8, 3.2 Hz), 4.18-4.05 (m, 1H), 4.70-4.55 (m, 2H), 2.10-1.71 (m, 4H), 1.32 (s, 9H).

Example 54B: tert-Butyl (1-(6-morpholinopyridin-3-yl)-2-oxopiperidin-3-yl)carbamate

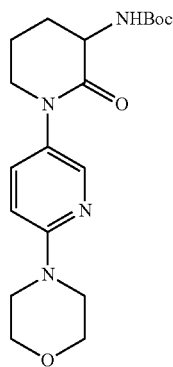 [SMILES: CC(C)(C)OC(=O)NC1CCCN(c2ccc(N3CCOCC3)nc2)C1=O]

To a stirred solution of Example 54A (1.0 g, 3.2 mmol) in DMF (1 mL) under nitrogen atmosphere at room temperature, morpholine (0.34 g, 3.9 mmol), and DIPEA (1.7 mL, 9.7 mmol) were added. The reaction mixture was gradually warmed to 130° C. and stirred for 16 hours. The reaction mixture was then cooled to rt, filtered through celite, and washed with EtOAc. The combined filtrates were concentrated under reduced pressure, and the crude compound was purified using by column chromatography to afford Example 54B (0.50 g, 1.3 mmol, 41% yield) as a pale yellow solid. MS(ESI) m/z: 377.5 [M+H]+.

Example 54C: 3-Amino-1-(6-morpholinopyridin-3-yl)piperidin-2-one hydrochloride

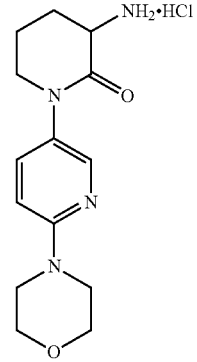

To an ice cooled solution of Example 54B (0.80 g, 2.1 mmol) in 1,4-dioxane (5 mL), was added 4N HCl in 1,4-dioxane (5.3 mL, 21 mmol), and the mixture was stirred at rt for two hours. The solvent was evaporated, and the sample was dried under reduced pressure to obtain a gummy solid. The solid was triturated with diethyl ether (2×20 mL) and dried to afford Example 54C (0.66 g, 2.1 mmol, 99% yield) as a off white solid. The product was used in the subsequent step without purification.

Example 54: TEA (0.20 mL, 1.4 mmol), and 1-isocyanato-4-(trifluoromethyl)benzene (0.15 g, 0.80 mmol) were added sequentially to a stirred solution of Example 54C (0.20 g, 0.64 mmol) in THF (3 mL) under nitrogen at rt. The resulting reaction mixture was stirred at rt for 3 h. The reaction mixture was quenched with water and extracted with EtOAc. The organic layer was washed with ice cold water, brine, dried over $Na_2SO_4$, and concentrated under reduced pressure. The crude compound was purified by column chromatography followed by chiral HPLC to afford Example 54 (18 mg, 0.038 mmol, 5.9% yield). MS(ESI) m/z: 464.2 [M+H]+; $^1$H NMR (400 MHz, DMSO-d6): δ 9.19 (s, 1H), 8.06 (d, J=2.7 Hz, 1H), 7.63-7.54 (m, 4H), 7.50 (dd, J=8.8, 2.7 Hz, 1H), 6.85 (d, J=8.8 Hz, 1H), 6.66 (d, J=6.4 Hz, 1H), 4.30 (dt, J=11.6, 6.1 Hz, 1H), 3.72-3.66 (m, 4H), 3.65-3.56 (m, 2H), 3.45-3.40 (m, 4H), 2.29 (dd, J=12.5, 6.1 Hz, 1H), 2.04-1.92 (m, 2H), 1.86-1.74 (m, 1H). RT=1.521 min, 97.9%, (Method F)

Additional examples of compounds of this invention shown in Table 2 below were prepared using combinations of the procedures described in Example 54 or modifications thereof known to one skilled in the art of organic synthesis.

| Ex | Structure | LCMS (M + H)+ | HPLC Method, RT (min.) & Purity | $^1$H NMR |
|---|---|---|---|---|
| 55 | 1-((R)-1-(6-((R)-3-hydroxypyrrolidin-1-yl)pyridin-3-yl)-2-oxopiperidin-3-yl)-3-(4-(trifluoromethyl)phenyl)urea | 464 | Method F, RT = 1.61 min, 99.3% | $^1$H NMR (400 MHz, DMSO-d$_6$): δ 9.19 (s, 1H), 7.96 (d, J = 2.45 Hz, 1H), 7.55-7.63 (m, 4H), 7.40 (dd, J = 8.93, 2.57 Hz, 1H), 6.66 (d, J = 6.60 Hz, 1H), 6.43 (d, J = 9.05 Hz, 1H), 4.94 (br. s., 1H), 4.38 (br. s., 1H), 4.23-4.33 (m, 1H) 3.58 (d, J = 5.38 Hz, 2H), 3.40-3.48 (m, 4H), 2.24-2.34 (m, 1H), 1.93-2.05 (m, 3H), 1.72-1.92 (m, 2H) |

-continued

| Ex | Structure | LCMS (M + H)+ | HPLC Method, RT (min.) & Purity | ¹H NMR |
|---|---|---|---|---|
| 56 | 1-((3R)-1-(6-(3-(hydroxymethyl)piperidin-1-yl)pyridin-3-yl)-2-oxopiperidin-3-yl)-3-(4-(trifluoromethyl)phenyl)urea | 492.1 | Method F, RT = 1.85 min, 97.8% | ¹H NMR (400 MHz, DMSO-d₆): δ 9.20 (s, 1H) 8.00 (d, J = 2.45 Hz, 1H), 7.55-7.62 (m, 4H), 7.43 (dd, J = 9.17, 2.57 Hz, 1H), 6.80 (d, J = 9.05 Hz, 1H), 6.66 (d, J = 6.85 Hz, 1H), 4.55 (t, J = 5.38 Hz, 1H), 4.22-4.33 (m, 2H), 4.08-4.17 (m, 1H), 3.57-3.63 (m, 2H), 3.35-3.22 (m, 2H), 2.76-2.94 (m, 1H), 2.53-2.61 (m, 1H), 2.23-2.35 (m, 2H), 1.93-2.02 (m, 2H), 1.64-1.85 (m, 3H), 1.59 (br. s., 1H), 1.50-1.35 (m, 1H). |
| 57 | 1-((3R)-1-(6-(3-fluoropiperidin-1-yl)pyridin-3-yl)-2-oxopiperidin-3-yl)-3-(4-(trifluoromethyl)phenyl)urea | 480.2 | Method F, RT = 2.06 min, 100% | ¹H NMR (400 MHz, DMSO-d₆): δ 9.20 (s, 1H), 8.01 (d, J = 2.69 Hz, 1H), 7.54-7.62 (m, 4H), 7.44 (dd, J = 8.93, 2.81 Hz, 1H), 6.87 (d, J = 9.05 Hz, 1H), 6.67 (d, J = 6.60 Hz, 1H), 4.65-4.83 (m, 1H), 4.25-4.33 (m, 1H), 3.74-3.84 (m, 1H), 3.56-3.74 (m, 4H), 3.42-3.31 (m, 1H), 2.28 (dd, J = 12.35, 5.75 Hz, 1H), 1.92-2.02 (m, 2H), 1.71-1.90 (m, 4H), 1.55-1.46 (m, 1H) |
| 58 | (R)-1-(1-(6-(4-methoxypiperidin-1-yl)pyridin-3-yl)-2-oxopiperidin-3-yl)-3-(4-(trifluoromethyl)phenyl)urea | 492.1 | Method F, RT = 1.96 min, 100% | ¹H NMR (400 MHz, DMSO-d₆): δ 9.21-9.14 (m, 1H), 8.03-7.97 (m, 1H), 7.62-7.53 (m, 4H), 7.46-7.40 (m, 1H), 6.88-6.80 (m, 1H), 6.70-6.61 (m, 1H), 4.36-4.21 (m, 1H), 3.96-3.86 (m, 2H), 3.81-3.60 (m, 3H), 3.31-3.21 (m, 2H), 3.13 (s, 3H), 2.33-2.18 (m, 1H), 2.02-1.92 (m, 1H), 1.91-1.72 (m, 4H), 1.46-1.31 (m, 2H) |
| 59 | (R)-1-(1-(6-(4-methylpiperidin-1-yl)pyridin-3-yl)-2-oxopiperidin-3-yl)-3-(4-(trifluoromethyl)phenyl)urea | 476.1 | Method F, RT = 2.31 min, 100% | ¹H NMR (400 MHz, DMSO-d₆): δ 9.19 (s, 1H), 8.00 (d, J = 2.69 Hz, 1H), 7.54-7.64 (m, 4H), 7.42 (dd, J = 9.05, 2.69 Hz, 1H), 6.82 (d, J = 9.05 Hz, 1H), 6.66 (d, J = 6.85 Hz, 1H), 4.27-4.32 (m, 1H), 3.57-3.64 (m, 2H), 3.32-3.42 (m, 4H), 2.23-2.31 (m, 1H), 1.91-2.02 (m, 2H), 1.85-1.75 (m, 1H), 1.70-1.65 (m, 2H), 1.53-1.62 (m, 1H), 1.02-1.14 (m, 2H), 0.91 (d, J = 6.36 Hz, 3H). |

| Ex | Structure | LCMS (M + H)+ | HPLC Method, RT (min.) & Purity | ¹H NMR |
|---|---|---|---|---|
| 60 | 1-((3R)-1-(6-(3-hydroxypiperidin-1-yl)pyridin-3-yl)-2-oxopiperidin-3-yl)-3-(4-(trifluoromethyl)phenyl)urea | 478.1 | Method F, RT = 1.78 min, 100% | ¹H NMR (400 MHz, DMSO-$d_6$): δ 9.19 (s, 1H), 7.99 (s, 1H) 7.59 (s, 4H), 7.45 (d, J = 10.03 Hz, 1H), 6.84 (d, J = 8.07 Hz, 1H), 6.66 (d, J = 6.60 Hz, 1H), 4.31 (br. s., 1H) 4.12 (br. s., 1H) 3.95 (d, J = 11.49 Hz, 1H), 3.68-3.59 (m, 2H), 3.49-3.31 (m, 2H), 2.88-2.93 (m, 2H), 2.30-2.23 (m, 1H), 1.96-1.62 (m, 4H) 1.42-1.32 (m, 2H), 1.28-1.19 (m, 1H). |
| 61 | (R)-1-(1-(6-(4-(2-hydroxyethyl)piperazin-1-yl)pyridin-3-yl)-2-oxopiperidin-3-yl)-3-(4-(trifluoromethyl)phenyl)urea | 507.1 | Method F, RT = 1.63 min, 100% | ¹H NMR (400 MHz, DMSO-$d_6$): δ 9.20 (s, 1H), 8.03 (d, J = 2.69 Hz, 1H), 7.54-7.62 (m, 4H), 7.46 (dd, J = 9.05, 2.69 Hz, 1H), 6.84 (d, J = 9.05 Hz, 1H), 6.67 (d, J = 6.85 Hz, 1H), 4.46 (br. s., 1H), 4.26-4.34 (m, 1H), 3.57-3.66 (m, 2H), 3.51-3.57 (m, 2H), 3.44-3.49 (m, 5H), 3.42-3.31 (m, 3H), 2.44 (t, J = 6.11 Hz, 2H), 2.23-2.34 (m, 1H), 1.93-2.02 (m, 2H), 1.73-1.86 (m, 1H) |
| 62 | 1-((R)-1-(6-((1R,5S)-3-oxa-8-azabicyclo[3.2.1]octan-8-yl)pyridin-3-yl)-2-oxopiperidin-3-yl)-3-(6-(trifluoromethyl)pyridin-3-yl)urea | 491.3 | Method F, RT = 1.38 min, 100% | ¹H NMR (400 MHz, DMSO-$d_6$): δ 9.44 (s, 1H), 8.67 (s, 1H), 8.15 (d, J = 8.8 Hz, 1H), 8.02 (s, 1H), 7.76 (d, J = 8.8 Hz, 1H), 7.46 (d, J = 9.0 Hz, 1H), 6.83 (d, J = 6.4 Hz, 1H), 6.73 (d, J = 9.0 Hz, 1H), 4.42 (br. s., 2H), 4.34-4.22 (m, 1H), 3.79 (d, J = 12.0 Hz, 2H), 3.61 (d, J = 3.4 Hz, 2H), 2.92 (d, J = 12.0 Hz, 2H), 2.32-2.23 (m, 1H), 2.05-1.94 (m, 2H), 1.86-1.80 (m, 3H), 1.78-1.72 (m 2H). |
| 63 | 1-((R)-1-(6-((S)-2-(methoxymethyl)pyrrolidin-1-yl)pyridin-3-yl)-2-oxopiperidin-3-yl)-3-(5-(trifluoromethyl)pyridin-2-yl)urea | 493.2 | Method F, RT = 1.67 min, 100% | ¹H NMR (400 MHz, DMSO-$d_6$): δ 9.78 (s, 1H), 8.55 (s, 1H), 8.16-8.01 (m, 2H), 7.99 (d, J = 2.7 Hz, 1H), 7.73 (d, J = 8.8 Hz, 1H), 7.42 (dd, J = 8.8, 2.7 Hz, 1H), 6.50 (d, J = 8.8 Hz, 1H), 4.44-4.30 (m, 1H), 4.15 (br. s., 1H), 3.68-3.54 (m, 2H), 3.51-3.42 (m, 2H), 3.30-3.18 (m, 5H), 2.36-2.29 (m, 1H), 2.05-1.77 (m, 7H). |

| Ex | Structure | LCMS (M + H)+ | HPLC Method, RT (min.) & Purity | ¹H NMR |
|---|---|---|---|---|
| 64 | 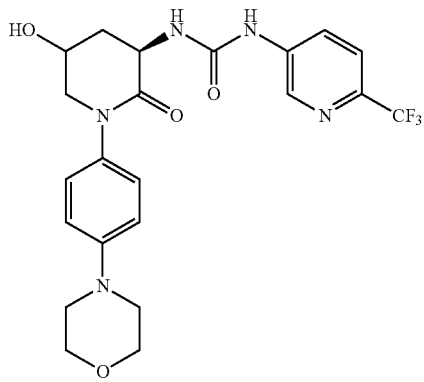 [SMILES: O=C(Nc1ccc(C(F)(F)F)nc1)N[C@@H]1CC(O)CN(c2ccc(N3CCOCC3)cc2)C1=O]<br>1-((3R)-1-(6-(3-(hydroxymethyl)piperidin-1-yl)pyridin-3-yl)-2-oxopiperidin-3-yl)-3-(4-(trifluoromethyl)phenyl)urea | 492.1 | Method F, RT = 1.85 min, 98.1% | ¹H NMR (400 MHz, DMSO-$d_6$): δ 9.20 (s, 1H), 8.00 (d, J = 2.45 Hz, 1 H), 7.55-7.62 (m, 4 H), 7.43 (dd, J = 9.05, 2.45 Hz, 1 H), 6.80 (d, J = 9.05 Hz, 1 H), 6.66 (d, J = 6.85 Hz, 1 H), 4.55 (t, J = 5.38 Hz, 1 H), 4.22-4.33 (m, 2 H), 4.08-4.17 (m, 1 H), 3.57-3.63 (m, 2 H), 3.31-3.22 (m, 3 H), 2.82-2.76 (m, 1 H), 2.23-2.35 (m, 1 H), 1.93-2.02 (m, 2 H), 1.64-1.85 (m, 3 H), 1.59 (br. s., 1 H), 1.50-1.35 (m, 1 H), 1.11-1.25 (m, 1 H) |

Example 65: 1-((3R)-5-Hydroxy-1-(4-morpholinophenyl)-2-oxopiperidin-3-yl)-3-(6-(trifluoromethyl)pyridin-3-yl)urea

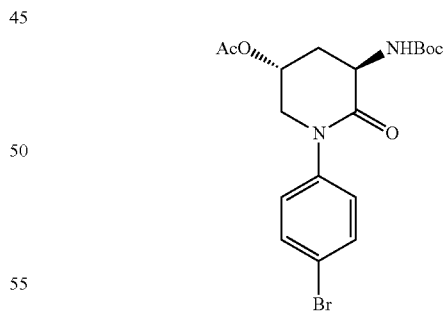

Example 65A: trans-5-((tert-butoxycarbonyl)amino)-6-oxopiperidin-3-yl acetate

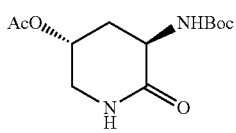 [SMILES: CC(=O)O[C@H]1CNC(=O)[C@H](NC(=O)OC(C)(C)C)C1]

tert-Butyl trans-5-hydroxy-2-oxopiperidin-3-yl)carbamate was synthesized using the procedures found in Gordon, Sandra et al, Farmaco, 52(10), 603-608: 1997. Acetic anhydride (20 mL, 210 mmol) was added to a solution of tert-butyl trans-(5-hydroxy-2-oxopiperidin-3-yl)carbamate (8.0 g, 35 mmol) in pyridine (20 mL) at rt and the reaction mixture was stirred for 12 h under nitrogen atmosphere. The mixture was concentrated under reduced pressure to give Example 65A (8.0 g, 29 mmol, 85% yield) as a white solid.

Example 65B: trans-1-(4-bromophenyl)-5-((tert-butoxycarbonyl)amino)-6-oxopiperidin-3-yl acetate A mixture of Example 65A (6.0 g, 22 mmol), 4-bromophenylboronic acid (5.3 g, 26 mmol), copper (II) acetate (4.8 g, 26 mmol) and TEA (9.2 mL, 66 mmol) in DCM (30 mL) was stirred for 2 h under an oxygen atmosphere at rt. The reaction mixture was filtered through celite and washed with ethyl acetate. The filtrate was concentrated under reduced pressure to give the crude product, which was purified via column chromatography (1:4 ethyl acetate/hexanes) to yield Example 65B (3.0 g, 7.0 mmol, 32% yield). MS(ESI) m/z: 427.0/429.0 (M+H)⁺.

Example 65C: tert-butyl (trans-1-(4-bromophenyl)-5-hydroxy-2-oxopiperidin-3-yl)carbamate

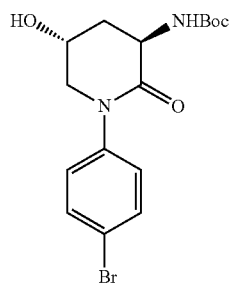

LiOH (0.19 g, 8.0 mmol) was added to a solution of Example 65B (3.4 g, 8.0 mmol) in THF/water (1:1, 30 mL). The reaction mixture was stirred for 2 h at rt. The mixture was concentrated under reduced pressure to remove the volatiles and acidified with aqueous citric acid solution. The solution was filtered and the precipitate was washed with water and dried in vacuo. The crude compound purified by prep HPLC to yield Example 65C (2.0 g, 5.2 mmol, 65% yield). MS(ESI) m/z: 385.0/3870 (M+H)$^+$.

Example 65D: tert-Butyl (5-hydroxy-1-(4-morpholinophenyl)-2-oxopiperidin-3-yl)carbamate

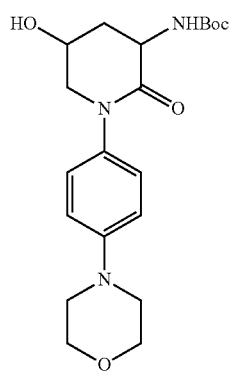

To a stirred solution of Example 65C (0.30 g, 0.78 mmol) in toluene (2 mL), were added morpholine (0.14 g, 0.78 mmol), and Cs$_2$CO$_3$ (0.51 g, 1.56 mmol). The reaction mixture was purged with nitrogen for 5 min and charged with PdOAc$_2$ (0.017 g, 0.078 mmol) and 2-dicyclohexylphosphino-2',6'-diisopropoxy-1,1'-biphenyl (0.073 g, 0.16 mmol). The reaction mixture was again purged with nitrogen for 3 min and heated to 100° C. for 16 hours. The reaction mixture was cooled, filtered through celite and the filtrate was concentrated under reduced pressure. The crude mixture was purified by column chromatography to afford a mixture of trans enantiomers of Example 65D (0.12 g, 0.22 mmol, 27.6%) as pale yellow solid. MS(ESI) m/z: 392.3 [M+H]$^+$.

Example 65E: 3-Amino-5-hydroxy-1-(4-morpholinophenyl)piperidin-2-one hydrochloride

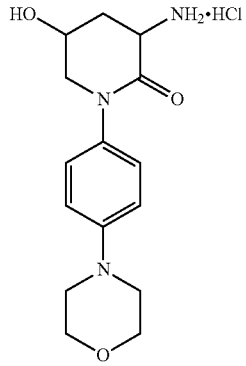

To an ice cooled solution Example 65D (0.15 g, 0.38 mmol) in 1,4-dioxane (0.5 mL), was added 4N HCl in 1,4-dioxane (0.96 mL, 3.8 mmol), and the mixture was stirred at rt for two hours. The solvent was evaporated under reduced pressure to obtain a gummy solid.

The solid was triturated with diethyl ether (2×20 mL) and dried to afford Example 65E (0.12 g, 0.26 mmol, 67%) as a off white solid. MS(ESI) m/z: 291.9 [M+H]$^+$.

Example 65: To an ice cooled solution of Example 65E (0.10 g, 0.31 mmol) in DMSO (1 mL) were added K$_2$CO$_3$ (0.11 g, 0.76 mmol) and phenyl (6-(trifluoromethyl)pyridin-3-yl)carbamate (0.095 g, 0.34 mmol). The reaction mixture was gradually warmed up to rt and stirred for 15 hours. The reaction mixture was filtered through a syringe filter, and concentrated under reduced pressure. The crude compound was purified by column chromatography followed by chiral HPLC to give Example 65 (1.5 mg, 0.003 mmol, 1.0%). MS(ESI) m/z: 480.2 (M+H)$^+$; $^1$H NMR (400 MHz, DMSO-d6): δ 9.43 (s, 1H), 8.67 (s, 1H), 8.15 (d, J=9.3 Hz, 1H), 7.76 (d, J=8.6 Hz, 1H), 7.20-7.04 (m, J=8.3 Hz, 2H), 7.02-6.86 (m, J=8.3 Hz, 2H), 6.76 (d, J=7.3 Hz, 1H), 5.30 (br. s., 1H), 4.68-4.46 (m, 1H), 4.17 (br. s., 1H), 3.80 (d, J=9.3 Hz, 1H), 3.73 (br. s., 4H), 3.48 (d, J=13.4 Hz, 1H), 3.10 (br. s., 4H), 2.24 (d, J=12.0 Hz, 1H), 2.13-1.98 (m, 1H); RT=1.11 min, 93.2% (Method F). SFC separation: Retention times: Peak 01=6 min, Peak 02=7.8 min, Peak 03=10.7 min, & Peak 04=13.5 min; Method: Column/dimensions: Luxcellulose-2 (250×21.5) mm, 5u; Temperature: 30° C.; Total Flow: 70.0 g/min; % CO$_2$: 60%; % Co-solvent: 40% of 0.2% NH$_4$OH in Methanol; Back Pressure: 100 bar.

Additional examples of compounds of this invention shown in Table 3 below were prepared using combinations of the procedures described previous examples or modifications thereof known to one skilled in the art of organic synthesis.

| Ex | Structure | LCMS (M + H)+ | HPLC Method, RT (min) & Purity | $^1$H NMR |
|---|---|---|---|---|
| 66 | 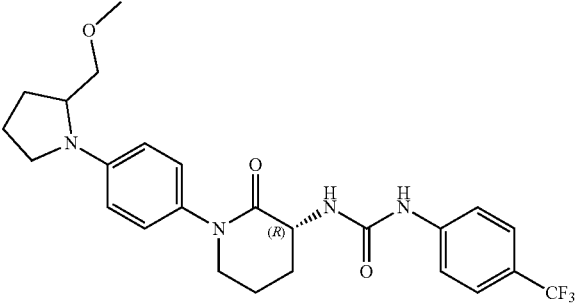<br>Homochiral<br>1-((3R)-1-(4-(2-(Methoxymethyl)pyrrolidin-1-yl)phenyl)-2-oxopiperidin-3-yl)-3-(4-(trifluoromethyl)phenyl)urea | 491.3 | Method F, RT = 1.96 min, 100% | $^1$H NMR (400 MHz, DMSO-d$_6$) δ 9.20 (s, 1H), 7.67-7.51 (m, 4H), 7.12-6.99 (d, J = 9.0 Hz, 2H), 6.66 (d, J = 6.4 Hz, 1H), 6.62-6.53 (d, J = 9.0 Hz, 2H), 4.32-4.19 (m, 1H), 3.84-3.80 (m, 1H), 3.61-3.54 (m, 2H), 3.41-3.38 (m, 1H), 3.31-3.27 (s, 3H), 3.24-3.16 (m, 2H), 3.07-2.99 (m, 1H), 2.30 (dd, J = 12.6, 6.0 Hz, 1H), 2.04-1.88 (m, 6H), 1.81-1.70 (m, 1H). |
| 67 | 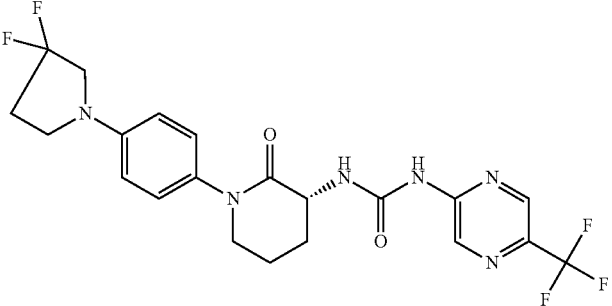<br>(R)-1-(1-(4-(3,3-Difluoropyrrolidin-1-yl)phenyl)-2-oxopiperidin-3-yl)-3-(5-(trifluoromethyl)pyrazin-2-yl)urea | 485.2 | Method F, RT = 1.82 min, 100% | $^1$H NMR (400 MHz, DMSO-d$_6$) δ 10.16 (s, 1H), 9.09 (s, 1H), 8.75-8.70 (m, 1H), 7.79 (d, J = 6.6 Hz, 1H), 7.11 (d, J = 8.8 Hz, 2H), 6.60 (d, J = 8.8 Hz, 2H), 4.42-4.33 (m, 1H), 3.72-3.58 (m, 6H), 2.59-2.55 (m, 2H), 2.36-2.29 (m, 1H), 2.03-1.97 (m, 2H), 1.83-1.74 (m, 1H). |
| 68 | 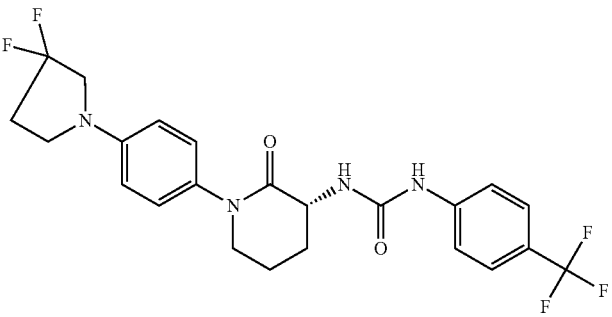<br>(R)-1-(1-(4-(3,3-Difluoropyrrolidin-1-yl)phenyl)-2-oxopiperidin-3-yl)-3-(4-(trifluoromethyl)pyrazin-2-yl)urea | 483.2 | Method F, RT = 2.037 min, 97.7% | $^1$H NMR (400 MHz, DMSO-d$_6$) δ 9.21 (s, 1H), 7.64-7.53 (m, 4H), 7.12 (d, J = 9.0 Hz, 2H), 6.67 (d, J = 6.6 Hz, 1H), 6.60 (d, J = 9.0 Hz, 2H), 4.32-4.22 (m, 1H), 3.71-3.45 (m, 6H), 2.59-2.49 (m, 2H), 2.34-2.25 (m, 1H), 2.02-1.89 (m, 2H), 1.82-1.70 (m, 1H). |

-continued

| Ex | Structure | LCMS (M + H)+ | HPLC Method, RT (min) & Purity | ¹H NMR |
|---|---|---|---|---|
| 69 | N-((S)-1-(4-((R)-2-Oxo-3-(3-(4-trifluoromethyl)phenyl)ureido)piperidin-1-yl)phenyl)pyrrolidin-3-yl)acetamide | 504.3 | Method F, RT = 1.662 min, 100% | ¹H NMR (400 MHz, DMSO-d₆) δ 9.21 (s, 1H), 8.19 (d, J = 6.8 Hz, 1H), 7.62-8.57 (m, 4H), 7.06 (d, J = 8.8 Hz, 2H), 6.67 (d, J = 6.4 Hz, 1H), 6.50 (d, J = 8.8 Hz, 2H), 4.38-4.30 (m, 1H), 4.29-4.23 (m, 1H), 3.63-3.54 (m, 2H), 3.52-3.41 (m, 1H), 3.39-3.32 (m, 1H), 3.28-3.22 (m, 1H), 3.04 (dd, J = 9.5, 4.4 Hz, 1H), 2.36-2.28 (m, 1H), 2.22-2.13 (m, 1H), 2.02-1.92 (m, 2H), 1.90-1.86 (m, 1H), 1.81 (s, 3H), 1.76 (m, 1H). |
| 70 | (R)-1-(1-(4-(3,3-Difluoropiperidin-1-yl)phenyl)-2-oxopiperidin-3-yl)-3-(4-(trifluoromethyl)phenyl)urea | 497.2 | Method F, RT = 2.060 min, 100% | ¹H NMR (400 MHz, DMSO-d₆) δ 9.21 (s, 1H), 7.62-7.57 (m, 4H), 7.12 (d, J = 9.0 Hz, 2H), 6.96 (d, J = 9.0 Hz, 2H), 6.67 (d, J = 6.8 Hz, 1H), 4.31-4.24 (m, 1H), 3.62-3.58 (m, 2H), 3.45-3.42 (m, 2H), 3.25-3.20 (m, 2H), 2.28 (dd, J = 12.2, 5.1 Hz, 1H), 2.08-1.93 (m, 4H), 1.82-1.73 (m, 3H). |
| 71 | Homochiral 1-((3R)-1-(2-Fluoro-4-(2-(methoxymethyl)piperidin-1-yl)phenyl)-2-oxopiperidin-3-yl)-3-(5-(trifluoromethyl)pyrazin-2-yl)urea | 525.3 | Method F, RT = 2.065 min, 97.9% | ¹H NMR (400 MHz, DMSO-d₆) δ 10.13 (s, 1H), 9.07 (d, J = 1.0 Hz, 1H), 8.75-8.70 (m, 1H), 7.81 (d, J = 7.1 Hz, 1H), 7.16-7.07 (m, 1H), 6.76-6.65 (m, 2H), 4.38 (dt, J = 12.2, 6.3 Hz, 1H), 4.04 (m, 1H), 3.47-3.61 (m, 2H) 3.31 (dd, J = 9.5, 5.4 Hz, 1H), 3.22 (s, 3H), 2.93-2.83 (m, 2H), 2.73 (d, J = 0.5 Hz, 1H), 2.35-2.29 (m, 1H), 2.03-1.94 (m, 2H), 1.79 (m, 2H), 1.69 (d, J = 12.0 Hz, 1H), 1.63-1.51 (m, 3H), 1.47 (m, 1H). |
| 72 | Homochiral 1-((3R)-2-Oxo-1-(4-(3-(trifluoromethyl)piperidin-1-yl)phenyl)piperidin-3-yl)-3-(4-(trifluoromethyl)phenyl)urea | 529.2 | Method F, RT = 2.204 min, 94.9% | ¹H NMR (400 MHz, DMSO-d₆) δ 9.23 (s, 1H), 7.70-7.50 (m, 4H), 7.15 (d, J = 9.0 Hz, 2H), 6.97 (d, J = 9.0 Hz, 2H), 6.68 (d, J = 6.6 Hz, 1H), 4.37-4.22 (m, 1H), 3.78 (d, J = 10.3 Hz, 1H), 3.72-3.52 (m, 3H), 2.79-2.59 (m, 3H), 2.38-2.27 (m, 1H), 2.06-1.88 (m, 3H), 1.87-1.70 (m, 2H), 1.69-1.54 (m, 1H), 1.53-1.38 (m, 1H). |

| Ex | Structure | LCMS (M + H)+ | HPLC Method, RT (min) & Purity | ¹H NMR |
|---|---|---|---|---|
| 73 | 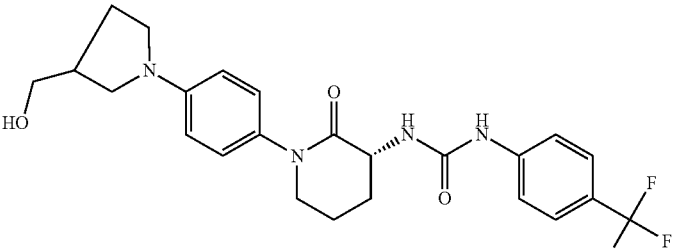<br>Homochiral<br>1-((3R)-1-(4-(3-(Hydroxymethyl)pyrrolidin-1-yl)phenyl)-2-oxopiperidin-3-yl)-3-(4-(trifluoromethyl)phenyl)urea | 477.2 | Method F, RT = 1.718 min, 100% | ¹H NMR (400 MHz, DMSO-$d_6$) δ 9.22 (s, 1H), 7.66-7.53 (m, 4H), 7.06 (d, J = 8.8 Hz, 2H), 6.67 (d, J = 6.4 Hz, 1H), 6.51 (d, J = 9.0 Hz, 2H), 4.73 (t, J = 5.0 Hz, 1H), 4.30-4.24 (m, 1H), 3.59 (t, J = 6.1 Hz, 2H), 3.50-3.32 (m, 3H), 3.26-3.18 (m, 2H), 3.05-2.99 (m, 1H), 2.46-2.41 (m, 1H), 2.32-2.25 (m, 1H), 2.05-1.82 (m, 3H), 1.72-1.64 (m, 2H). |
| 74 | 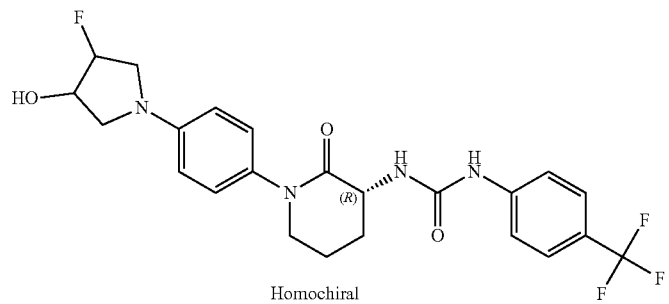<br>Homochiral<br>1-((3R)-1-(4-(3-Fluoro-4-hydroxypyrrolidin-1-yl)phenyl)-2-oxopiperidin-3-yl)-3-(4-(trifluoromethyl)phenyl)urea | 481.2 | Method F, RT = 1.692 min, 100% | ¹H NMR (400 MHz, DMSO-$d_6$) δ 9.23 (s, 1H), 7.74-7.48 (m, 4H), 7.10 (d, J = 8.8 Hz, 2H), 6.68 (d, J = 6.4 Hz, 1H), 6.52 (d, J = 8.8 Hz, 2H), 5.54 (d, J = 3.9 Hz, 1H), 5.07 (d, J = 55 Hz, 1H), 4.41-4.32 (m, 1H), 4.32-4.20 (m, 1H), 3.68-3.38 (m, 5H), 3.23-3.18 (m, 1H), 2.34-2.29 (m, 1H), 2.04-1.88 (m, 2H), 1.80-1.70 (m, 1H). |
| 75 | 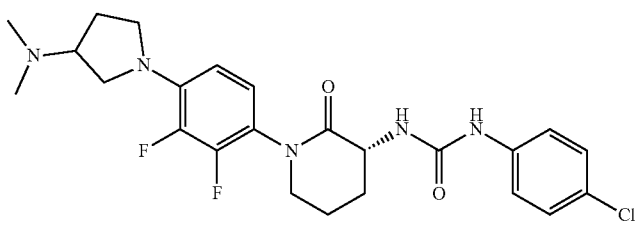<br>Homochiral<br>1-(4-Chlorophenyl)-3-((3R)-1-(4-(3-(dimethylamino)pyrrolidin-1-yl)-2,3-difluorophenyl)-2-oxopiperidin-3-yl)urea | 492.2 | Method F, RT = 1.591 min, 100% | ¹H NMR (400 MHz, DMSO-$d_6$) δ 8.89 (s, 1H), 7.50-7.39 (m, 2H), 7.33-7.16 (m, 2H), 7.05-6.92 (m, 1H), 6.67-6.47 (m, 2H), 4.39-4.22 (m, 1H), 3.61-3.39 (m, 5H), 3.27-3.22 (m, 1H), 2.92-2.87 (m, 1H), 2.37-2.18 (m, 7H), 2.18-2.05 (m, 1H), 2.04-1.92 (m, 2H), 1.88-1.68 (m, 2H). |
| 76 | 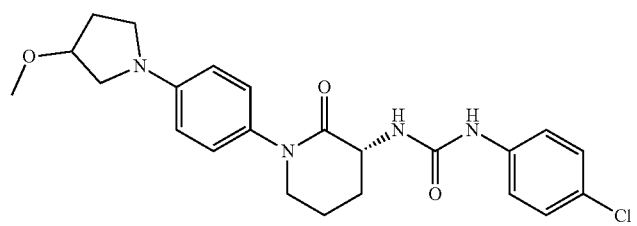<br>Homochiral<br>1-(4-Chlorophenyl)-3-((3R)-1-(4-(3-methoxypyrrolidin-1-yl)phenyl)-2-oxopiperidin-3-yl)urea | 443.2 | Method F, RT = 1.736 min, 97.5% | ¹H NMR (400 MHz, DMSO-$d_6$) δ 8.93 (s, 1H), 7.50-7.37 (m, 2H), 7.33-7.21 (m, 2H), 7.06 (d, J = 9.0 Hz, 2H), 6.63-6.42 (m, 3H), 4.32-4.20 (m, 1H), 4.09 (m, 1H), 3.58 (t, J = 6.4 Hz, 2H), 3.41 (dd, J = 10.6, 5.0 Hz, 1H), 3.31-3.15 (m, 6H), 2.31 (dt, J = 11.9, 5.7 Hz, 1H), 2.12-2.01 (m, 2H), 2.01-1.84 (m, 2H), 1.80-1.63 (m, 1H). |

-continued

| Ex | Structure | LCMS (M + H)+ | HPLC Method, RT (min) & Purity | ¹H NMR |
|---|---|---|---|---|
| 77 | Homochiral 1-((3R)-1-(4-(3-(Dimethylamino)piperidin-1-yl)phenyl)-2-oxopiperidin-3-yl)-3-(4-(trifluoromethyl)phenyl)urea | 504.3 | Method F, RT = 1.532 min, 100% | ¹H NMR (400 MHz, DMSO-d₆) δ 9.26 (s, 1H), 7.67-7.54 (m, 4H), 7.12 (d, J = 9.0 Hz, 2H), 6.94 (d, J = 9.0 Hz, 2H), 6.70 (d, J = 6.6 Hz, 1H), 4.32-4.22 (m, 1H), 3.78-3.71 (m, 1H), 3.64-3.58 (m, 3H), 3.43-3.38 (m, 1H), 2.67-2.61 (m, 2H), 2.41-2.29 (m, 7H), 2.02-1.88 (m, 3H), 1.85-1.71 (m, 2H), 1.60-1.49 (m, 1H), 1.42-1.30 (m, 1H). |
| 78 | Homochiral 1-(4-Chlorophenyl)-3-((3R)-1-(4-(3-(hydroxymethyl)piperidin-1-yl)phenyl)-2-oxopiperidin-3-yl)urea | 457.3 | Method F, RT = 1.564 min, 98.5% | ¹H NMR (400 MHz, DMSO-d₆) δ 8.94 (s, 1H), 7.51-7.36 (m, 2H), 7.33-7.19 (m, 2H), 7.17-7.02 (m, 2H), 6.91 (d, J = 9.0 Hz, 2H), 6.55 (d, J = 6.4 Hz, 1H), 4.59-4.53 (m, 1H), 4.34-4.17 (m, 1H), 3.68 (d, J = 13.0 Hz, 1H), 3.63-3.56 (m, 4H), 3.34-3.23 (m, 1H), 2.88-2.96 (m, 1 H), 2.72-2.61 (m, 1H), 2 43 (dd, J = 12.0, 10.0 Hz, 1H), 2.29 (dd, J = 12.1, 6.0 Hz, 1H), 2.04-1.90 (m, 2H), 1.84-1.64 (m, 4H), 1.55 (d, J = 13.0 Hz, 1H). |
| 79 | Homochiral 1-((3R)-1-(4-(3-(Dimethylamino)-4-hydroxypyrrolidin-1-yl)phenyl)-2-oxopiperidin-3-yl)-3-(4-(trifluoromethyl)phenyl)urea | 506.3 | Method F, RT = 1.515 min, 100% | ¹H NMR (400 MHz, DMSO-d₆) δ 9.23 (s, 1H), 7.71-7.47 (m, 4H), 7.05 (d, J = 8.8 Hz, 2H), 6.68 (d, J = 6.4 Hz, 1H), 6.50 (d, J = 8.8 Hz, 2H), 5.20 (d, J = 5.6 Hz, 1H), 4.36-4.19 (m, 2H), 3.59 (t, J = 6.2 Hz, 2H), 3.54-3.43 (m, 2H), 3.12 (dd, J = 9.9, 6.5 Hz, 1H), 3.06 (dd, J = 9.9, 5.3 Hz, 1H), 2.79-2.74 (m, 1H), 2.37-2.21 (m, 7H), 2.03-1.89 (m, 2H), 1.81-1.69 (m, 1H). |
| 80 | (R)-1-(4-Chloro-2-fluorophenyl)-3-(1-(2,3-difluoro-4-(2-oxopiperidin-1-yl)phenyl)-2-oxopiperidin-3-yl)urea | 495.2 | Method F, RT = 1.618 min, 100% | ¹H NMR (400 MHz, DMSO-d₆) δ 8.69 (d, J = 2.2 Hz, 1H), 8.16 (t, J = 8.9 Hz, 1H), 7.41 (dd, J = 11.2, 2.4 Hz, 1H), 7.37-7.24 (m, 2H), 7.19 (dd, J = 8.8, 1.2 Hz, 1H), 7.14 (d, J = 7.1 Hz, 1H), 4.47-4.31 (m, 1H), 3.75-3.62 (m, 2H), 3.63-3.58 (m, 2H), 2.46-3.41 (m, 2H), 2.29-2.25 (m, 1H), 2.13-1.96 (m, 2H), 1.95-1.72 (m, 5H). |

| Ex | Structure | LCMS (M + H)+ | HPLC Method, RT (min) & Purity | 1H NMR |
|---|---|---|---|---|
| 81 | 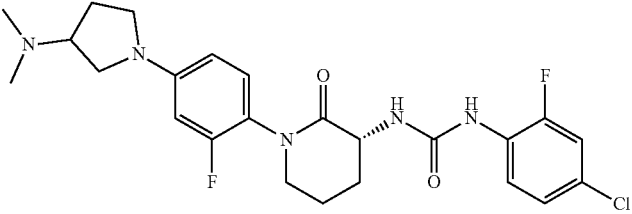<br>Homochiral<br>1-(4-Chloro-2-fluorophenyl)-3-((3R)-1-(4-(3-(dimethylamino)pyrrolidin-1-yl)-2-fluorophenyl)-2-oxopiperidin-3-yl)urea | 492.2 | Method F, RT = 1.615 min, 100% | 1H NMR (400 MHz, DMSO-d6) δ 8.69 (d, J = 2.2 Hz, 1H), 8.17 (t, J = 8.9 Hz, 1H), 7.41 (dd, J = 11.2, 2.4 Hz, 1H), 7.19 (d, J = 9.0 Hz, 1H), 7.16-7.02 (m, 2H), 6.50-6.26 (m, 2H), 4.40-4.24 (m, 1H), 3.60-3.42 (m, 4H), 3.26-3.17 (m, 1H), 3.04 (t, J = 8.7 Hz, 1H), 2.89-2.74 (m, 1H), 2.33-2.10 (m, 8H), 2.02-1.87 (m, 2H), 1.87-1.63 (m, 2H). |
| 82 | 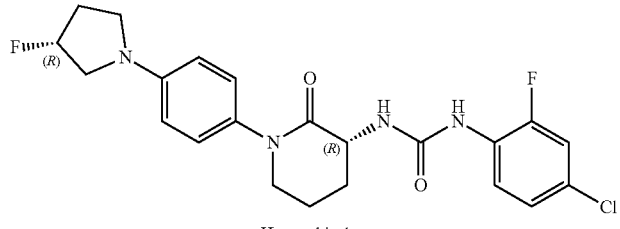<br>Homochiral<br>1-(4-Chloro-2-fluorophenyl)-3-((R)-1-(4-((R)-3-fluoropyrrolidin-1-yl)phenyl)-2-oxopiperidin-3-yl)urea | 449.1 | Method F, RT = 1.839 min, 94.1% | 1H NMR (400 MHz, DMSO-d6) δ 8.75-8.70 (m, 1H), 8.17 (t, J = 8.9 Hz, 1H), 7.41 (dd, J = 11.2, 2.2 Hz, 1H), 7.19 (d, J = 8.3 Hz, 1H), 7.14-6.98 (m, 3H), 6.57 (d, J = 8.8 Hz, 2H), 5.53-5.39 (m, 1H), 4.34-4.22 (m, 1H), 3.66-3.53 (m, 3H), 3.51-3.40 (m, 3H), 2.35-2.19 (m, 3H), 2.06-1.91 (m, 2H), 1.79-1.66 (m, 1H). |
| 83 | 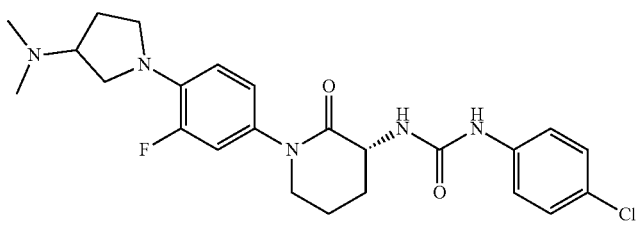<br>Homochiral<br>1-(4-Chlorophenyl)-3-((3R)-1-(4-(3-(dimethylamino)pyrrolidin-1-yl)-3-fluorophenyl)-2-oxopiperidin-3-yl)urea | 474.2 | Method F, RT = 1.546 min, 100% | 1H NMR (400 MHz, DMSO-d6) δ 8.90 (s, 1H), 7.49-7.36 (d, J = 9.0 Hz, 2H), 7.34-7.20 (d, J = 9.0 Hz, 2H), 7.10 (t, J = 8.9 Hz, 1H), 6.57 (d, J = 6.4 Hz, 1H), 6.46-6.29 (m, 2H), 4.28 (dt, J = 11.6, 5.9 Hz, 1H), 3.59-3.47 (m, 2H), 3.47-3.40 (m, 2H), 3.26-3.20 (m, 2H), 2.85-2.75 (m, 1H), 2.32-2.25 (m, 1H), 2.25-2.10 (m, 7H), 2.04-1.89 (m, 2H), 1.86-1.65 (m, 2H). |
| 84 | 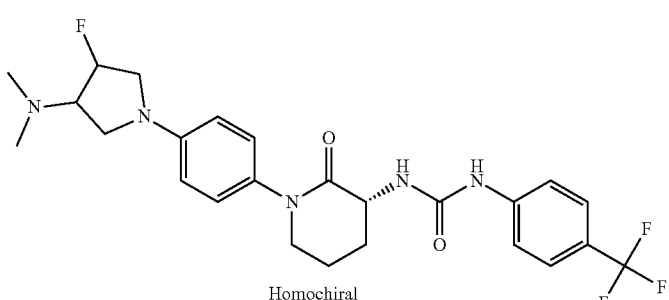<br>Homochiral<br>1-((3R)-1-(4-(3-(Dimethylamino)-4-fluoropyrrolidin-1-yl)phenyl)-2-oxopiperidin-3-yl)-3-(4-(trifluoromethyl)phenyl)urea | 508.3 | Method F, RT = 1.406 min, 100% | 1H NMR (400 MHz, DMSO-d6) δ 9.23 (s, 1H), 7.69-7.52 (m, 4H), 7.12 (d, J = 8.8 Hz, 2H), 6.69 (d, J = 6.4 Hz, 1H), 6.57 (d, J = 8.8 Hz, 2H), 5.61-5.40 (m, 1H), 4.31-4.24 (m, 1H), 3.74-3.68 (m, 2H), 3.64-3.51 (m, 3H), 3.41-3.25 (m, 2H), 2.63-2.48 (s, 6H), 2.32-2.26 (m, 1H), 2.05-1.93 (m, 2H), 1.84-1.78 (m, 1H). |

-continued

| Ex | Structure | LCMS (M + H)+ | HPLC Method, RT (min) & Purity | ¹H NMR |
|---|---|---|---|---|
| 85 | Homochiral 1-(4-Chlorophenyl)-3-((3R)-1-(2,3-difluoro-4-(3-(methyl(2,2,2-trifluoroethyl)amino)pyrrolidin-1-yl)phenyl)-2-oxopiperidin-3-yl)urea | 560.2 | Method F, RT = 2.184 min, 100% | ¹H NMR (400 MHz, DMSO-$d_6$) δ 8.89 (s, 1H), 7.51-7 35 (m, 2H), 7.33-7.18 (m, 2H), 7.05-6.92 (m, 1H), 6.65-6.47 (m, 2H), 4.38-4.24 (m, 1H), 3.66-3.43 (m, 4H), 3.43-3.34 (m, 2H), 3.30-3.19 (m, 3H), 2.43 (s, 3H), 2.32-2.22 (m, 1H), 2.19-2.07 (m, 1H), 2.06-1.89 (m, 2H), 1.87-1.69 (m, 2H). |
| 86 | Homochiral 1-(4-((R)-3-(3-(4-Chloro-2-fluorophenyl)ureido)-2-oxopiperidin-1-yl)phenyl)-N,N-dimethylpyrrolidine-3-carboxamide | 502.2 | Method F, RT = 1.649 min, 99.3% | ¹H NMR (400 MHz, DMSO-$d_6$) δ 8.69 (s, 1H), 8.17 (t, J = 8.9 Hz, 1H), 7.39 (dd, J = 11.2, 2.4 Hz, 1H), 7.23-7.14 (m, 1H), 7.11 (d, J = 6.6 Hz, 1H), 7.03 (d, J = 9.0 Hz, 2H), 6.51 (d, J = 8.8 Hz, 2H), 4.34-4.19 (m, 1H), 3.64-3.54 (m, 2H), 3.53-3.39 (m, 2H), 3.35-3.22 (m, 3H), 3.08 (s, 3H), 2.86 (s, 3H), 2.35-2.24 (m, 1H), 2.23-2.01 (m, 2H), 2.01-1.83 (m, 2H), 1.79-1.67 (m, 1H). |
| 87 | Homochiral 1-(4-Chlorophenyl)-3-((3R)-1-(2,3-difluoro-4-(3-(methylsulfonyl)pyrrolidin-1-yl)phenyl)-2-oxopiperidin-3-yl)urea | 527.1 | Method F, RT = 1.618 min, 100% | ¹H NMR (400 MHz, DMSO-$d_6$) δ 8.88 (s, 1H), 7.43-7.40 (m, 2H), 7.29-7.26 (m, 2H), 7.07-7.01 (m, 1H), 6.67-6.58 (m, 2H), 4.37-4.26 (m, 1H), 4.10-4.06 (m, 1H), 3.74-3.72 (m, 2H), 3.59-3.56 (m, 3H), 3.46-3.39 (m, 1H), 3.06 (s, 3H), 2.36-2.33 (m, 3H), 2.09-1.97 (m, 2H), 1.82-1.75 (m, 1H). |
| 88 | 1-(4-Chloro-2-fluorophenyl)-3-((R)-1-(2,3-difluoro-4-((R)-3-fluoropyrrolidin-1-yl)phenyl)-2-oxopiperidin-3-yl)urea | 485.1 | Method F, RT = 1.936 min, 100% | ¹H NMR (400 MHz, DMSO-$d_6$) δ 8.66 (s, 1H), 8.16 (t, J = 8.9 Hz, 1H), 7.40 (dd, J = 11.2, 2.4 Hz, 1H), 7.18 (d, J = 8.8 Hz, 1H), 7.12 (d, J = 7.1 Hz, 1H), 7.06-6.96 (m, 1H), 6.67-6.49 (m, 1H), 5.41 (d, J = 40.8 Hz, 1H), 4.40-4.26 (m, 1H), 3.77-3.46 (m, 6H), 2.33-2.15 (m, 3H), 2.03-1.85 (m, 2H), 1.83-1.68 (m, 1H). |

| Ex | Structure | LCMS (M + H)+ | HPLC Method, RT (min) & Purity | ¹H NMR |
|---|---|---|---|---|
| 89 | Homochiral 1-(4-Chloro-2-fluorophenyl)-3-((3R)-1-(2,3-difluoro-4-(3-(methylsulfonyl)pyrrolidin-1-yl)phenyl)-2-oxopiperidin-3-yl)urea | 545.1 | Method F, RT = 1.680 min, 100% | ¹H NMR (400 MHz, DMSO-$d_6$) δ 8.66 (s, 1H), 8.16 (t, J = 8.9 Hz, 1H), 7.40 (dd, J= 1.2, 2.4 Hz, 1H), 7.18 (d, J = 8.8 Hz, 1H), 7.12 (d, J = 6.8 Hz, 1H), 7.08-6.97 (m, 1H), 6.72-6.55 (m, 1H), 4.41-4.29 (m, 1H), 4.06-4.03 (m, 1H), 3.81-3.66 (m, 2H), 3.65-3.47 (m, 3H), 3.43-3.41 (m, 1H), 3.06 (s, 3H), 2.43-2.19 (m, 3H), 2.06-1.86 (m, 2H), 1.84-1.69 (m, 1H). |
| 90 | Homochiral 1-(4-Chloro-2-fluorophenyl)-3-((3R)-1-(2,6-difluoro-4-(3-(methylsulfonyl)pyrrolidin-1-yl)phenyl)-2-oxopiperidin-3-yl)urea | 545.2 | Method F, RT = 1.733 min, 100% | ¹H NMR (400 MHz, DMSO-$d_6$) δ 8.64 (d, J = 2.0 Hz, 1H), 8.16 (t, J = 8.8 Hz, 1H), 7.40 (dd, J = 11.1, 2.3 Hz, 1H), 7.27-7.05 (m, 2H), 6.39 (s, 1H), 6.42 (s, 1H), 4.41-4.30 (m, 1H), 4.11 (dt, J = 13.4, 6.7 Hz, 1H), 3.69-3.59 (m, 2H), 3.59-3.30 (m, 4H), 3.07 (s, 3H), 2.43-2.38 (m, 2H), 2.35-2.25 (m, 1H), 2.10-1.88 (m, 2H), 1.80-1.67 (m, 1H). |
| 91 | Homochiral 1-(4-Chloro-2-fluorophenyl)-3-((3R)-1-(2-cyclopropyl-4-(3-(methylsulfonyl)pyrrolidin-1-yl)phenyl)-2-oxopiperidin-3-yl)urea | 549.2 | Method F, RT = 1.930 min, 100% | ¹H NMR (400 MHz, DMSO-$d_6$) δ 8.71 (s, 1H), 8.17 (t, J = 8.9 Hz, 1H), 7.40 (d, J = 12.7 Hz, 1H), 7.18 (d, J = 8.6 Hz, 1H), 7.13 (d, J = 6.4 Hz, 1H), 6.97 (dd, J = 8.3, 5.1 Hz, 1H), 6.45 (d, J = 8.1 Hz, 1H), 6.15-6.10 (m, 1H), 4.32-4.28 (m, 1H), 4.14-4.00 (m, 1H), 3.64-3.46 (m, 5H), 3.06 (s, 3H), 2.40-2.31 (m, 4H), 1.99 (d, J = 5.1 Hz, 2H), 1.88-1.65 (m, 2H), 0.90 (d, J = 8.3 Hz, 1H), 0.82 (d, J = 4.4 Hz, 2H), 0.52 (d, J = 4.4 Hz, 1H). |
| 92 | Homochiral (R)-1-(4-Chlorophenyl)-3-(1-(4-(3,3-dimethylpyrrolidin-1-yl)phenyl)-2-oxopiperidin-3-yl)urea | 441.2 | Method E, RT = 2.07 min, 99% | ¹H NMR (400 MHz, DMSO-$d_6$) δ 9.20-9.15 (m, 1H), 7.72-7.66 (m, 2H), 7.56-7.50 (m, 2H), 7.34-7.27 (m, 2H), 6.74-6.71 (m, 2H), 4.53-4.47 (m, 1H), 3.86-3.81 (m, 2H), 3.62-3.57 (m, 2H), 3.29-3.25 (m, 2H), 2.94 (td, J = 1.8, 3.7 Hz, 3H), 2.23-2.18 (m, 2H), 2.06-1.99 (m, 3H), 1.37 (m, 6H). |

| Ex | Structure | LCMS (M + H)+ | HPLC Method, RT (min) & Purity | $^1$H NMR |
|---|---|---|---|---|
| 93 | Homochiral 1-(4-Chlorophenyl-3-((3R)-1-(4-(3-hydroxy-3-methylpiperidin-1-yl)phenyl)-2-oxopiperidin-3-yl)urea | 457.2 | Method F, RT = 1.8 min, 99% | $^1$H NMR (400 MHz, DMSO-d$_6$) δ 9.24-9.17 (m, 1H), 7.73-7.65 (m, 2H), 7.57-7.50 (m, 2H), 7.38-7.31 (m, 2H), 7.18-7.11 (m, 2H), 6.82 (d, J = 6.6 Hz, 1H), 4.70 (s, 1H), 3.89-3.81 (m, 2H), 3.36-3.27 (m, 2H), 3.19 (d, J = 3.7 Hz, 2H), 2.94 (td, J = 1.8, 3.8 Hz, 2H), 2.25-2.16 (m, 2H), 2.10-1.96 (m, 2H), 1.80-1.72 (m, 3H), 1.43 (s, 3H). |
| 94 | Homochiral 1-(4-Chlorophenyl)-3-((3R)-1-(4-(3-hydroxy-3-methylpyrrolidin-1-yl)phenyl)-2-oxopiperidin-3-yl)urea | 443.1 | Method E, RT = 1.5 min, 100% | $^1$H NMR (400 MHz, DMSO-d$_6$) δ 9.17 (s, 1H), 7.73-7.64 (m, 2H), 7.57-7.49 (m, 2H), 7.33-7.26 (m, 2H), 6.79 (d, J = 6.4 Hz, 1H), 6.74-6.67 (m, 2H), 5.03 (s, 1H), 4.56-4.44 (m, 1H), 3.83 (t, J = 6.2 Hz, 2H), 3.63-3.60 (m, 1H), 3.53 (d, J = 4.2 Hz, 1H), 3.46-3.37 (m, 2H), 2.58-2.51 (m, 1H), 2.25-2.10 (m, 3H), 2.26-2.08 (m, 1H), 2.07-1.91 (m, 1H), 1.61 (s, 3H). |
| 95 | 1-(4-Chlorophenyl)-3-((R)-2-oxo-1-(4-((3aR,6aS)-tetrahydro-1H-furo[3,4-c]pyrrol-5(3H)-yl)phenyl)piperidin-3-yl)urea | 455.2 | Method F, RT = 1.6 min, 98% | $^1$H NMR (400 MHz, DMSO-d$_6$) δ 8.92 (s, 1H), 7.47-7.39 (m, 2H), 7.32-7.24 (m, 2H), 7.08 (d, J = 8.8 Hz, 2H), 6.62 (d, J = 8.8 Hz, 2H), 6.56-6.52 (m, 1H), 4.31-4.21 (m, 2H), 3.89-3.84 (m, 2H), 3.63-3.49 (m, 3H), 3.22-3.12 (m, 2H), 3.06-2.93 (m, 3H), 2.02-1.88 (m, 3H), 1.83-1.66 (m, 2H). |
| 96 | (R)-1-(1-(4-(5-Azaspiro[2.4]heptan-5-yl)phenyl)-2-oxopiperidin-3-yl)-3-(4-chlorophenyl)urea | 439.1 | Method E, RT = 1.76 min, 92% | $^1$H NMR (400 MHz, DMSO-d$_6$) δ 8.92 (s, 1H), 7.46-7.40 (m, 2H), 7.30-7.24 (m, 2H), 7.08-7.03 (m, 2H), 6.56 (d, J = 6.5 Hz, 1H), 6.52-6.45 (m, 2H), 4.30-4.21 (m, 1H), 3.62-3.58 (m, 2H), 3.16 (s, 2H), 2.97-2.94 (m, 2H), 2.34-2.24 (m, 1H), 2.02-1.84 (m, 2H), 1.81-1.66 (m, 1H), 1.30-1.19 (m, 2H), 0.45 (m, 4H). |

-continued

| Ex | Structure | LCMS (M + H)+ | HPLC Method, RT (min) & Purity | ¹H NMR |
|---|---|---|---|---|
| 97 | Homochiral 1-(4-Chlorophenyl)-3-((3R)-1-(4-(3-cyclopropylpyrrolidin-1-yl)phenyl)-2-oxopiperidin-3-yl)urea | 453.2 | Method E, RT = 2.4 min, 99% | ¹H NMR (400 MHz, DMSO-d₆) δ 9.17 (s, 1H), 7.73-7.65 (m, 2H), 7.57-7.49 (m, 2H), 7.35-7.26 (m, 2H), 6.83-6.73 (m, 3H), 4.55-4.45 (m, 1H), 3.86-3.82 (m, 2H), 3.66-3.60 (m, 2H), 3.51-3.42 (m, 1H), 3.25 (dd, J = 7.6, 8.6 Hz, 1H), 2.56-2.51 (m, 1H), 2.40-2.31 (m, 1H), 2.26-2.16 (m, 2H), 2.10-1.92 (m, 3H), 1.13-0.98 (m, 1H), 0.76-0.64 (m, 2H), 0.48-0.39 (m, 2H). |
| 98 | 1-(4-Chlorophenyl)-3-((R)-1-(4-((3R,4S)-3,4-difluoropyrrolidin-1-yl)phenyl)-2-oxopiperidin-3-yl)urea | 449.2 | Method E, RT = 1.7 min, 96% | ¹H NMR (400 MHz, DMSO-d₆) δ 9.17 (s, 1H), 7.46-7.38 (m, 2H), 7.30-7.24 (m, 2H), 7.14-7.07 (m, 2H), 6.61-6.53 (m, 3H), 5.53-5.45 (m, 1H), 5.40-5.31 (m, 1H), 4.26 (td, J = 6.1, 11.4 Hz, 1H), 3.74-3.55 (m, 4H), 3.54-3.51 (m, 2H), 2.31-2.25 (m, 1H), 1.96-1.90 (m, 2H), 1.82-1.69 (m, 1H). |
| 99 | Homochiral (R)-1-(4-Chlorophenyl)-3-(1-(4-(4-fluoro-4-methylpiperidin-1-yl)phenyl-2-oxopiperidin-3-yl)urea | 459.2 | Method E, RT = 2.0 min, 98% | ¹H NMR (400 MHz, DMSO-d₆) δ 8.97-8.89 (m, 1H), 7.46-7.39 (m, 2H), 7.30-7.24 (m, 2H), 7.14-7.08 (m, 2H), 6.96 (d, J = 9.0 Hz, 2H), 6.55 (d, J = 6.4 Hz, 1H), 4.26 (td, J = 5.9, 11.6 Hz, 1H), 3.66-3.57 (m, 2H), 3.52-3.41 (m, 2H), 3.08-2.95 (m, 2H), 2.31-2.25 (m, 1H), 1.99-1.91 (m, 2H), 1.87-1.67 (m, 5H), 1.34 (s, 3H). |
| 100 | Homochiral (R)-1-(4-Chlorophenyl)-3-(1-(4-(4-hydroxy-4-(trifluoromethyl)piperidin-1-yl)phenyl)-2-oxopiperidin-3-yl)urea | 511.2 | Method E, RT = 1.4 min, 99% | ¹H NMR (400 MHz, DMSO-d₆) δ 8.92 (s, 1H), 7.50-7.38 (m, 2H), 7.31-7.23 (m, 2H), 7.17-7.09 (m, 2H), 7.03-6.95 (m, 2H), 6.54 (d, J = 6.5 Hz, 1H), 5.97 (s, 1H), 4.32-4.22 (m, 1H), 3.68-3.57 (m, 4H), 2.99-2.94 (m, 2H), 2.36-2.24 (m, 1H), 2.03-1.90 (m, 2H), 1.85-1.68 (m, 5H). |

| Ex | Structure | LCMS (M + H)+ | HPLC Method, RT (min) & Purity | ¹H NMR |
|---|---|---|---|---|
| 101 | (R)-1-(1-(4-(1-Oxa-8-azaspiro[4.5]decan-8-yl)phenyl)-2-oxopiperidin-3-yl)-3-(4-chlorophenyl)urea | 483.1 | Method F, RT = 1.7 min, 99% | ¹H NMR (400 MHz, DMSO-d₆) δ 8.81 (s, 1H), 7.35-7.28 (m, 2H), 7.16 (d, J = 8.9 Hz, 2H), 6.98 (d, J = 8.9 Hz, 2H), 6.82 (d, J = 9.0 Hz, 2H), 6.42 (d, J = 6.5 Hz, 1H), 4.20-4.09 (m, 1H), 3.65-3.60 (m, 2H), 3.51-3.47 (m, 2H), 3.14-3.04 (m, 4H), 2.21-2.13 (m, 1H), 1.89-1.72 (m, 4H), 1.69-1.48 (m, 7H). |
| 102 | Homochiral (R)-1-(1-(4-(2-Oxa-8-azaspiro[4.5]decan-8-yl)phenyl)-2-oxopiperidin-3-yl)-3-(4-chlorophenyl)urea | 483.2 | Method E, RT = 1.2 min, 95% | ¹H NMR (400 MHz, DMSO-d₆) δ 8.81 (s, 1H), 7.35-7.28 (m, 2H), 7.16 (d, J = 8.9 Hz, 2H), 6.99 (d, J = 8.9 Hz, 2H), 6.83 (d, J = 8.9 Hz, 2H), 6.42 (d, J = 6.6 Hz, 1H), 4.15 (td, J = 6.1, 11.7 Hz, 1H), 3.68-3.62 (m, 2H), 3.51-3.47 (m, 2H), 3.13-2.97 (m, 6H), 2.20-2.13 (m, 1H), 1.91-1.79 (m, 2H), 1.65-1.60 (m, 3H), 1.54-1.48 (m, 4H). |
| 103 | Homochiral 1-(4-Chlorophenyl)-3-((3R)-1-(6-(3-(dimethylamino)pyrrolidin-1-yl)pyridin-3-yl)-2-oxopiperlidin-3-yl)urea | 457.2 | Method F, RT = 1.284 min, 100% | ¹H NMR (400 MHz, DMSO-d₆) δ 8.93 (s, 1H), 7.98 (d, J = 2.7 Hz, 1H), 7.46-7.40 (m, 3H), 7.35-7.21 (m, 2H), 6.56 (d, J = 7.1 Hz, 1H), 6.47 (d, J = 8.8 Hz, 1H), 4.35-4.20 (m, 1H), 3.73-3.49 (m, 4H), 3.31-3.25 (m, 1H), 3.15-3.05 (m, 1H), 2.83-2.75 (m, 1H), 2.32-2.08 (m, 8H), 2.04-1.88 (m, 2H), 1.88-1.68 (m, 2H). |
| 104 | 1-((R)-1-(6-((1R,5S)-8-Oxa-3-azabicyclo[3.2.1]octan-3-yl)pyridin-3-yl)-2-oxopiperidin-3-yl)-3-(4-(trifluoromethyl)phenyl)urea | 490.2 | Method F, RT = 1.659 min, 100% | ¹H NMR (400 MHz, DMSO-d₆) δ 9.25-9.20 (m, 1H), 8.06-8.02 (m, 1H), 7.63-7.58 (m, 4H), 7.47 (d, J = 8.8 Hz, 1H), 6.74 (d, J = 9.0 Hz, 1H), 6.69 (d, J = 5.9 Hz, 1H), 4.44 (m, 2H), 4.32 (d, J = 5.1 Hz, 1H), 3.80 (d, J = 12.0 Hz, 2H), 3.62 (m, 2H), 3.01-2.82 (m, 3H), 2.32-2.28 (m, 1H), 1.98 (m, 2H), 1.83 (m, 2H), 1.75 (m, 2H). |

-continued

| Ex | Structure | LCMS (M + H)+ | HPLC Method, RT (min) & Purity | ¹H NMR |
|---|---|---|---|---|
| 105 | 1-(4-Chloro-2-fluorophenyl)-3-fluoropyrrolidin-1-yl)pyridin-3-yl)-2-oxopiperidin-3-yl)urea | 450.2 | Method F, RT = 1.181 min, 100% | ¹H NMR (400 MHz, DMSO-d₆) δ 8.71 (d, J = 2.2 Hz, 1H), 8.16 (t, J = 8.8 Hz, 1H), 8.00 (d, J = 2.4 Hz, 1H), 7.53-7.32 (m, 2H), 7.18 (dt, J = 8.8, 1.7 Hz, 1H), 7.12 (d, J = 6.6 Hz, 1H), 6.52 (d, J = 8.8 Hz, 1H), 5.51-5.38 (m, 1H), 4.34-4.25 (m, 1H), 3.72 (t, J = 13.3 Hz, 1H), 3.67-3.50 (m, 4H), 3.47-3.39 (m, 1H), 2.32-2.18 (m, 2H), 2.18-2.08 (m, 1H), 2.05-1.85 (m, 2H), 1.83-1.68 (m, 1H). |
| 106 | 1-(4-Chloro-2-fluorophenyl)-3-((R)-1-(6-((R)-3-hydroxypyrrolidin-1-yl)pyridin-3-yl)-2-oxopiperidin-3-yl)urea | 448.2 | Method F, RT = 1.240 min, 98.2% | ¹H NMR (400 MHz, DMSO-d₆) δ 8.69 (d, J = 2.0 Hz, 1H), 8.16 (t, J = 8.8 Hz, 1H), 7.97 (d, J = 2.7 Hz, 1H), 7.49-7.27 (m, 2H), 7.18 (d, J = 8.8 Hz, 1H), 7.11 (d, J = 6.6 Hz, 1H), 6.43 (d, J = 8.8 Hz, 1H), 4.96-4.90 (m, 1H), 4.44-4.35 (m, 1H), 4.33-4.21 (m, 1H), 3.67-3.53 (m, 2H), 3.52-3.39 (m, 4H), 2.31-2.27 (m, 1H), 2.12-1.82 (m, 4H), 1.82-1.70 (m, 1H). |
| 107 | 1-((R)-1-(4-((1R,5S)-8-oxa-3-azabicyclo[3.2.1]octan-3-yl)-2-fluorophenyl)-2-oxopiperidin-3-yl)-3-(4-chlorophenyl)urea | 473.2 | Method F, RT = 1.968 min, 100% | ¹H NMR (400 MHz, DMSO-d₆) δ 8.88 (s, 1H), 7.41 (d, J = 8.8 Hz, 2H), 7.27 (d, J = 8.8 Hz, 2H), 7.13 (t, J = 8.9 Hz, 1H), 6.73-6.62 (m, 2H), 6.55 (m, 1H), 4.42 (m, 2H), 4.31-4.22 (m, 2H), 3.39 (m, 2H), 3.17 (m, 1H), 2.81 (m, 2H), 2.26 (m, 1H), 2.01-1.91 (m, 2H), 1.86-1.66 (m, 5H). |
| 108 | 1-((3R)-1-(4-(3-(methylsulfonyl)pyrrolidin-1-yl)phenyl)-2-oxopiperidin-3-yl)-3-(4-(trifluoromethyl)phenyl)urea | 525.2 | Method F, RT = 1.662 min, 100% | ¹H NMR (400 MHz, DMSO-d₆) δ 9.23 (s, 1H), 7.69-7.52 (m, 4H), 7.10 (d, J = 8.8 Hz, 2H), 6.68 (d, J = 6.6 Hz, 1H), 6.60 (d, J = 8.8 Hz, 2H), 4.29 (m, 1H), 4.10 (m, 1H), 3.66-3.51 (m, 4H), 3.46-3.40 (m, 1H), 3.33-3.30 (m, 1H), 3.06 (s, 3H), 2.39 (m, 2H), 2.34-2.28 (m, 1H), 2.04-1.87 (m, 2H), 1.85-1.73 (m, 1H). |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

The invention claimed is:

1. A compound of formula I

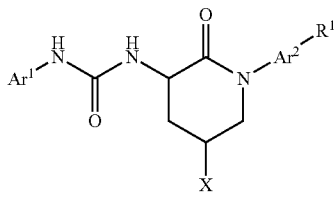

where:
Ar$^1$ is phenyl, pyridinyl, pyridazinyl, pyrimidinyl, pyrazinyl, or benzodioxyl, and is substituted with 1-3 substituents selected from cyano, halo, alkyl, fluoroalkyl, alkoxy, fluoroalkoxy, and alkylthio;
Ar$^2$ is phenyl, pyridinyl, pyridazinyl, pyrimidinyl, or pyrazinyl, and is substituted with 0-3 substituents selected from cyano, halo, alkyl, fluoroalkyl, cycloalkyl, alkoxy, and fluoroalkoxy;
R$^1$ is azetidinyl, pyrrolidinyl, piperidinyl, piperazinyl, morpholinyl, homopiperidinyl, homopiperazinyl, or homomorpholinyl, and is substituted with 0-3 substituents selected from cyano, fluoro, alkyl, fluoroalkyl, hydroxyalkyl, alkoxyalkyl, cycloalkyl, hydroxy, alkoxy, fluoroalkoxy, (R$^2$)(R$^3$)N, alkylcarbonyl, ((R$^2$)(R$^3$)N)carbonyl, alkylsufonyl, and oxo;
or R$^1$ is 5-azaspiro[2.4]heptan-5-yl, 1-oxa-8-azaspiro[4.5]decan-8-yl, 2-oxa-6-azaspiro[3.3]heptanyl, 2-oxa-8-azaspiro[4.5]decan-8-yl, or 8-oxa-3-azabicyclo[3.2.1]octanyl, or tetrahydro-1H-furo[3,4-c]pyrrol-5(3H)-yl; and
R$^2$ is hydrogen, alkyl, haloalkyl, alkylcarbonyl, or alkylsulfonyl;
R$^3$ is hydrogen or alkyl;
or NR$^2$R$^3$ taken together is selected from azetidinyl, pyrrolidinyl, piperidinyl, piperazinyl, and morpholinyl, and is substituted with 0-3 substituents selected from fluoro, alkyl, fluoroalkyl, alkoxy, and haloalkoxy; and
X is hydrogen, fluoro, hydroxy, or alkoxy;
or a pharmaceutically acceptable salt thereof.

2. A compound of claim 1 where
Ar$^1$ is phenyl or pyridinyl and is substituted with 1-3 substituents selected from cyano, halo, alkyl, fluoroalkyl, alkoxy, fluoroalkoxy, and alkylthio;
Ar$^2$ is phenyl or pyridinyl and is substituted with 0-3 substituents selected from cyano, halo, alkyl, fluoroalkyl, alkoxy, and fluoroalkoxy;
R$^1$ is azetidinyl, pyrrolidinyl, piperidinyl, piperazinyl, morpholinyl, homopiperidinyl, homopiperazinyl, or homomorpholinyl, and is substituted with 0-3 substituents selected from cyano, fluoro, alkyl, fluoroalkyl, hydroxyalkyl, alkoxyalkyl, hydroxy, alkoxy, fluoroalkoxy, alkylcarbonyl, alkylsufonyl, and oxo; and
X is hydrogen, fluoro, hydroxy, or alkoxy;
or a pharmaceutically acceptable salt thereof.

3. A compound of claim 1 where Ar$^1$ is phenyl or pyridinyl and is substituted with 1-3 substituents selected from cyano, halo, alkyl, fluoroalkyl, alkoxy, fluoro, and alkylthio.

4. A compound of claim 1 where Ar$^2$ is phenyl or pyridinyl and is substituted with 0-3 substituents selected from cyano, halo, alkyl, fluoroalkyl, alkoxy, and fluoroalkoxy.

5. A compound of claim 1 where R$^1$ is azetidinyl, pyrrolidinyl, piperidinyl, piperazinyl, morpholinyl, homopiperidinyl, homopiperazinyl, or homomorpholinyl, and is substituted with 0-3 substituents selected from cyano, fluoro, alkyl, haloalkyl, hydroxyalkyl, alkoxyalkyl, hydroxy, alkoxy, fluoroalkoxy, alkylcarbonyl, alkylsufonyl, and oxo.

6. A composition comprising a compound of claim 1, or a pharmaceutically acceptable salt thereof, and a pharmaceutically acceptable carrier, diluent, or excipient.

7. A method for treating heart disease comprising administering a therapeutically effective amount of a compound of claim 1 to a patient in need thereof.

8. The method of claim 7 wherein the heart disease is selected from the group consisting of angina pectoris, unstable angina, myocardial infarction, heart failure, acute coronary disease, acute heart failure, chronic heart failure, and cardiac iatrogenic damage.

9. The method of claim 7 wherein the treatment is post myocardial infarction.

* * * * *